(12) United States Patent
Kent et al.

(10) Patent No.: US 6,495,314 B1
(45) Date of Patent: Dec. 17, 2002

(54) PROCESS FOR CHARACTERIZING PROTEINS

(75) Inventors: Stephen B. H. Kent, San Francisco, CA (US); Tom W. Muir, New York, NY (US); Philip E. Dawson; Michael C. Fitzgerald, both of San Diego, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 09/043,877

(22) PCT Filed: Sep. 27, 1996

(86) PCT No.: PCT/US96/15516
§ 371 (c)(1),
(2), (4) Date: Jun. 19, 1998

(87) PCT Pub. No.: WO97/11958
PCT Pub. Date: Apr. 3, 1997

Related U.S. Application Data
(60) Provisional application No. 60/004,653, filed on Sep. 29, 1995.

(51) Int. Cl.$^7$ ................................................. C07K 1/04
(52) U.S. Cl. ........................... 435/4; 435/7.1; 435/19; 435/23; 435/24; 435/106; 435/DIG. 15; 530/300; 530/344; 530/350
(58) Field of Search ............................ 435/4, 7.1, 19, 435/23, 24, 106, DIG. 15; 530/300, 344, 350

(56) References Cited

PUBLICATIONS

Furka, et al., "General Method for Rapid Synthesis of Multicomponent Peptide Mixtures", *Int. J. Peptide Protein Res.* 37:487–493 (1991).
Wells, "Systematic Mutational Analyses of Protein–Protein Interfaces", *Methods Enzymology* 202: 390–411 (1991).
Lam, et al., "A New Type of Synthetic Peptide Library for Identifying Ligand–Binding Activity", *Nature* 354:82–84 (1991).
Schnölzer, et al., "Constructing Proteins by Dovetailing Unprotected Synthetic Peptides: Backbone–Engineered HIV Protease", *Science* 256:221–225 (1992).
Muir, et al., "The Chemical Synthesis of Proteins", *Curr. Opin. Biotech.* 4:420–427 (1993).
Chait, et al., "Protein Ladder Sequencing", *Science* 262:89–92 (1993).

Nielsen, et al., "Synthetic Methods for the Implementation of Encoded Combinatorial Chemistry", *J. Am. Chem. Soc.* 115:9812–9813 (1993).
Baca, et al., "Catalytic Contribution of Flap–Substrate Hydrogen Bonds in "HIV–1 Protease" Explored by Chemical Synthesis", *Proc. Natl. Acad. Sci. USA 90*: 11638–11642 (1993).
Smith, "Synthetic DNA and Biology (Nobel Lecture)", *Angew. Chem. Int. Ed. Engl. 33*: 1214–1221 (1994).
Jackson, et al., "A Designed Peptide Ligase for Total Synthesis of Ribonuclease A with Unnatural Catalytic Residues", *Science 266*: 243–247 (1994).
Dawson, et al., "Synthesis of Proteins by Native Chemical Ligation", *Science 266*: 776–779 (1994).
Canne, et al., "Total Chemical Synthesis of a Unique Transcription Factor–Related Protein: cMyc–Max", *J. Am. Chem. Soc. 117*: 2998–3007 (1995).
Fitzterald, et al., "Total Chemical Synthesis and Cataytic Properties of the Enzyme Enantiomers L– and D–4–Oxaloctoronate Tautomerase", *J. Am. Chem. Soc. 117*: 11075–11080 (1995).
Englebretsen, et al., "A Novel Thioether Linker: Chemical Synthesis of a HIV–1 Protease Analogue by Thioether Ligation", *Tetrahedron Lett.* 368871–8874 (1995).
Thompson, et al., "Synthesis and Application of Small Molecule Libraries", *Chem. Rev. 96*: 555–600 (1996).

*Primary Examiner*—Bennett Celsa
(74) *Attorney, Agent, or Firm*—Donald G. Lewis

(57) ABSTRACT

A protein signature analysis is obtained using a peptide ladder library. The molecular signature of a protein is defined to be that subsequence of amino acid positions within the protein which are essential for the protein to bind to a target molecule. The molecular signature may be determined by screening a peptide ladder library which corresponds to the protein against the target molecule. The peptide ladder library is a library of m peptides wherein each peptide has an amino acid sequence of length m corresponding to an amino acid sequence of the protein, with one exception, viz. peptide$_m$ has a substitute amino acid at position$_m$ and the substitute amino acid is attached by a labile bond to its neighboring amino acid. Screening the peptide ladder library against the target molecule results in a division of the original mixture into a positive (functional) pool and a negative (non-functional) pool. The pools are separated and subjected to cleavage to obtain cleavage products. Analysis of cleavage products by mass spectrometry identifies the positions that are essential for the protein to bind to its molecular target.

6 Claims, 39 Drawing Sheets

FIG. I

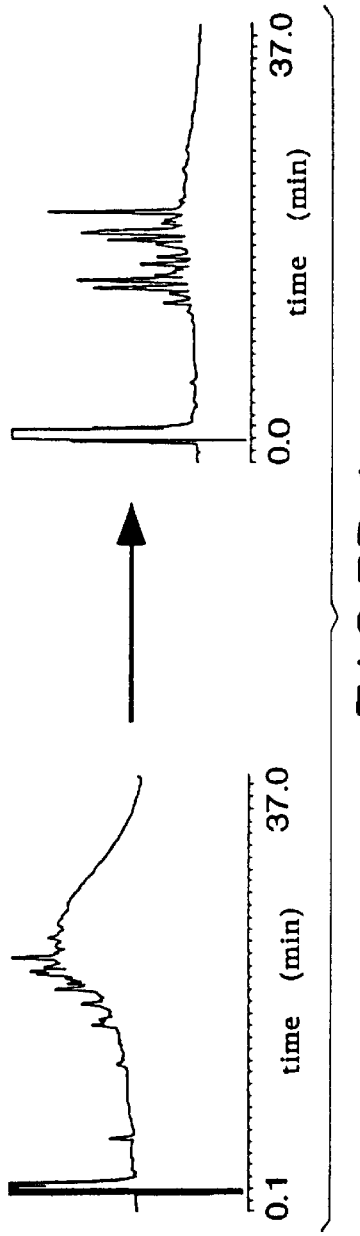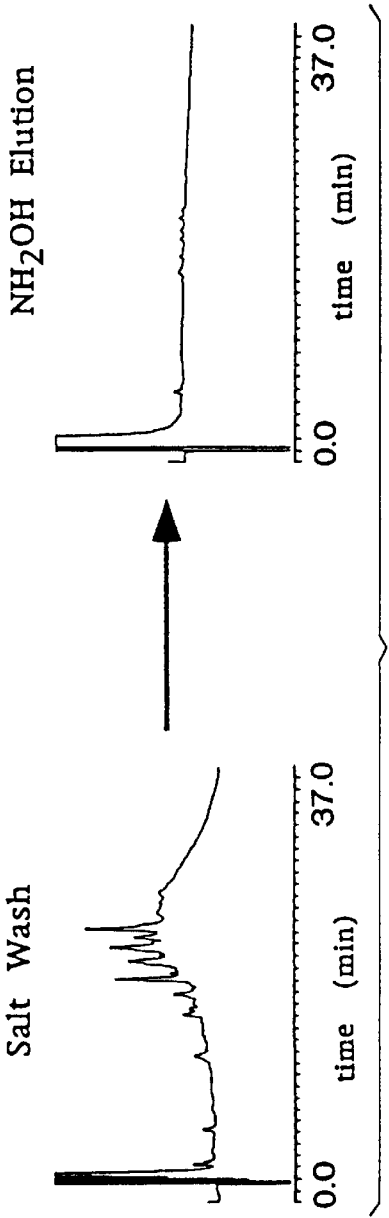
FIG. 3B-1
FIG. 3B-2

| C-terminal fragment (M+1)+ | N-terminal fragment (M+1)+ | |
| --- | --- | --- |
| 4279.9 | $G^{156}D^{157}$ | 2691.9 |
| 4166.8 | $D^{157}I^{158}$ | 2749.0 |
| 4053.6 | $I^{158}L^{159}$ | 2864.1 |
| 3897.4 | $L^{159}R^{160}$ | 2977.2 |
| 3784.3 | $R^{160}I^{161}$ | 3090.4 |
| 3628.1 | $I^{161}R^{162}$ | 3246.6 |
| 3513.0 | $R^{162}D^{163}$ | 3359.7 |
| 3384.8 | $D^{163}K^{164}$ | 3515.9 |
| 3287.7 | $K^{164}p^{165}$ | 3631.0 |

FIG.3C

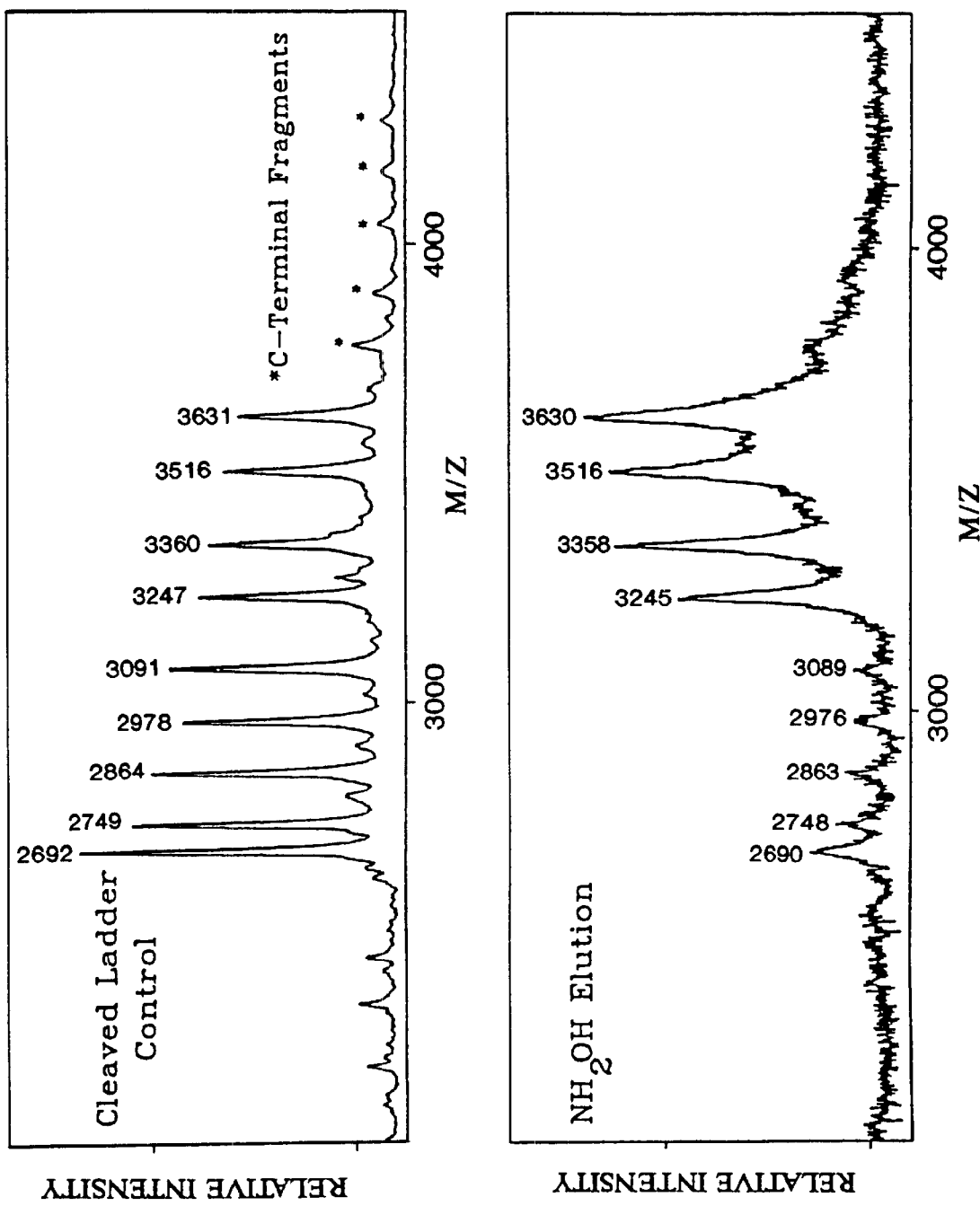
FIG.3D-1 Cleaved Ladder Control
FIG.3D-2 NH₂OH Elution

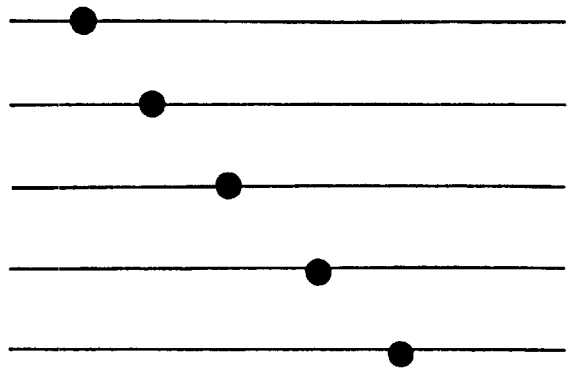
SCREENED FAMILY OF PEPTIDES EITHER BINDERS OR NONBINDERS
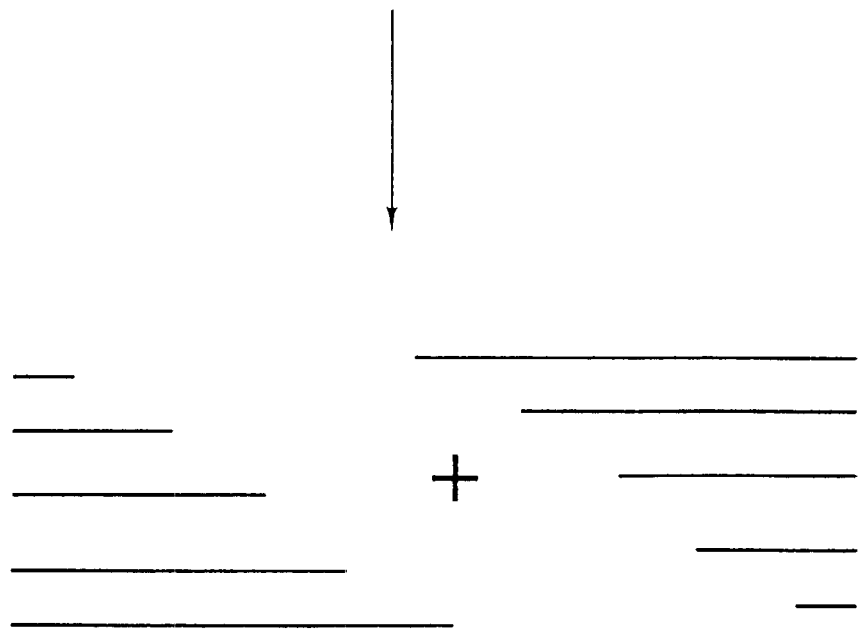
FIG. 7

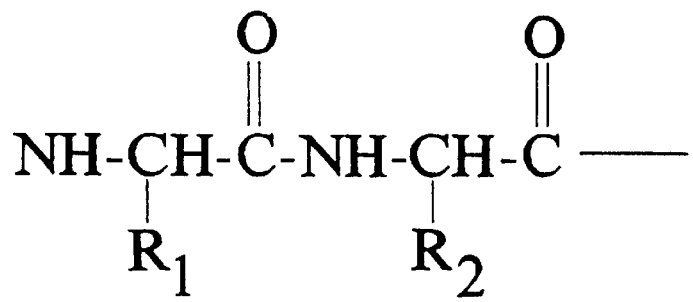
NATIVE
1 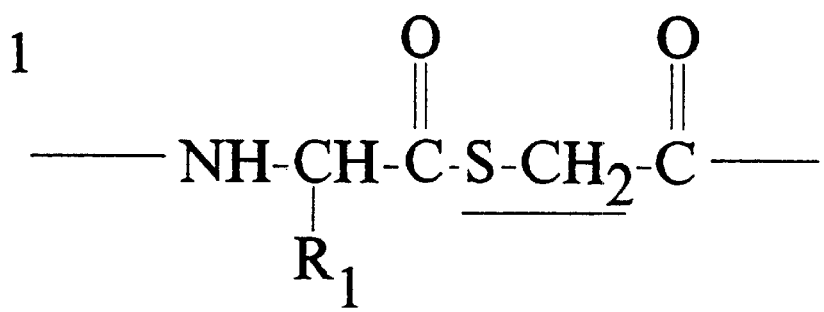
DELETE
1 SIDECHAIN
1 N-H
2 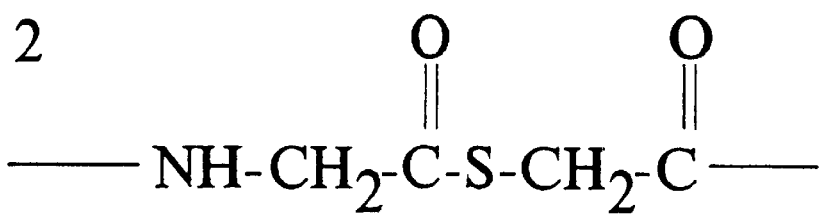
DELETE
2 SIDECHAIN
1 N-H
3 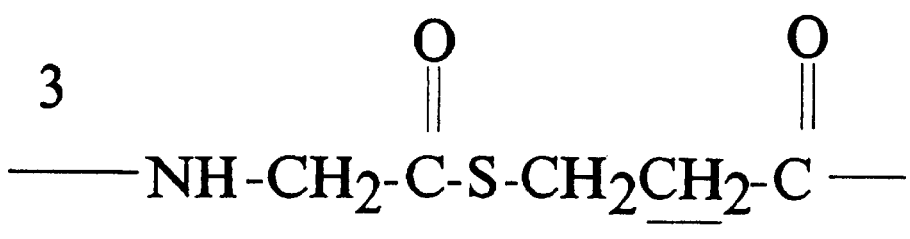
DELETE
2 SIDECHAIN
1 N-H
1 CH$_2$ IN
BACKBONE
FIG. II 1 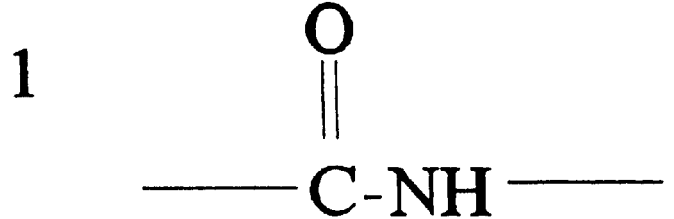
2 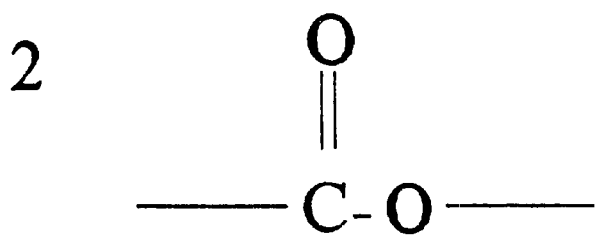
3 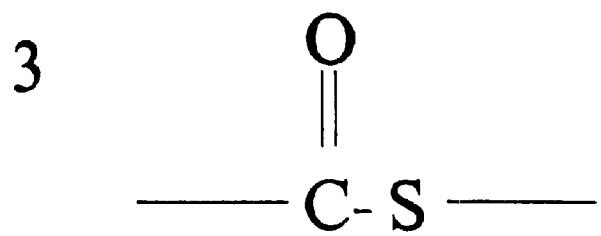
4 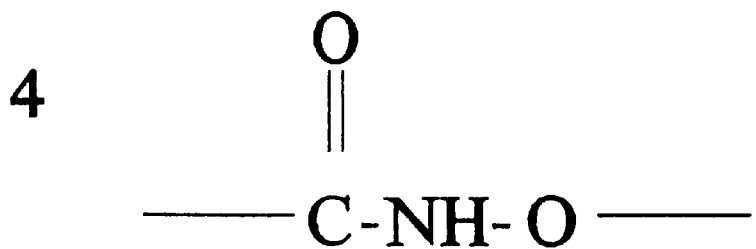
F I G. 12

22
↓

~~~-K-▷∑]  -I-L-R-I-R-D-K-P ~~~

~~~-K-G-▷∑] -L-R-I-R-D-K-P ~~~

~~~-K-G-D-▷∑] R-I-R-D-K-P ~~~

~~~-K-G-D-I ▷∑] -I-R-D-K-P ~~~

~~~-K-G-D-I-L ▷∑] R-D-K-P ~~~

~~~-K-G-D-I-L-R ▷∑] D-K-P ~~~

~~~-K-G-D-I-L-R-I▷∑] -K-P- ~~~

~~~-K-G-D-I-L-R-I-R▷∑] -P ~~~

~~~-K-G-D-I-L-R-I-R-D ▷∑] ~~~

F I G. 14

Parent peptide sequence: PFKK-[GDILRIRDKP]-EEAcpRLKLKAR

| Cycle# | A to 1 | Neutralize 1 | Couple AA$_n$ A , B | +BocGly- SβAla to 1 | DMF Wash A , B , 1' | 1' to B | +TFA A , B | 1 to 1' | DMF Wash A , B |
|---|---|---|---|---|---|---|---|---|---|
| 1) Pro$^{165}$ | 10mL -1mL | ✓ | ✓ | ✓ | ✓ | | ✓ | ✓ | ✓ |
| 2) Lys$^{164}$ | 9mL -1mL | ✓ | ✓ ✓ | ✓ | ✓ ✓ | ✓ | ✓ ✓ | ✓ | ✓ ✓ |
| 3) Asp$^{163}$ | 8mL -1mL | ✓ | ✓ ✓ | ✓ | ✓ ✓ ✓ | ✓ | ✓ ✓ | ✓ | ✓ ✓ |
| etc. | | | | | | | | | |
| 9) Asp$^{157}$ | 2mL -1mL | ✓ | ✓ ✓ | ✓ | ✓ ✓ ✓ | ✓ | ✓ ✓ | ✓ | ✓ ✓ |
| 10) Gly$^{156}$ | | | ✓ ✓ | | ✓ ✓ ✓ | ✓ | ✓ ✓ | | ✓ ✓ |

↓ 1 M Hydroxylamine
   20 minutes

1 M Hydroxylamine
20 minutes

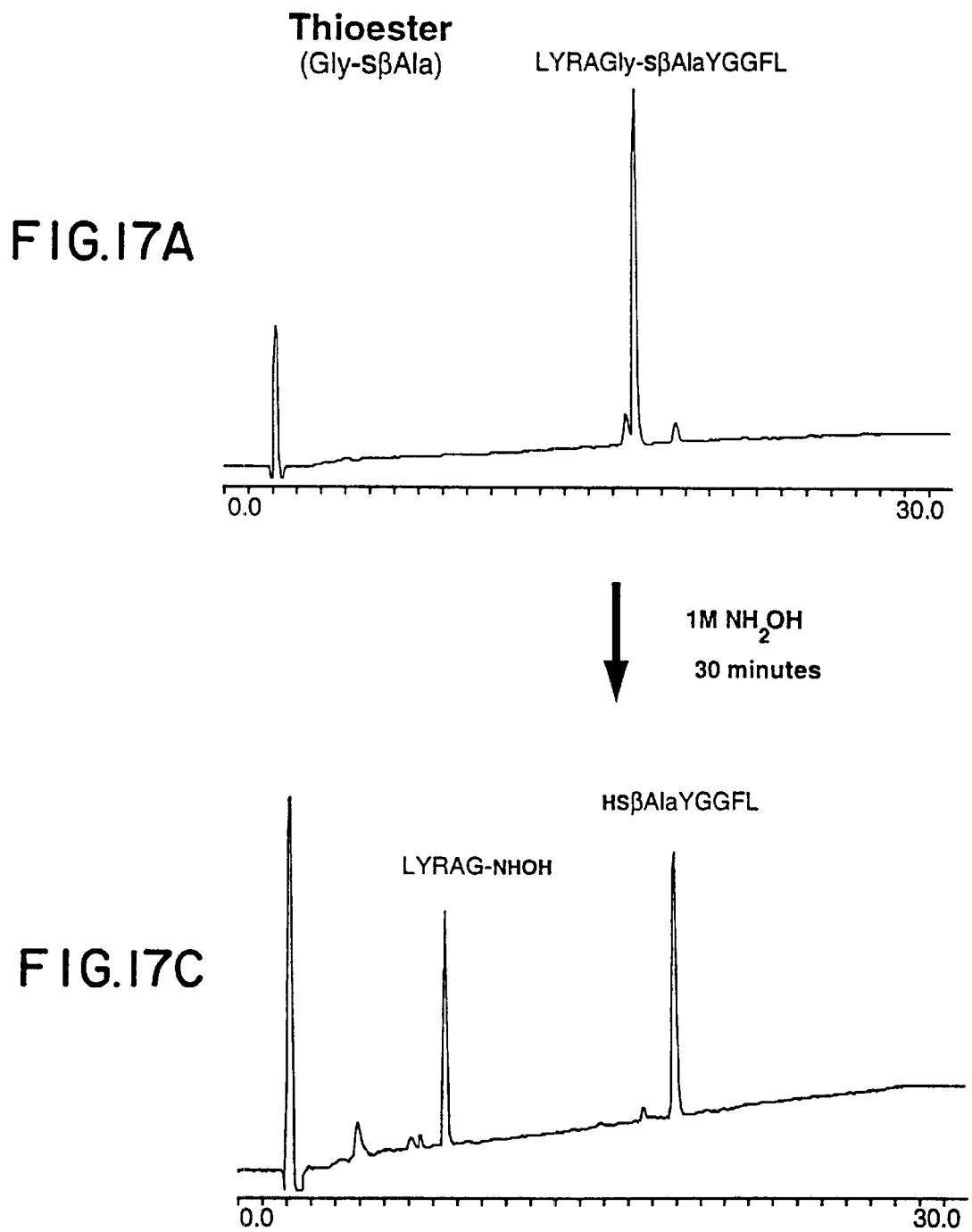

pH 10, [⁻OH]
6 hours

Array of Peptide Analogues

Chemical Cleavage

Cleaved Array of Peptide Analogues

Protein Analogue Array
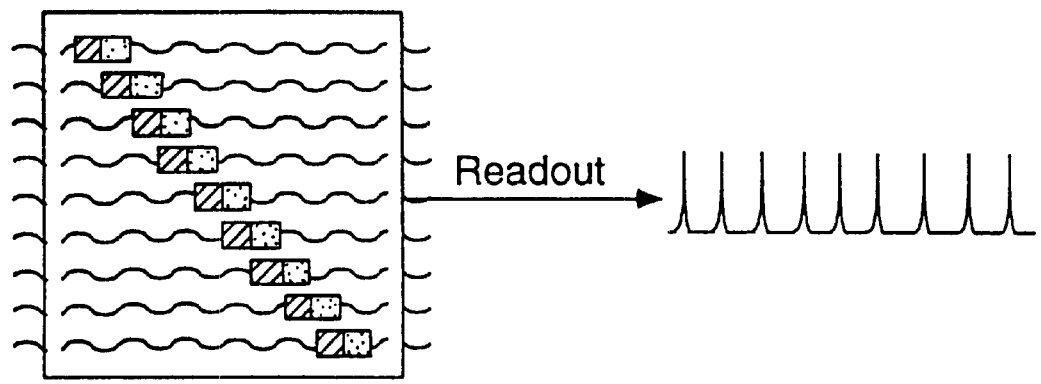
Functional Selection
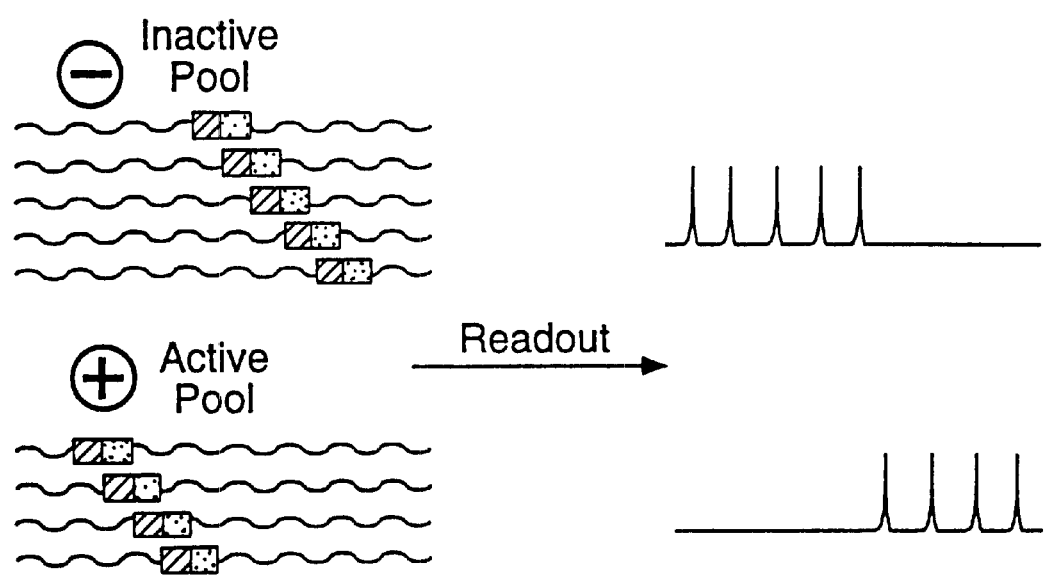
FIG. 21

FIG.22A
Native Dipeptide:
-NH-CH-CO-NH-CH-CO-
  |         |
  $R_1$     $R_2$
Gly-S-Gly:
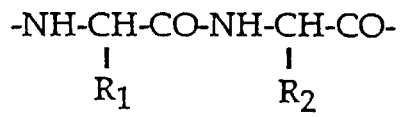
Gly-S-βAla:
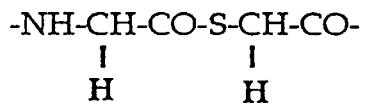
FIG.22B
Chemical Cleavage:
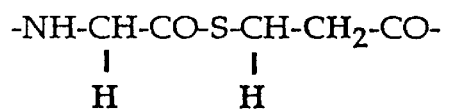
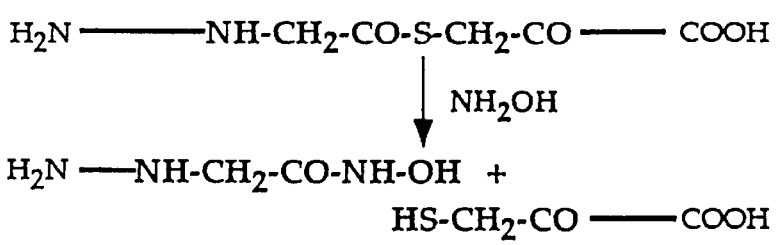

134　　　　146　　　　　　　　　　　165　　　　　　　　　　　　191
AEYVRALFDFNGNDEEDLPFKKGDILRIRDKPEEQWWNAEDSEGKRGMIPVPYVEKYR
FIG. 25A
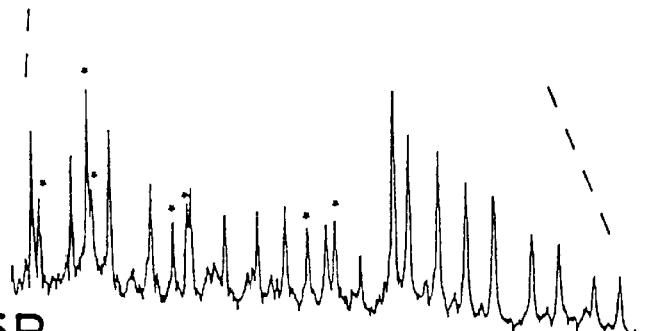
FIG. 25B
-Gly-[COS]-βAla- replaces:
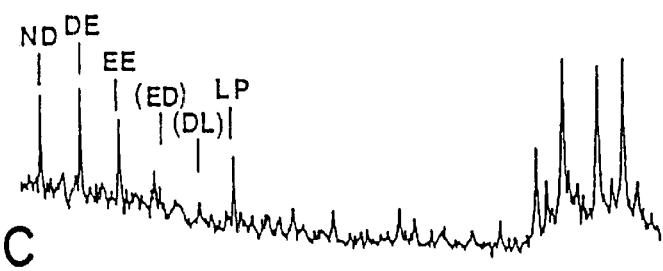
FIG. 25C 134                156         165                        191
AEYVRALFDFNGNDEEDLPFKKGDILRIRDKPEEQWWNAEDSEGKRGMIPVPYVEKYR analogue        GD
unit           |DI  IL
replaces:       |   |  LR  RI  IR  RD  DK
                       |   |   |   |   |  KP
                                           |

(control)

FIG. 26A

(wash)

FIG. 26B

(elution)

FIG. 26C

134           156         165                              191
AEYVRALFDFNGNDEEDLPFKKGDILRIRDKPEEQWWNAEDSEGKRGMIPVPYVEKYR analogue
unit
replaces:

-Gly-[COS]-Gly- (Binding pool)

-Gly-[COS]-βAla- (Binding pool)

PROCESS FOR CHARACTERIZING PROTEINS

This application is a 371 of PCT/US96/15516 (filed Sep. 27, 1996) and claims benefit of No. 60/004,563 (filed Sep. 29, 1995).

GOVERNMENT RIGHTS

This invention was made with government support under Contract Nos. GM 48870 and GM 48897 by the National Institutes of Health. The government has certain rights in the invention.

This invention was made with government support under Grants No. PO1GM 48870, HL31950, and RO1GM 48897 awarded by the National Institutes of Health. The U.S. government has certain rights in the invention.

TECHNICAL FIELD OF THE INVENTION

The present invention relates to methods for analyzing, altering, and controling the structural basis for protein binding to target molecules. More particularly, the present invention is directed to peptide ladder libraries corresponding to a protein, protein fragment, or other bioactive peptide and to the use of peptide ladder libraries for obtaining a protein signature analysis.

BACKGROUND OF THE INVENTION

One of the major strategies for determining the relationship between the chemical structure of a peptide and its biological activity is to systematically alter the covalent structure and observe the effect on function. Through the use of chemical synthesis, a wide variety of modifications can be made. For example, N-methylation and the use of ester bonds can probe backbone interactions (Arad et al. *Biopolymers* 1990, 29, 1633–1649; Bramson et al. *J. Biol. Chem.* 1985, 260, 15452–15457; Caporale et al. In: *Peptides: Structure and Function, Proceedings of the Tenth American Peptide Symposium*; Marshall, G. F. Ed. Escom:Leiden: The Netherlands, 1988, pp. 449–451), while sidechain contributions can be probed using D-amino acid or Alanine/Glycine substitutions (Konishi et al. In: *Peptides: Structure and Function, Proceedings of the Tenth American Peptide Symposium*, Marshall, G. F. Ed. Escom, Leiden: The Netherlands, 1988, pp. 479–481; Tam et al. In *Peptides:Proceedings of the Eleventh American Peptide Symposium*; Rivier, J. E.; Marshall, G. R. Ed.; Escom: Leiden, The Netherlands, 1990. pp 75–77). As traditionally practiced, a separate analogue must be prepared and assayed for each position in the peptide sequence that is to be studied.

An alternative, currently popular method of studying peptides is through combinatorial chemistry. This approach has had a major impact on the study of the molecular basis of peptide activity and has contributed to the search for new biologically active peptides (Thompson et al. *Chem. Rev.* 1996, 96, 555–600; Gordon et al. *J. Med. Chem.* 1994, 37, 1385–1401; Scott et al. *Curr. Op. Biotech* 1994, 5, 40–48) 'Multiple Peptide Synthesis' has extended the traditional approach by allowing peptides to be synthesized simultaneously (Geysen et al. *J. Proc. Natl. Acad. Sci. USA* 1984, 81, 3998–4001; Houghten et al. *Proc Natl. Acad. Sci. USA* 1985, 82, 5131–5134). The individual peptide products are spatially separated and can be analyzed either attached to a solid support or in solution. Established 'split synthesis' (Furka et al. *Int. J. Pept. Prot. Res.* 1991, 37, 487–494; Lam et al. *Nature* 1991, 354, 82–84) procedures allow for the rapid generation of huge numbers of peptide sequences through the repetition of a simple divide, couple and recombine process. The compositional diversity made possible by this approach is advantageous for the discovery of new 'lead' compounds since, in principle, all possible structural variants can be explored for the desired activity and only the few active oligomers of interest need to be individually identified (Furka et al. *Int. J. Pept. Prot. Res.* 1991, 37, 487–494; Lam et al. *Nature* 1991, 354, 82–84). However, where information about a complete set of functional and non-functional components is desired over many positions in a peptide sequence, such libraries are too complex to fully characterize and may have limited utility.

A more systematic investigation of the molecular basis of peptide function requires a different type of molecular diversity. Instead of a peptide mixture of high compositional diversity, it would be useful to construct an array of peptides which differ from each other in a precise and defined manner. In principle, one way to access this population would be as a minor fraction of a large, fully combinatorial library. For example, such an array of analogues could consist of all peptides which differ from a target sequence by a single amino acid substitution at each position in a peptide sequence (cf. 'Ala scans'). By removing this defined subset of analogues from the context of a complex, fully combinatorial mixture of peptides, handling and analysis would be greatly simplified and a more useful profile of the effects of substituting the amino acid throughout the peptide chain would be obtained. Current split resin methods do not allow for this type of control over the composition of a peptide library. (Furka et al. *Int. J. Pept. Prot. Res.* 1991, 37, 487–494; Lam et al. *Nature* 1991, 354, 82–84).

Typically, to investigate the molecular basis of protein function systematic modifications are made to the protein structure and the effects of those modifications on the properties of the protein are evaluated. Site-directed mutagenesis (Smith et al. *Angew. Chem. Int. Ed. Engl.* 1994, 33, 1214–1220) has been the principle tool used to implement this approach and has given many insights into the contribution of individual sidechains to protein function. In particular, 'alanine scanning' (Wells et al. *Methods in Enzymology* 1991, 202, 390–411) has been used to identify specific amino acid sidechains involved in ligand binding interactions. This technique involves the sequential substitution of native amino acids by individual alanine residues which are regarded as functionally and structurally neutral. To extend the repertoire of modifications beyond the twenty genetically encoded amino acids, methods have been developed to substitute non-natural groups into proteins (Noren et al. *Science.* 1989. 244, 182–185). Although a variety of both novel sidechain and backbone modified proteins have been generated, there are apparent limits to the modifications possible using the methods of molecular biology and ribosomal synthesis (Ellman et al. *Science* 1991, 255, 197–200; Cornish et al. *Angew Chem Int. Ed. Engl.* 1995, 34, 621–633).

Recent advances in the total synthesis of polypeptides have opened the world of proteins to direct application of the tools of organic chemistry (Schnölzer et al. *Science* 1992, 256, 221–225; Jackson et al. *Science* 1994, 266, 243–247; Dawson et al *Science* 1994, 266, 776–779; Canne et al. *J. Am. Chem. Soc.* 1995, 117, 2998–3007; Liu et al *J. Am. Chem. Soc.* 1995. 118, 307–312; Englebretsen et al. *Tet. Lett.* 1995, 36, 8871–8874). Using total chemical synthesis, a variety of protein analogues has been synthesized. Of particular note have been proteins containing β-turn mimics (Baca et al. *Prot. Sci.* 1993, 2, 1085–1091), N-methylated amino acids (Rajarathnam et al. *Science* 1994, 264, 90–92), modified backbone atoms (Baca et al *J. Am. Chem. Soc.* 1995, 117, 1881–1887), and mirror image proteins composed entirely of D-amino acids (Zawadzke et al. *J. Am. Chem. Soc.* 1992, 114, 4002–4003; Milton et al. *Science* 1992, 256, 1445–1448; Fitzgerald et al. *J. Am. Chem. Soc.* 1995, 117, 11075–11080; Schumaacher et al. *Science* 1996, 271, 1854–1857). In addition, important insights into the mechanism of action of enzymes have been attained through the total chemical synthesis of unique analogues (Baca et al. *Proc. Natl. Acad. Sci. U.S.A.* 1993, 90, 11638–11642).

Although structure-function relationships in proteins can be studied using individual analogues prepared by either recombinant or chemical techniques, development of a profile of effects across the whole protein molecule is hindered by the time and effort required to generate and analyze multiple protein analogues (Matthews et al. *Ann. Rev. Biochem.* 1993, 62, 139–160). The use of combinatorial oligonucleotide synthesis in conjunction with protein expression in bacteria (Reidhaar-Olsen et al. *Science* 1988, 241, 53–57; Gregoret et al. *Proc. Natl. Acad. Sci. USA.* 1993. 90. 4246–4250) or on phage (Scott et al. *Science* 1990, 249, 386–390; Lowman, H. B. Bass, S. H.; Simpson, N.; Wells, J. A. *Biochemistry* 1991. 30 10832–10838) has provided a powerful method for studying large numbers of analogue proteins. These techniques allow pools of expressed proteins to be probed for a desired function. With appropriate screening procedures, a statistical sampling of numerous functional protein variants can be analyzed and identified (Gu et al. *Protetin Science* 1995, 4, 1108–1117). This strategy has proved to be powerful for generating variant proteins with new or optimized functions (Lowman et al. *J. Moll. Biol.* 1993, 234, 564–578; Rebar et al. *Science* 1994, 263, 671–673). However, studies designed to elucidate the molecular basis of protein function have been complicated by the necessarily incomplete characterization of the numerous protein analogues generated, and also by limitation to the naturally encoded amino acids.

In applying molecular diversity to the study protein function it would be useful to combine the valuable information gained by systematic modification through chemical synthesis with the advantages of combinatorial methods.

What is needed is an integrated approach to the preparation of a defined array of peptide and protein analogues in a single synthesis, their functional separation into active and inactive pools, and a simple one step readout of the composition of the self-encoded mixtures.

SUMMARY OF THE INVENTION

There are three aspects to the invention:
1. A combinatorial method for synthesizing a peptide ladder library corresponding to a protein, protein fragment, or other bioactive peptide.
2. A method for screening the peptide ladder library with respect to a binding function.
3. A method for identifying active or inactive components of the peptide ladder library, i.e. identification of a protein signature for the protein or protein fragment under investigation with respect to the function being probed.

A combinatorial synthetic method for making a peptide ladder library is illustrated in FIG. 1. The peptide ladder library is a one pot collection of "n" peptides, each peptide being identical to the others in the library with respect to molarity and structure except for the substitution of a marker at position "n". The marker introduces a labile bond into the peptide backbone, e.g. a thioester bond, which can be selectively cleaved without cleaving other bonds within the peptide backbone. The marker also serves to introduce a ladder of stearic perturbations into the peptide backbone and/or to introduce a ladder of peptide side chain substitutions. The synthetic protocol employs a split synthesis method.

Conventional screening methods may be employed on the peptide ladder library to separate active components from inactive components within the library. An exemplary screening protocol is illustrated in FIG. 2.

After the screening is complete, the isolated components are analyzed as illustrated in FIG. 3 to obtain a molecular signature for the protein. Briefly, the isolated components are cleaved at their marker and analyzed. Mass spectrometry is the preferred method of analysis. However, alternative analytical methods include nmr (with deuterium exchange), ir, and FACS. Comparison of the analysis, e.g., ms, of the isolate with the control, i.e., an aliquot of the entire library, provides a molecular signature which identifies sites within the protein responsive or unresponsive to the screening method. For example, sites within the protein essential for binding or folding may be identified. The protein signature of the Crk-N/C3G interaction is illustrated in FIG. 3.

Successive iterations of the method of the invention can be employed to obtain a complete deconstructive analysis of a protein, even if the structure of the protein is unknown. The invention may be employed to characterize protein interactions and can facilitate the design of new therapeutics which are dependent upon such protein interaction.

One aspect of the invention is directed to a method for obtaining a molecular signature of a protein. The protein is of a type which has an amino acid sequence with length m, each amino acid position being represented by $(aa)_n$ where $1 \leq n \leq m$. The protein is also of a type which has a binding affinity with respect to a target molecule under binding conditions. The molecular signature then defined by a subsequence of the amino acid sequence of the protein. The subsequence is selected from amongst those positions $(aa)_n$ of the protein which, if individually replaced by a substitute amino acid, lead to a loss of binding affinity by the protein with respect to the target molecule.

The method employs a peptide ladder library. The peptide ladder library has m peptides. Each of the peptides is represented by $(peptide)_n$, where $1 \leq n \leq m$. Each peptide has the same amino acid sequence as the protein except that position $(aa)_n$ of $(peptide)_n$ is replaced by a substitute amino acid. Preferred substitute amino acids include alanine and glycine. If only one substitute amino acid is employed, then the peptide has a footprint the size of one amino acid. In alternative embodiments, the footprint may include two or three substitute amino acids. The substitute amino acid at position $(aa)_n$ is linked to the amino acid at position $(aa)_{n+1}$ by means of a labile bond. Preferred labile bonds are thioester bonds and ester bonds.

The peptide ladder library is then contacted with the target molecule under binding conditions in order to form bound peptides and unbound peptides. The bound peptides are bound to the target molecule; the unbound peptides are not. The unbound peptides are then separated from the bound peptides from said Step B in order to obtain separated unbound peptides. Each of the separated unbound peptide has the substitute amino acid only at position $(aa)_n$ which constitute the subsequence that define the molecular signature of the protein with respect to the target molecule. The labile bond of the separated unbound peptides are then cleaved in order to produce peptide cleavage products. Each peptide cleave product corresponds to one of the positions (aa)$_n$ from the subsequence which defines the molecular signature. The subsequence which defines the molecular signature of the protein is then constructed using the identity of the peptide cleavage products to identify the subsequence of amino acid positions that are essential for binding to the target molecule.

Alternative substitute amino acids include the following: L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine, D-alanine, D-arginine, D-aspartic acid, D-asparagine, D-cysteine, D-cystine, D-glutamic acid, D-glutamine, D-glycine, D-histidine, D-isoleucine, D-leucine, D-lysine, D-methionine, D-phenylalanine, D-proline, D-serine, D-threonine, D-tryptophan, D-tyrosine, D-valine, L-α-aminobutyric acid, D-α-aminobutyric acid, L-γ-aminobutyric acid, D-γ-aminobutyric acid, L-ε-aminocaproic acid, D-ε-aminocaproic acid, L-homophenylalanine, D-homophenylalanine, L-alloisoleucine, D-alloisoleucine, L-β-2-napthylalanine, D-β-2-napthylalanine, L-norvaline, D-norvaline, L-ornithine, D-ornithine, L-pyridyl alanine, D-pyridyl alanine, L-2-thienylalanine, D-2-thienylalanine, L-methyltyrosine, D-methyltyrosine, L-citrulline, D-citrulline, L-homocitrulline, and D-homocitrulline.

In an alternative mode, the molecular signature of the protein is determined as described above except that the analysis is performed on the bound peptides are separated from the unbound peptides. Each of the separated bound peptides lacks any substitute amino acid at position (aa)$_n$ from the subsequence which defines the molecular signature of the protein. The labile bonds of the separated bound peptides are then cleaved to form peptide cleavage products. Each peptide cleave product corresponds to one of the positions (aa)$_n$ not included within the subsequence which defines the molecular signature. Accordingly, in this mode of the invention, after detecting and identifying each of the peptide cleavage products, the subsequence which defines the molecular signature of the protein with respect to the target molecule is constructed by identifying amino acid positions (aa)$_n$ which does not correspond to any of the peptide cleavage products.

Another aspect of the invention is directed to a peptide ladder library corresponding to a protein. The protein is of a type which has a binding affinity with respect to a target molecule under binding conditions. The protein is also of a type which has an amino acid sequence with length m where $1 \leq n \leq m$. Each amino acid position within the protein is represented by (aa)$_n$. The peptide ladder library then comprises m peptides, each peptide being represented by (peptide)$_n$, where $1 \leq n \leq m$. Each peptide within the library has the same amino acid sequence as the protein except that position (aa)$_n$ of (peptide)$_n$ is replaced by a substitute amino acid. The substitute amino acid at position (aa)$_n$ is linked to the amino acid at position (aa)$_{n+1}$ by means of a labile bond. If only one substitute amino acid is employed, then the peptide has a footprint the size of one amino acid. In alternative embodiments, the footprint may include two or three substitute amino acids. Preferred labile bonds include thioesters and esters. Preferred substitute amino acids are alanine and glycine.

Another aspect of the invention is directed to a method for constructing a peptide ladder library corresponding to a protein. The protein is of a type which has an amino acid sequence with length m. Each amino acid position of the protein may be represented by (aa)$_n$ where $1 \leq n \leq m$. The peptide library includes m peptides. Each peptide may be represented by (peptide)$_n$, where $1 \leq n \leq m$. Each peptide has the same amino acid sequence as the protein except that position (aa)$_n$ of (peptide)$_n$ is replaced by a substitute amino acid. The substitute amino acid at position (aa)$_n$ is linked to the amino acid at position (aa)$_{n+1}$ by means of a labile bond. A first reaction vessel may be provided which contains a first pool of nascent peptides having a length of m−n. The amino acid sequence of the nascent peptides runs between n+1 and m of the protein. The nascent peptides are attached to a matrix material. A second reaction vessel may be provided which contains a first pool of nascent ladder peptides having a length of m−n. The amino acid sequence runs between n+1 and m of the protein except that each (nascent ladder peptide)$_p$ has the substitute amino acid at position (aa)$_p$, where $n+1 \leq p \leq m$. The nascent ladder peptides are attached to a matrix material. An aliquot of matrix material is then transferred from the first reaction vessel to a third reaction vessel. Elongation reactions are then performed in each of the three reaction vessels. The first pool of nascent peptides in the first reaction vessel is elongated by addition of the amino acid of position (aa)$_n$ to form a second pool of nascent peptides having a length of m−n+1; the aliquot of nascent peptides in the third reaction vessel is then elongated by addition of the substitute amino acid of position (aa)$_n$ by means of labile bond to form a nascent ladder (peptide)$_n$ having a length of m−n+1; and the first pool of nascent peptide ladders in the third reaction vessel is elongated by addition of the amino acid of position (aa)$_n$ to form a partial second pool of nascent peptide ladders having a length of m−n+1. After the elongation reactions are complete, the product of the third reaction vessel is transferred to the second reaction vessel to complete the second pool of nascent peptide ladders having a length of m−n+1. The above process may then be repeated until n=1 and the second reaction vessel contains the sought after peptide ladder library.

DESCRIPTION OF FIGURES

FIG. 7 illustrates the readout step "unzipping the peptide" which reveals the latent chemistry.

FIG. 11 illustrates the scanning of a marker which introduces a labile bond into the peptide backbone. The labile bond can then be selectively cleaved without claving other bonds within the peptide backbone. The marker also serves to introduce a ladder of steric perturbations into the peptide backbone and/or introduce side chain substitutions.

FIG. 12 illustrates a representative sample of the readout chemistry to introduce a labile bond into the peptide.

FIG. 14 illustrates an example of a peptide ladder library corresponding to a protein fragment of the SH-3 domain with the sequence (SEQ ID Nos 1 and 26–36) -KGDILRIRDKP-.

FIG. 21 illustrates an integrated strategy for the chemical synthesis, functional separation, and analysis of a self-encoded array of protein analogues. The array of protein analogues is prepared by total chemical synthesis in a single procedure. Each analogue unit contains a selectively cleavable bond. Site-specific cleavage yields fragments that identify each protein component and define the position of the analogue unit within the polypeptide chain. This decoding procedure is applied to the parent array of analogues, and to the active and inactive pools after separation based on function.

FIG. 22 illustrates chemical Structures of Analogue Units A. Comparison of a native dipeptide unit (top) with the structures of the Gly-[COS]-Gly (middle) and Gly-[COS]-βAla (bottom) analogue units used in the present study. B. Chemical cleavage of the thioester bond within the analogue unit can be carried out selecively under mild conditions by treatment with hydroxylamine at neutral pH. The thioester bond is stable to the conditions normally used to study proteins.

FIG. 23 illustrates a readout of the composition of an array of analogues of the cCrk N-terminal SH3 domain. A. The array consists of nine sub populations, each containing a single Gly-SβAla analogue unit. The dipeptide analogue was placed in consecutive positions along the polypeptide chain, resulting in an overlapping pattern of substitution. B. Chemical cleavage of the thioester bond in the analogue unit results in an array of peptide fragments that characterizes the composition of the mixture of parent protein analogues. C. The array of peptide fragments can be read out in one step by matrix assisted laser desorption time of flight mass spectrometry (MALDI-TOF). The resulting pattern of date is illustrated here for the C-terminal containing family of fragments (SEQ ID NOs 26–36).

FIG. 25 illustrates an application of protein signature analysis to a twenty residue region of the N-terminal SH3 domain of murine c-Crk. A. The highlighted amino acid sequence (residues 146–165) was substituted by the dipeptide analogue Gly-[COS]βAla, giving a 19-member array of synthetic analogue proteins. B. Signature obtained for the parent array, after cleavage with neutral hydroxylamine and analysis by MALDI mass spectrometry. Only the family of N-terminal fragments was observed in the spectrum. The C-terminal fragments, although necessarily present, are not visible under the MALDI conditions used [Several terminated peptides, arising from impurities in the commercial amino acids used, are marked with an asterisk (*)]. C. Signature of the active (binding) pool eluted from the C3G-derived synthetic peptide affinity column. Eight of the protein analogues displayed appreciable binding under these conditions, showing that dipeptide sequences $N^{146}D^{147}$; $D^{147}E^{148}$; $E^{148}E^{149}$; $L^{151}P^{152}$; $I^{161}R^{162}$; $R^{162}D^{163}$; $D^{163}K^{164}$; and, $K^{164}P^{165}$ could be replaced by the dipeptide analogue without significant loss of activity. [Dipeptide sequences in parentheses, viz. '(ED)' & '(DL)', indicates the notable Gly-[COS]-βAla-containing protein analogues not showing significant binding activity] (SEQ ID NO 37).

FIG. 26 illustrates a readout of the composition of the parent nine component cCrk SH3 domain array, and the binding and non-binding pools. The cCrk SH3 domain array of protein analogues was folded in assay buffer and added to a C3G peptide affinity column. Column fractions were treated with hydroxylamine and then analyzed by MALDI mass spectrometry. A. (control) Composition of the parent array of cCrk SH3 domain analogues. B. (Wash) Non-binding cCrk SH3 domain analogues eluted in the 0.5 M NaCl wash. C. (Elution) Specifically-bound cCrk SH3 domain analogues eluted with hydroxylamine. MALDI peaks are marked by the single letter code for the dipeptide that had been was substituted with Gly-SβAla (SEQ ID NO 37).

DETAILED DESCRIPTION OF THE INVENTION

The invention is directed to a 3 step methodology, titled Protein Signature analysis, for the identification of active or inactive components of a protein. The first step involves a combinatorial method for synthesizing a peptide ladder library corresponding to a protein, protein fragment, or other bioactive peptide. The second step comprises a method for screening the peptide ladder library with respect to a binding function. The third step comprises a method for identifying active or inactive components of the peptide. Successive iterations of the method can be employed to obtain a complete deconstructive analysis of a protein, even if the structure of the protein is unknown. The invention may be employed to characterize protein interactions and can facilitate the design of new therapeutics which are dependent upon such protein interaction.

The methodology combines the control of peptide composition provided by multiple synthesis of individual peptides with the synthetic convenience of a split and recombine synthetic strategy. By synthesizing an array of peptides which differ from a parent molecule by a limited number of defined modifications, the contribution of specific molecular features to peptide function can be probed in a systematic manner.

The methodology further comprises a novel encoding scheme which allows for the array of synthetic peptide analogues to be assayed free in solution. The composition of the peptide mixture can then be determined by a single readout operation.

The methodology was used to synthesize an array of peptide analogues in which a specific modification was systematically incorporated into unique positions in a peptide sequence (examples 1,2 and 3 infra). The synthesis was carried out in such a way that the resulting mixture contained a defined family of modified peptides, with each peptide molecule containing only a single modification. The position of the analogue moiety within each member of the array was self-encoded by incorporating a selectively cleavable bond into the analogue structure.

The synthetic polypeptide array was folded and analyzed for ligand binding on an affinity column as a single mixture, producing two separate binding and non-binding pools of protein analogues.

Following selective cleavage of each polypeptide chain at the site of modification, the resulting mixture of peptide fragments (either the binding or non binding pool) was analyzed by MALDI mass spectrometry to generate patterns of data which defined the presence or absence of each peptide analogue in the ligand binding and non-binding pools. This mass spectrometric signature related the position of the chemical modification in the polypeptide sequence to the ability to fold and/or bind to a specific ligand for the protein (examples 1,2 and 3, infra).

EXAMPLE 1

(Illustrates Chemical Synthesis and Readout of Self Encoded Arrays of Peptide Analogues—Functional Separation Step is not Included Here)

Figure 4:
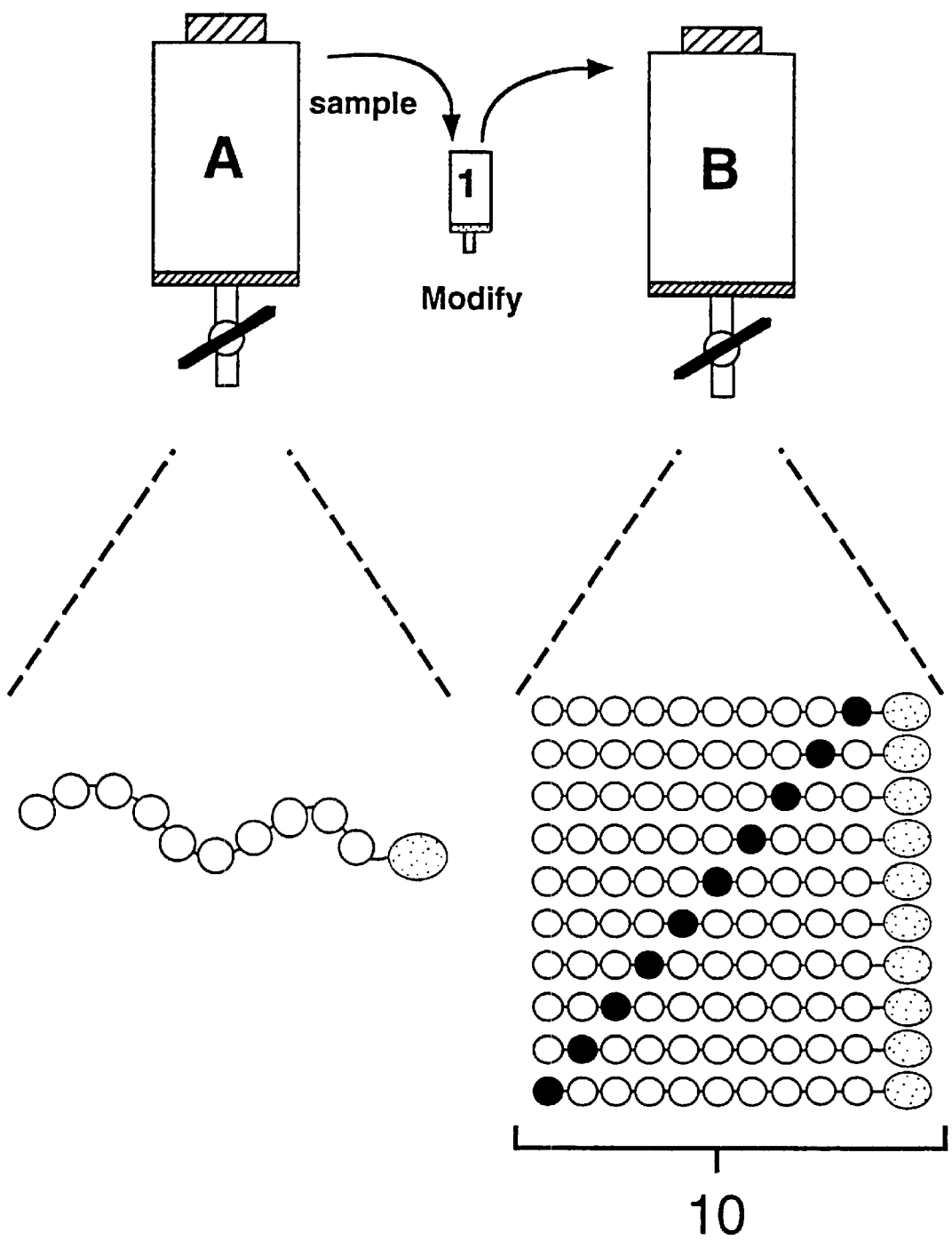
FIG. 4 illustrates the basic strategy for the synthesis of defined arrays of peptide analogues. The general approach is to have two main reaction vessels, one for unmodified peptide-resin, A, and the other for modified peptide-resin, B. Standard stepwise solid phase peptide synthesis of the parent amino acid sequence is performed in vessels A and B. Modifications to the sequence are made in a single auxiliary vessel, 1. At the beginning of each step in which introduction of an analogue structure is desired, a sample of peptide-resin is transferred from A to 1, where it is modified and then transferred from 1 to B after completion of that cycle of synthesis in both A and B.
Figure 5:
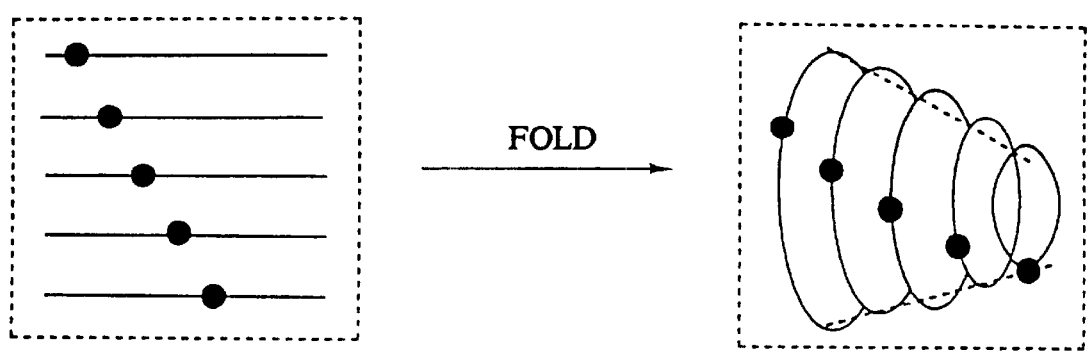
FIG. 5 illustrates the folding step for a family of peptides.
Figure 6:
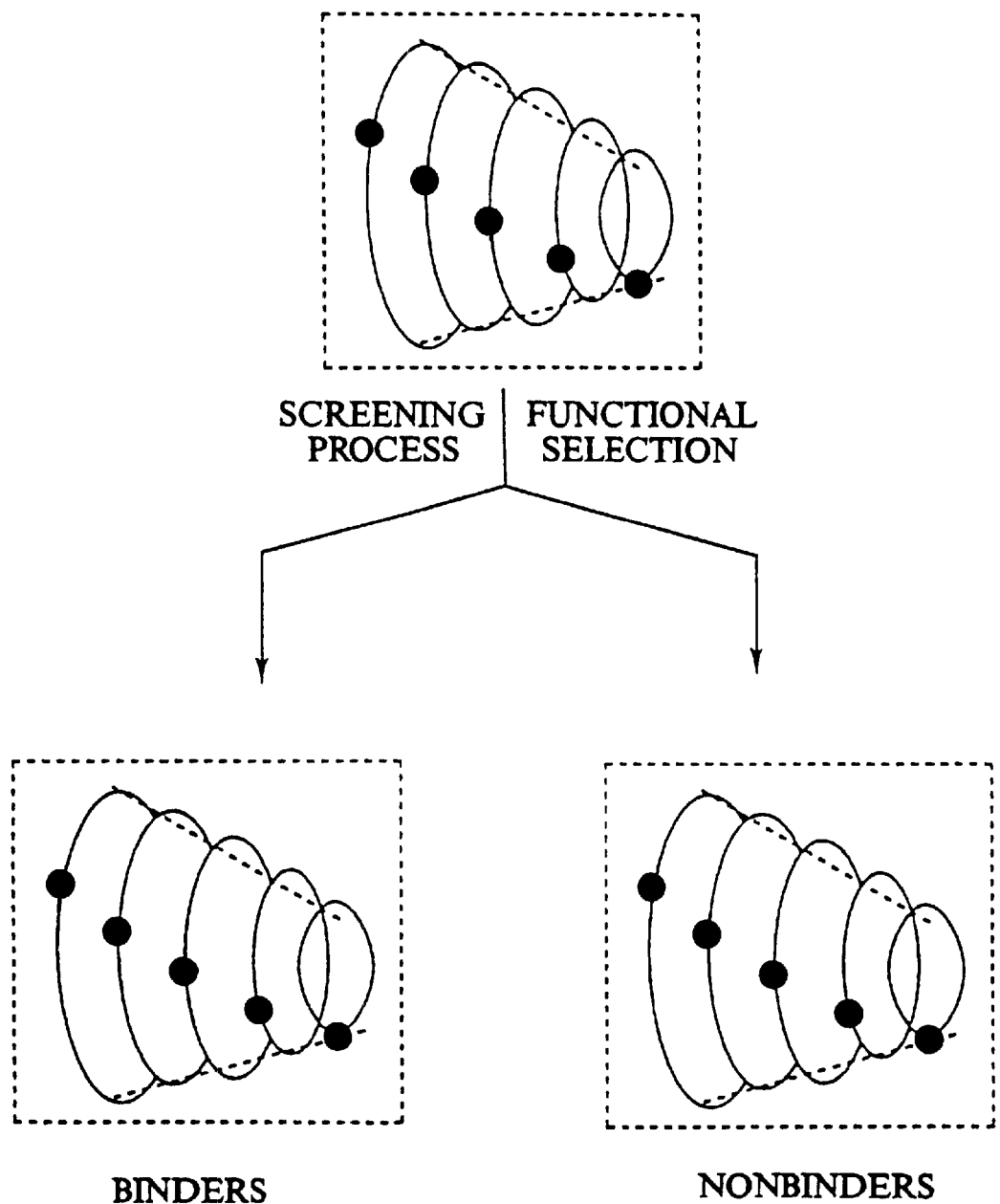
FIG. 6 illustrates the screening method of the peptide ladder library with respect to binding function.
Figure 8:
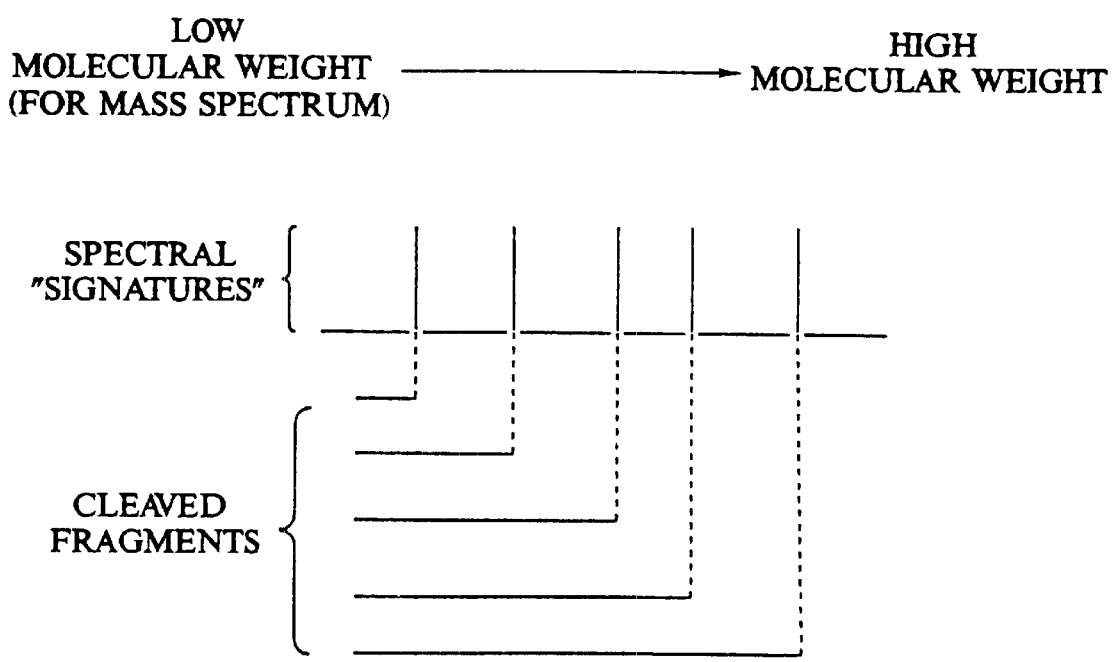
FIG. 8 illustrates an anlaysis of components using mass spectroscopy, nuclear magentic resonance, HPLC, IR or FACS.
Figure 9:
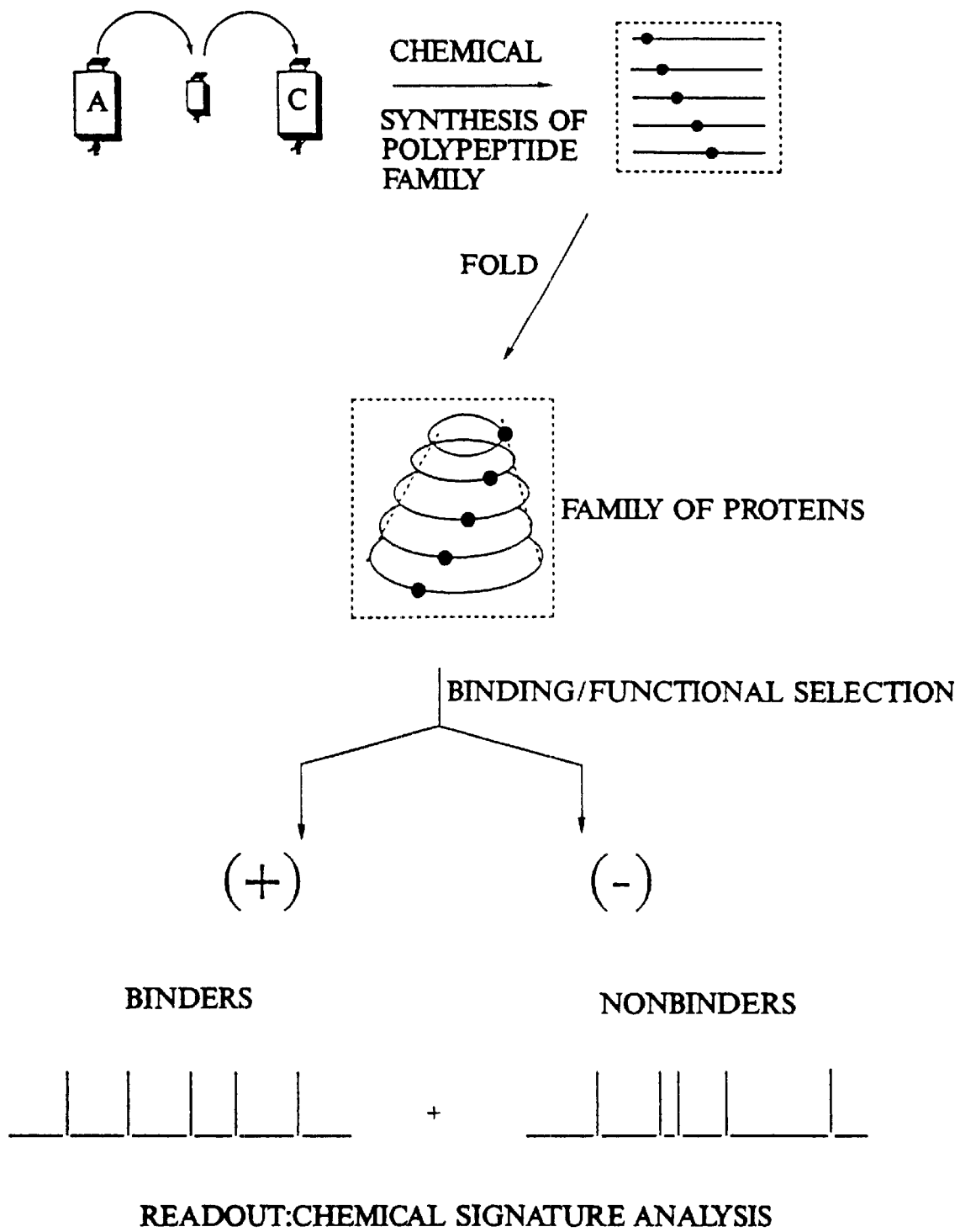
FIG. 9 illustrates the process of the molecular signature analysis.
Figure 10:
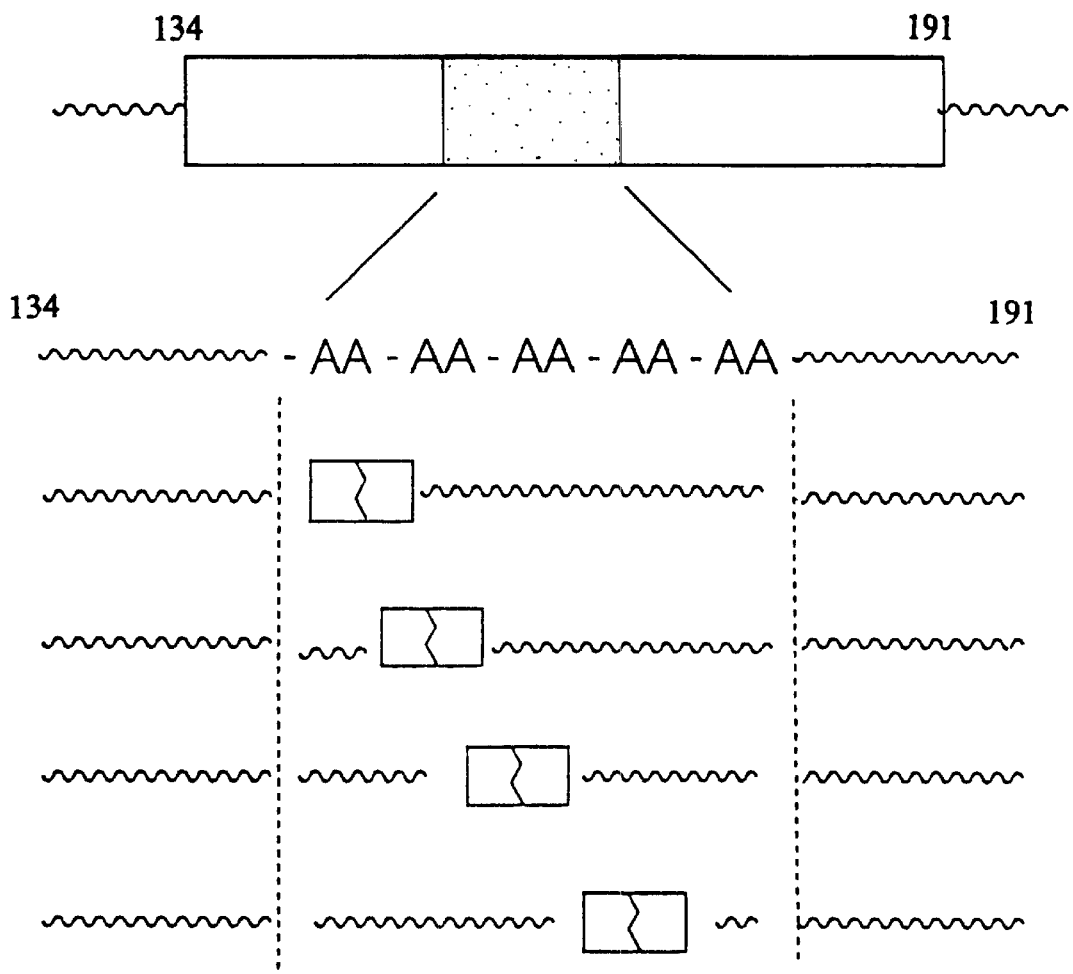
FIG. 10 illustrates the design of a peptide ladder from the peptide sequence of a protein, protein fragment of bioactive peptide.
Figure 13:
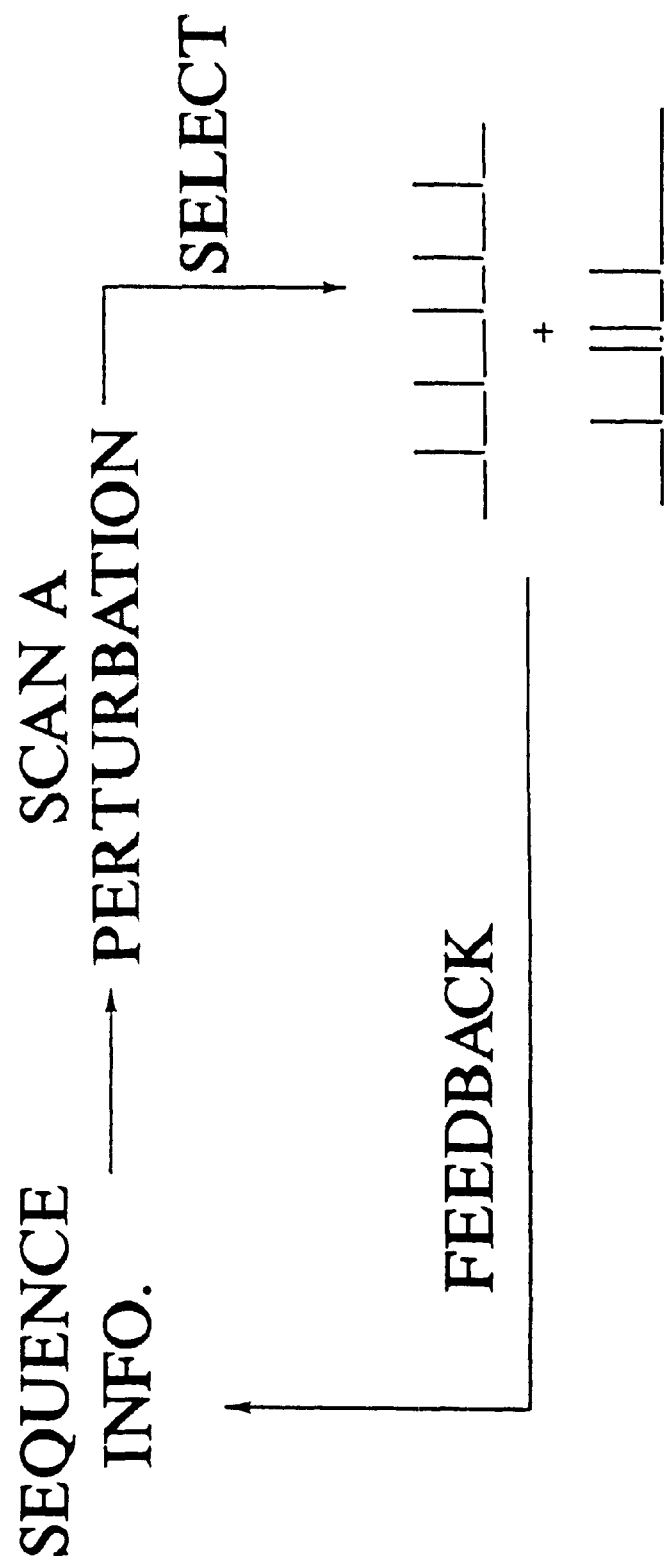
FIG. 13 illustrates a process which comprises the use of iterative steps as needed. The steps can be generally organized as 1) sequence info. 2) scan a perturbation 3) selection and 4) feedback.

A. Strategy for the Preparation of a Defined Array of Peptide Analogues as Illustrated in FIG. 4

A peptide analogue array for use with the proposed self-encoding scheme has two important features. First, the components of the array must be present in approximately equimolar amounts. Second, to avoid ambiguities, the array should consist only of peptides containing a single chemical modification per peptide chain, at a defined number of positions in the sequence. A straightforward procedure for synthesizing an array of this type has been developed and is schematically represented in FIG. 4. For simplicity, the procedure will be illustrated for a hypothetical array of peptides consisting of substitutions of a single amino acid analogue at each of ten consecutive positions in the amino acid sequence of the parent peptide.

Two manual solid phase peptide synthesis (SPPS) reaction vessels, A and B, and a small fritted funnel, 1, are used to manipulate the peptide-resin. The synthesis begins with ten units of peptide-resin in vessel A. After deprotection of the α-amino group, one unit of peptide-resin is removed from A and added to 1. The first amino acid is then coupled to the nine units of peptide-resin in A and the analogue moiety to the one unit peptide-resin sample in 1. After the coupling step, the analogue-modified peptide-resin from 1 is transferred to B.

To initiate the next cycle of synthesis, the peptide-resin in vessels A and B are deprotected. Then another unit of peptide-resin is removed from A and transferred to the now empty 1. The next amino acid in the sequence of the parent peptide is added in activated form to both A and B, while the analogue moiety is reacted with the new peptide-resin sample in 1. After completion of this cycle, the modified peptide-resin in 1 is added to B. The synthesis continues in this manner for the requisite ten cycles.

Throughout the synthesis, vessel A contains only unmodified peptide-resin. Vessel B contains all single-site modified peptide-resins and vessel 1 contains the current sample of peptide-resin which is being modified. All chemical steps carried out in vessels A and B are identical, adding the amino acids of the unmodified sequence. At the end of 10 cycles, all the resin in vessel A has been transferred into vessel B which now contains the desired array of peptide analogues in resin-bound form.

B. Synthesis of a Defined Peptide Array

Figures 15A, 15B:
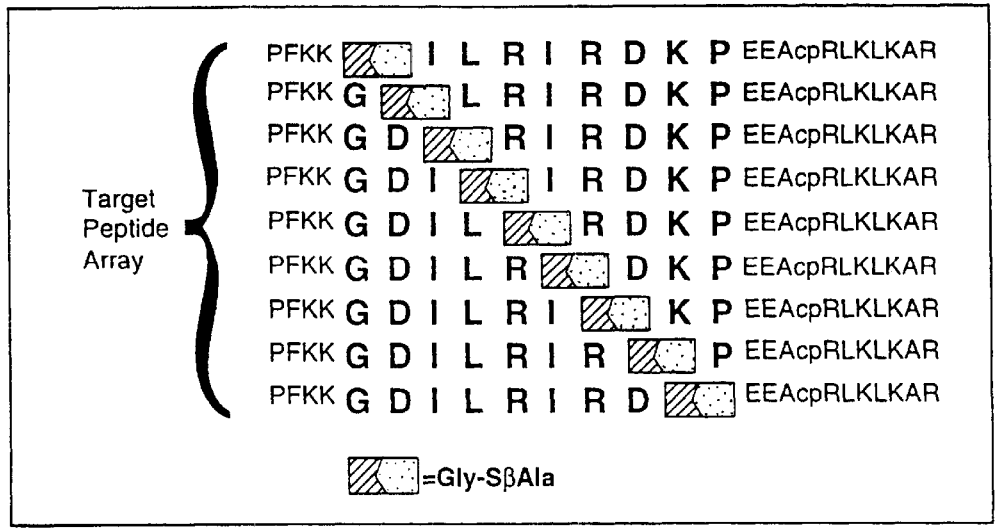
FIG. 15 illustrates: (A) the target composition of the nine member array of peptide analogues. The sequence (SEQ ID NO 2) PFKKGDILRIRDKPEE was derived from residues 152–167 of the murine cCrk SH3 domain and the C-terminal AcpRLKLKAR sequence (SEQ ID NO 3) was used to facilitate analysis by MALDI mass spectrometry; (B) Synthetic operations required for the synthesis of a peptide array consisting of nine overlapping dipeptide analogues over a ten amino acid sequence. The synthesis was performed in a single day (SEQ ID NOs 2, 5–6 and 26–36).

A peptide array consisting of a ten amino acid sequence, (SEQ ID NO 4) GDILRIRDKP was chosen as a target to demonstrate the approach, following the methodology as described above. The target array is shown in FIG. 15A, and consists of overlapping dipeptide analogues in the region of interest. In order to facilitate characterization by mass spectrometry, the array was synthesized on resin bearing the sequence (SEQ ID NO 5) EEAcpRLKLKAR, where Acp is ε-aminocaproic acid (Zhao et al. *Proc. Nat. Acad. Sci.* 1996, 93, 4020–4024). The dipeptide analogue moiety corresponding to —NH—CH$_2$—CO—S—CH$_2$—CH$_2$—CO— (Gly-SβAla) was introduced as Boc-Gly-SβAla. Since the analogue moiety was incorporated as a dipeptide, a modification was made to the synthetic procedure outlined above and shown in FIG. 4. In order to keep the synthetic operations being performed on the peptides in vessels A and B in register, the sample being derivatized in 1 was held out for two cycles before transfer to vessel B. To accommodate this modification, a second auxiliary funnel 1' was added.

In practice, the peptide-resin sample from vessel A was added to a funnel in position 1, where the dipeptide analogue coupling was initiated. After one cycle, the funnel was moved to position 1', where the dipeptide analogue coupling continued during a second cycle of chain elongation in vessels A and B. The analogue-containing sample of peptide-resin was then washed with DMF (dimethylformamide) and transferred to vessel B. The synthetic steps for this synthesis are outlined in FIG. 15B. After substituting dipeptide analogues for nine consecutive dipeptide sequences (SEQ ID NO 6) spanning a region of 10 amino acids, four additional amino acids, PFKK, were coupled to the array of peptide-resins in vessel B to complete the target sequence.

C. Characterization of the Peptide Array

Figure 16A:
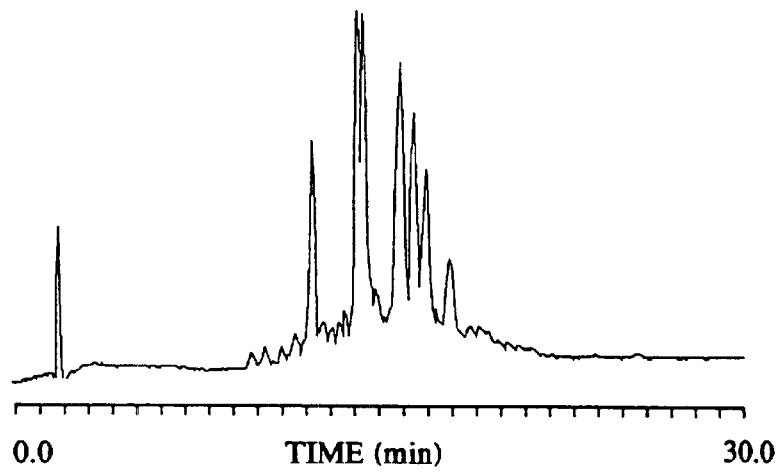
FIG. 16 illustrates the analysis of a nine component array of peptide analogues. A) Analytical HPLC of crude full length product (gradient, 20–50% buffer B over 30 minutes). B) MALDI mass spectrum of crude full length product. Unlabelled peaks at lower mass are termination byproducts from the synthesis. C) Analytical HPLC of hydroxylamine-cleaved HPLC product on the same gradient. D) MALDI readout of hydroxylamine-cleaved peptide array [Peaks with * are N-terminal-containing fragments; unlabeled peaks are C-terminal containing fragments].
Figure 16C:
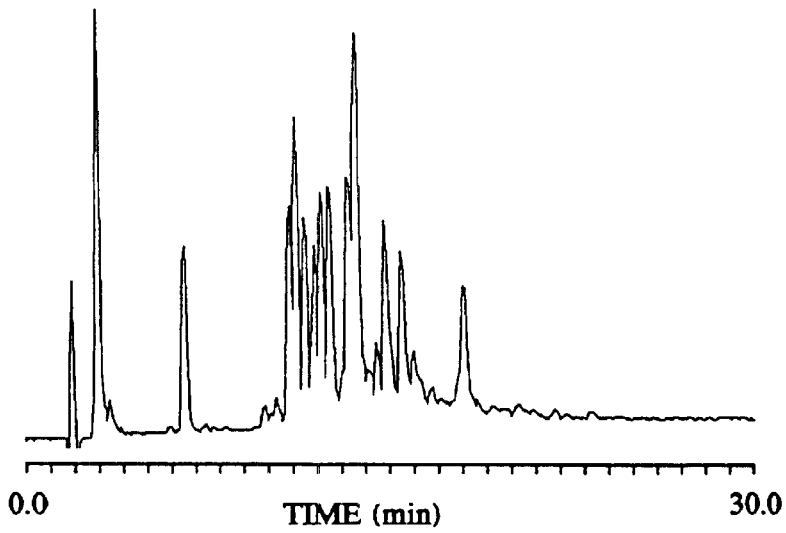
Figure 16B:
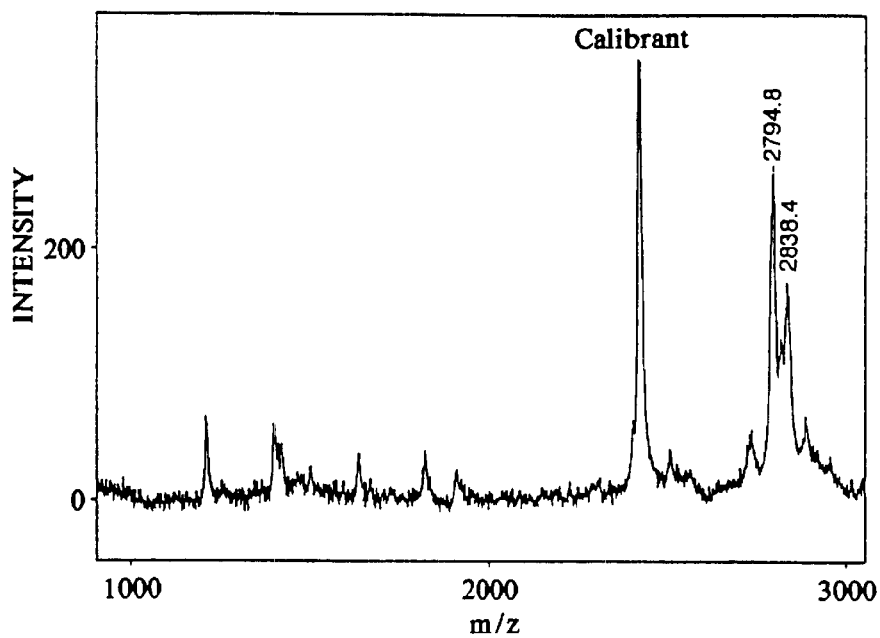

The peptide array described above contains a mixture of nine peptides, all 24 residues in length, each differing only in the position of a Gly-SβAla dipeptide substitution. As expected, the analytical HPLC of this array is quite complex, with many overlapping peaks (FIG. 16A) The MALDI mass spectrum is also poorly resolved since the peptides in the array have a high redundancy in their molecular weights (FIG. 16B). Thus the sequence -LRIRD- contains the dipeptides LR, RI, IR, each of which have a molecular weight of 269 Da and RD which has a molecular weight of 271 Da. When substituted with Gly-SβAla (145 Da) in the peptide arrays, each of these substitutions would result in a peptide analogue with a molecular weight of 125±1 Da below that of the unmodified sequence (SEQ ID NO 7). (PFKK-GDILRIRDKP-EEAcpRLKLKAR.amide, M. W. 2920 Da). The resulting MALDI mass spectrum of this peptide array would be expected to have a large peak around 2795 Da, representing the sum of four different peptide components, (see FIG. 16B).

D. 'Self-Encoded' Peptide Arrays

The poor HPLC separation and redundancy in molecular weight creates a challenge for identification of components present in the array of peptide analogues. The distinguishing feature of the components in this peptide array is the unique position of the modification in the sequence. One approach to the unambiguous identification of the peptide components is to incorporate a selectively cleavable bond in the analogue unit. Cleavage of this bond in an analogue peptide would result in two peptide fragments whose lengths, measured as mass, would define the position of the analogue unit in the peptide from which they derived. Such a chemical cleavage site would have to be stable to normal handling (folding and assay) conditions, while permitting selective cleavage on demand. We have investigated the incorporation, stability and selective cleavage properties of two potential readout chemistries, based on ester and thioester bonds.

1. Synthesis and Characterization of a Peptide Containing a Cleavable Thioester Backbone as Illustrated in FIG. 17A The peptide LYRA(Gly-SβAla)-YGGFL.amide, (SEQ ID NO 8) was synthesized by stepwise SPPS using in situ neutralization coupling protocols. The thioester-containing dipeptide analogue, Boc-Gly-SβAla was activated as an HOBt ester and then coupled to pre-neutralized NH$_2$-YGGFL- (SEQ ID NO 9) (4-Me)benzhydrylamine)-resin. Following deprotection and cleavage from the peptide-resin, the stability of the model thioester-containing peptide was determined.

Thioester bonds within peptide sequences have been found to be stable at neutral pH (Schnölzer et al. *Science* 1992, 256, 221–225; Baca et al. *J. Am. Chem. Soc.* 1995, 117, 1881–1887; Canne et al. *J. Am. Chem. Soc.* 1996, 118, 5891–5896). To test for stability to base hydrolysis, the peptide was dissolved at pH 9.0 in 200 μL of 100 mM Tris, 1 M Gn.HCl, vortexed vigorously for 10 seconds and left at 23° C. for 30 minutes. Surprisingly, no hydrolysis was observed under these conditions. Addition of 20 μL of 1 M NaOH to (pH~13) gave complete hydrolysis after just 10 minutes as monitored by HPLC and electrospray mass spectrometry. In contrast to their stability to hydrolysis, thioesters have been shown to be very labile to hydroxylamine at neutral pH levels (Bruice et al. *J. Am. Chem. Soc.* 1964, 86, 4886–4897). As shown in FIG. 17A, the thioester peptide was completely cleaved into LYRAG-NH$_2$OH(SEQ ID NO 10) and HSCH$_2$CH$_2$CO-YGGFL.amide (SEQ ID NO 11) when dissolved in 1 M NH$_2$OH, 200 mM NH$_4$HCO$_3$, pH 6.0 for 30 minutes. Thioesters can be completely cleaved at concentrations of NH$_2$OH as low as 10 mM in <30 minutes.

Figure 17B:
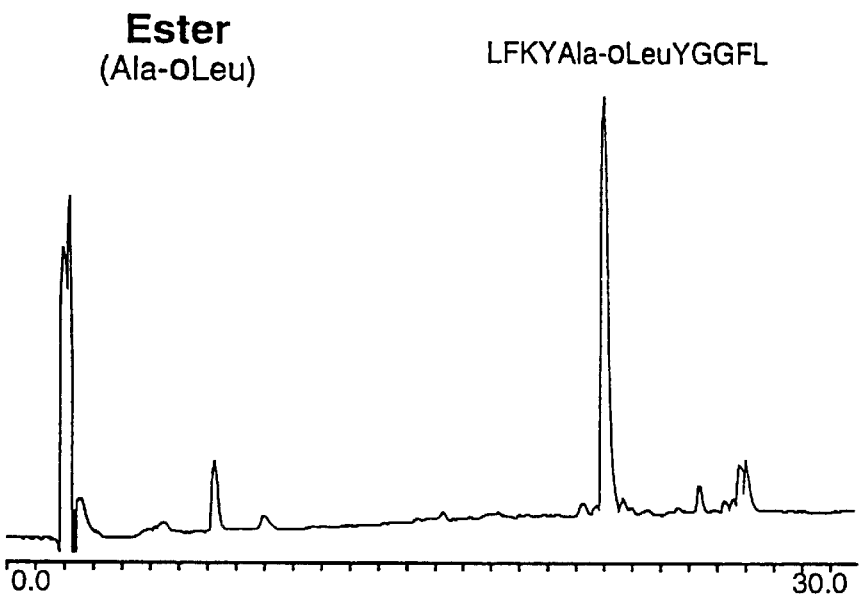
FIG. 17 illustrates the analytical HPLC of the chemical cleavage of model peptides containing labile backbone bonds. A,C) Cleavage of a thioester-containing peptide with hydroxylamine. B,D) Cleavage of an ester-containing peptide by hydrolysis.
Figure 17D:
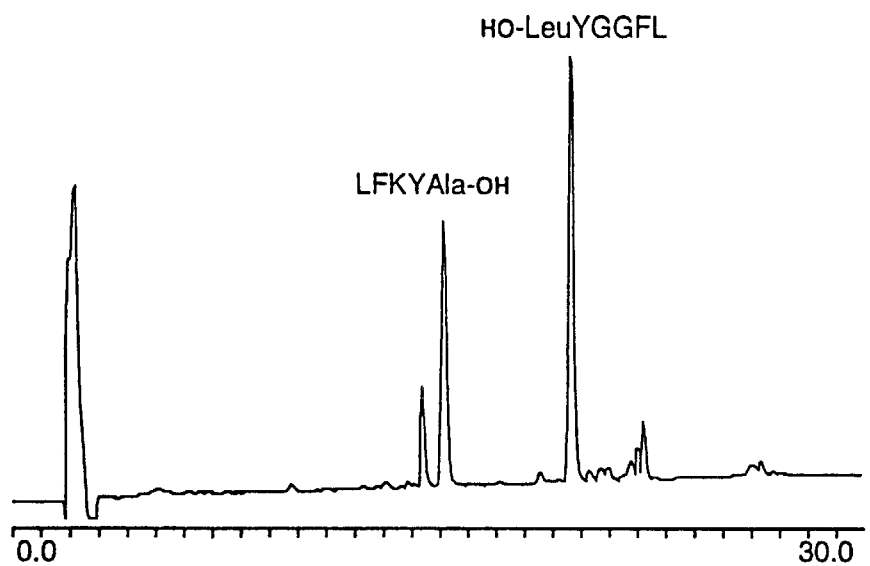

2. Synthesis and Characterization of a Peptide Containing a Cleavable Ester Backbone as Illustrated in FIG. 17B The peptide, YKLFAla-[coo]-YGGFL.amide (SEQ ID NO 12) was prepared by stepwise SPPS, using in situ neutralization coupling protocols and Boc chemistry. The ester bond in the peptide was formed by coupling Boc-Ala to an α-hydroxy acid using 4-dimethylaminopyridine as a catalyst. Following deprotection and cleavage from the peptide-resin, the model ester-containing peptide was analyzed for stability. The ester bond was quite resistant to hydrolysis, taking six hours to cleave at pH 10, FIG. 17B. In addition, the ester peptide was stable to treatment with 1 M NH$_2$OH, 200 mM NH$_4$HCO$_3$, pH 6.0 for up to 12 hours. The high stability of the ester to hydroxylamine should allow for the use of a backbone thioester as a chemical readout in peptides containing ester bonds. More recent studies have shown that the ester can be readily cleaved by NH$_2$NH$_2$ at neutral pH. A Gly-[coo]-Gly containing peptide was cleaved in under one hour by dissolving in 150 mM hydrazine, 100 mM Sodium Phosphate, 6 M guanidine.HCl, pH 7.0 (Carrasco, M. unpublished).

Figure 18A:
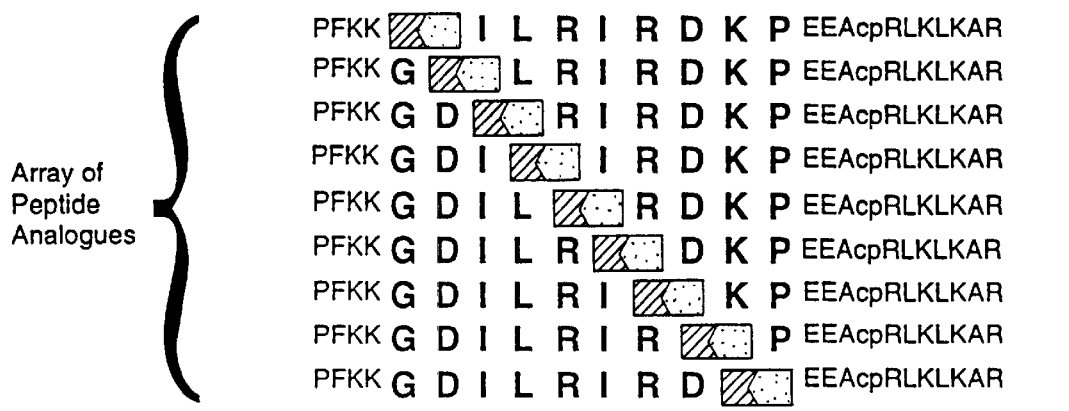
FIG. 18 illustrates the schematic representation of the cleavage of the nine component array of peptide analogues. A) Full length array of nine peptide analogues. B) Cleaved array of peptide analogues. The mixture consists of eighteen peptides corresponding to nine N-terminal fragments and nine C-terminal fragments (SEQ ID NOs 5, 6 and 26–36).
Figure 18B:
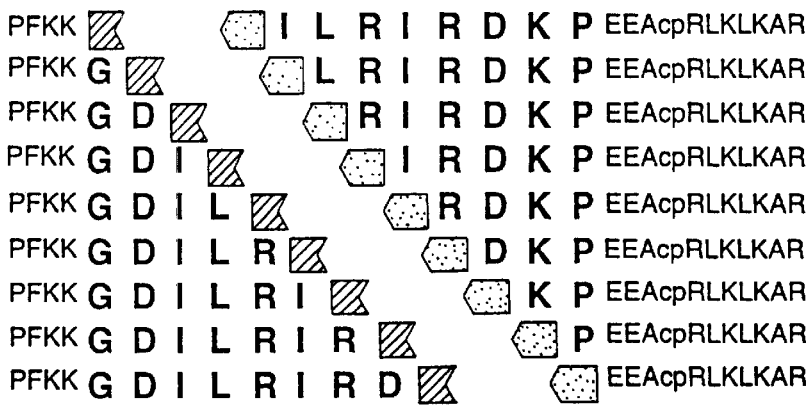

E. Readout of the Nine Component Peptide Analogue Array of the Parent Sequence PFKK-GDILRIRDKP-EEAcpRLKLKAR.amide Synthesis of this array has been described above. Each member of this peptide array contains a Gly-SβAla replacement at one of the nine possible dipeptide positions within the ten amino acid sequence, (SEQ ID NO 4) [GDILRIRDKP] as shown in FIG. 15A. In order to facilitate unambiguous identification of the components in the array, the thioester readout chemistry has been incorporated into the dipeptide analogue. The thioester bond in the Gly-SβAla dipeptide analogue introduces a unique cleavage site into each member of the peptide array. Chemical cleavage of the peptide analogue array was expected to produce 18 peptide fragments as shown in FIG. 18.

The peptide analogue array was cleaved by treatment with 1 M NH$_2$OH, 200 mM NH$_4$HCO$_3$, pH 6.0 for 20 minutes.

Figure 16D:
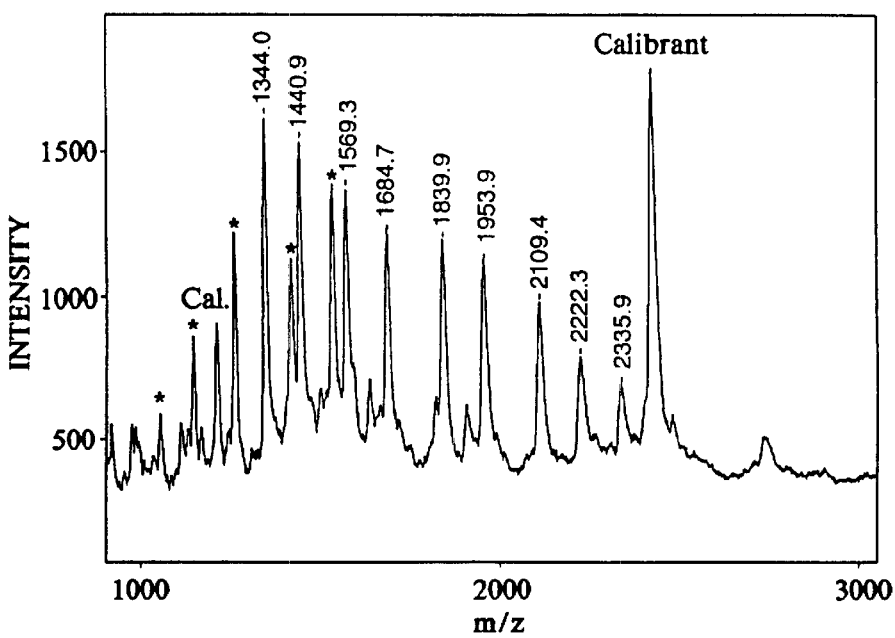
Figure 19:
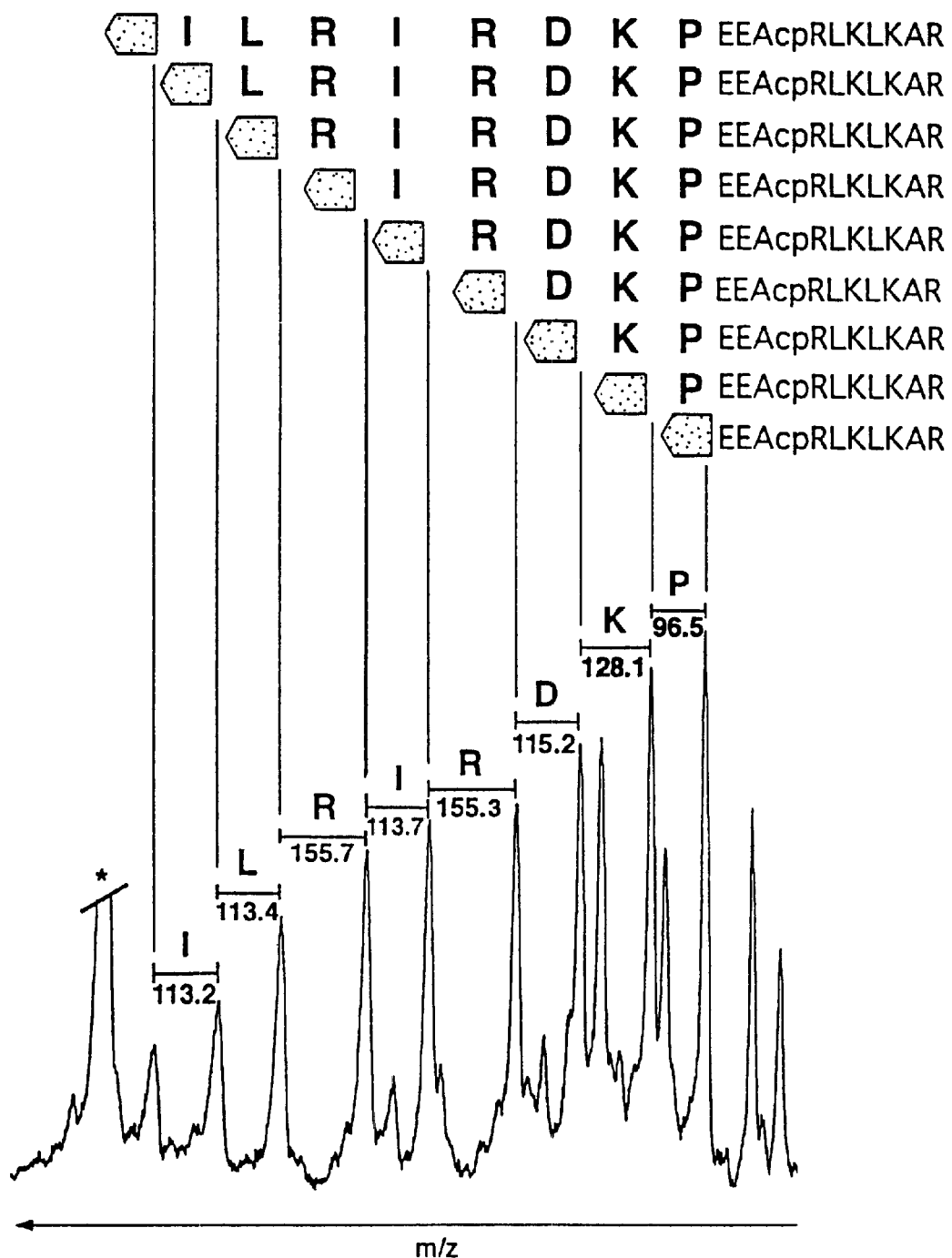
FIG. 19 illustrates the relation of the MALDI spectrum to the peptide C-terminal fragment array. The horizontal mass scale spectrum has been inverted to align it with the standard N-to-C terminal orientation of the peptide sequence. The peaks corresponding to the nine C-terminal peptide fragments are clearly resolved and can be assigned sequentially. In addition to the position of the peak in the mass spectrum, the mass difference between adjacent peaks identifies the individual amino acids in the peptide sequence that has been subjected to analoguing. The starred peak corresponds to the callibrant (SEQ ID NOs 3, 5, 26–28 and 32).

The resulting peptide fragments were then analyzed by HPLC and by MALDI mass spectrometry. As with the uncleaved peptide array, FIG. 16A, the components of the cleaved peptide array, FIG. 16C, still give rise to a complicated and essentially uninformative HPLC chromatogram. By contrast, the MALDI spectrum of the unfractionated cleaved peptide array, provides a very straightforward characterization of the peptide array, FIG. 16D. As shown in FIG. 19, the masses of the nine C-terminal fragments from the cleaved array are easily located in the mass spectrum (Signals corresponding to 5 of the 9 N-terminal peptides were also observed. The masses that were not resolved were obscured by matrix ions in the region below 1000 Da in the spectrum of the peptide mixture), and served to unambiguously identify the position of the analogue unit in each component of the original peptide array before cleavage.

The MALDI mass spectrometric readout characterized the peptide array in several ways. Cleavage of the analogue unit, at different positions throughout the array, produces two families of related peptides. These two families have either the N- or C-terminus of the parent peptide in common. In this experiment, the identification of each member of the C-terminal family of peptides by MALDI can be directly related to the presence of each full length peptide analogue in the parent array. In addition to the C-terminal family, five members of the N-terminal family of peptides were also observed. The starred peaks on mass spectrum in FIG. 16D correspond to these N-terminal peptides. In practice, the identification of either the N-terminal or C-terminal peptide fragments would serve to unambiguously characterize the peptide analogue array.

Another characterization of the peptide array can be obtained by looking at the difference in masses between the peaks on the mass spectra. As shown in FIG. 19, the nine C-terminal peptide fragments are all of different lengths, and the mass differences between neighboring fragments correspond to the masses of individual amino acid residues. By correlation of these mass differences to the mass of individual amino acids, the sequence through which the analogue unit was substituted can be confirmed. This type of analysis has been previously used to sequence native peptides by 'protein ladder sequencing' (Chait et al. *Science.* 1993, 262, 89–92).

F. Discussion

An embodiment of the present invention is the synthesis of a defined array of peptide analogues as a single mixture. This peptide array can be assayed as a pool, after which individual peptide components can be identified through a novel encoding scheme. Using this approach, the comparative properties of the individual components can be determined for a given assay/function. The adaptation of this analogue array methodology to the study of structure-function relationships in proteins is illustrated in Example 2 (infra).

The peptide array can be synthesized using a modified 'split resin' procedure which, unlike previous procedures, results in a defined array of components with only the desired complexity. A key aspect of this approach is the ability to prepare a defined subset of a fully combinatorial synthesis. By synthesizing such a subset, arrays of manageable size can be prepared that contain defined modifications at a large number of positions in the peptide sequence. For example, using this methodology, five different amino acid analogues could be substituted at each position of a ten amino acid sequence so that there is only one modification in each peptide molecule. The resulting array would result in a mixture of 50 peptides (5 analogue structures×10 positions). Using the standard split synthesis approach (Furka et al. *Int. J. Pept. Prot. Res.* 1991, 37, 487–494; Lam et al. *Nature* 1991, 354, 82–84), the same 50 peptides would be only a small fraction of a library of $\sim 10^7$ ($5^{10}$) peptides.

Once diversity has been generated, and a selection performed, a method is needed to identify individual components. Such approaches to decoding peptide mixtures have presented a substantial challenge. Most encoding strategies involve a molecular tag which can be read by sensitive analytical techniques (Needels et al. *Proc. Natl. Acad. Sci. U.S.A.* 1993, 90,10700–10704; Kerr et al. *J. Am. Chem. Soc.* 1993, 115, 2529–2531; Nikolaiv et al. *Pept. Res.* 1993, 6, 161–170; Ohlmeyer et al. *Proc. Natl. Acad. Sci. U.S.A.* 1993, 90, 10922–10926) or by amplification (Brenner et al. *Proc. Natl. Acad. Sci. USA.* 1992, 89, 5381–5383; Nielsen et al. *J. Am. Chem. Soc.* 1993, 115, 9812–9813). Many of these techniques, however, rely on the assay of molecules still attached to a solid support and the isolation and analysis of individual beads. To avoid the necessity for a solid support, the encoding must be associated with the peptide analogue at the molecular level (Brenner et al. *Proc. Natl. Acad. Sci. USA.* 1992, 89, 5381–5383; Nielsen et al. *J. Am. Chem. Soc.* 1993, 115, 9812–9813).

Incorporation of a chemically cleavable bond at specific sites within the peptide analogues provides an example of an alternative simple and practical encoding scheme at the molecular level. After a physical selection for a desired function, the components of the peptide array can be decoded through chemical cleavage and one step mass spectrometric readout. Detection of the resulting peptide fragments unambiguously defines the presence or absence of a given analogue molecule in the selected population. As demonstrated in the analysis of the nine member peptide array, matrix assisted laser-desorption ionization (MALDI) mass spectrometry is well suited for the decoding of linear arrays of peptides (Chait et al. *Science.* 1993, 262, 89–92). This use of mass spectrometry to decode mixtures of peptide analogues is analogous to the use of gel electrophoresis to separate nucleotides by length during DNA sequencing and analysis (A similar cleavage and separation by size readout was used for nucleic acids in: Pan et al.; *Science.* 1991, 254,1361–1364; Hayashibara et al. *J. Am. Chem. Soc.* 1991, 113, 5104–5106). The high resolution and sensitivity (<1 pmol/component; Chait et al. *Science* 1992, 257, 1885–1894) of MALDI mass spectrometry allows the characterization of even small quantities of the entire peptide array.

In this example, we have demonstrated the feasibility of this approach through the synthesis of a peptide array which was then characterized by MALDI mass spectrometry following chemical cleavage. A nine component peptide array of the parent sequence, (SEQ ID NO 7) PFKK-GDILRIRDKP-EEAcpRLKLKAR.amide, was synthesized in which a single dipeptide analogue, Gly-SβAla, was introduced into consecutive positions through the sequence (SEQ ID NO 4) -GDILRIRDKP- (FIG. 15). This array was self-encoded with a chemically cleavable thioester bond which was incorporated into the analogue unit. The peptide components were then identified by cleaving the thioester bond in each peptide with hydroxylamine, followed by MALDI mass spectrometry. The resulting series of peaks on the mass spectrum unambiguously identified the presence of all nine peptide analogues in the peptide array.

The combination of the synthesis of an array of peptides corresponding to a defined subset of a fully combinatorial mixture with a self-encoding strategy results in an information-rich approach to the elucidation of the structure-activity relationship of peptides, polypeptides and proteins. The power of this approach is illustrated when the peptide array is subjected to a functional selection (example 2). Since all members of the peptide array can be observed in a single readout step, this approach can generate information on both the positively and negatively selected members of the array. It is anticipated that the ability to synthesize multiple peptide analogues in a single procedure, followed by functional characterization of the entire peptide array will give greater insight into the molecular basis of peptide function.

This procedure allows for controlled diversity to be generated at multiple positions in a peptide chain. In addition, a novel self-encoded approach to identifying peptide analogues has been developed which involves the incorporation of a cleavable bond which is associated with a particular modification. This chemical readout system allows the entire peptide array to be analyzed simultaneously by sensitive analytical techniques such as MALDI mass spectrometry.

By reading out an entire pool of peptide analogues in a single step, a profile of structure-function relationship across all members of the array could be generated. Interpretation of such profiles will provide information of the molecular basis for peptide function. Such peptide arrays could be used to elucidate the molecular basis of important functional properties by systematically removing structural elements of a peptide. In particular, hydrogen bond donors and acceptors in the backbone can be deleted using a wide variety of backbone analogues. Additionally, new functional characteristics can be introduced through the systematic introduction of new sidechain and backbone groups. The use of defined arrays of synthetic peptide analogues coupled with a single step readout provides new insights into the chemical basis of peptide activity.

EXAMPLE 2
(Illustrates Chemical Synthesis, Functional Separation, and Readout of Self-encoded Arrays of an SH3 Peptide Consisting of the Ten Amino Acid Sequence, (SEQ ID NO 4) GDILRIRDKP)

This example illustrates an integrated approach to the preparation of a defined array of protein analogues in a single synthesis, their functional separation into active and inactive pools, and a simple one step readout of the composition of the self-encoded mixtures. The strategy is outlined in FIG. 21. The chemical synthesis and encoding strategies are an extension to proteins of the approach described in example 1 (supra). Instead of synthesizing a single modified protein, an array of protein analogues is prepared in a single total chemical synthesis. The proteins in the array differ from each other only by the position in which a defined covalent modification is located within the polypeptide sequence. The composition of the analogue array can be decoded by means of a latent readout chemistry introduced in conjunction with each analogue unit. This latent readout chemistry allows proteins to be specifically cleaved, yielding a pattern of peptide fragments which unambiguously identifies the individual components of the mixture and defines the position of the analogue unit in each compound (A similar readout system has been developed for use in DNA systems: Hayashibara et al. *J. Am. Chem. Soc.* 1991, 113, 5103–5106). By comparing the readout patterns obtained before and after a functional separation, a profile is obtained relating the effects of the analogue structure to its position in the polypeptide chain. Accumulation and interpretation of such qualitative profiles of protein structure-function relationships 'protein signatures' provides insights into the chemical basis of protein function.

A family of analogue proteins was characterized using the invention with the N-terminal SH3 domain of the adapter protein cCrk (Murine cCrk, N-terminal SH3 domain (residues 134–191); Genbank accession s72408). SH3 domains are small monomeric modules which are present in many proteins involved in signal transduction. It is now well established that SH3 domains mediate protein-protein interactions within intracellular signaling networks through the recognition of short proline-rich sequences from other adapter proteins (Ren et al. *Science* 1993, 259, 1157–1161). Individual SH3 domains have been shown to fold in vitro to a defined tertiary structure and to bind proline-rich peptides with low $\mu$M affinity. In addition several of these domains have been structurally characterized by both NMR and X-ray crystallography (Musacchio et al. *Nature* 1992, 359, 851–855; Yu et al. *Science* 1992, 258, 1665–1668).

Using the methods described in example 1 (supra), a family of nine analogues was prepared to investigate the effect of an extensive covalent modification of the 58 amino acid residue SH3 polypeptide chain on its ability to fold and bind its specific peptide ligand. Each member of the synthetic protein array contained a single dipeptide analogue unit, —NH—CH$_2$CO—SCH$_2$CH$_2$CO— (Gly-S$\beta$Ala), replacing pairs of adjacent amino acids at unique positions in the native sequence (see FIG. 23). The mixture of analogue polypeptide chains was folded and assayed for binding to a specific ligand, a short proline-rich synthetic peptide derived from the sequence of the guanine nucleotide exchange factor C3G (Knudsen et al. *J. Biol. Chem.* 1994, 269, 32781–32787). After the affinity selection, the binding and non-binding pools of protein analogues were cleaved selectively at the thioester bond contained in each analogue unit, and the composition of each pool was read out using MALDI mass spectrometry. In this manner, a pattern of signals was obtained, which related the position of the chemical modification within the SH3 polypeptide sequence to its effects on folding and/or ligand binding.

A. Chemical Synthesis of the 58 Residue SH3 Polypeptide

Figure 28A:
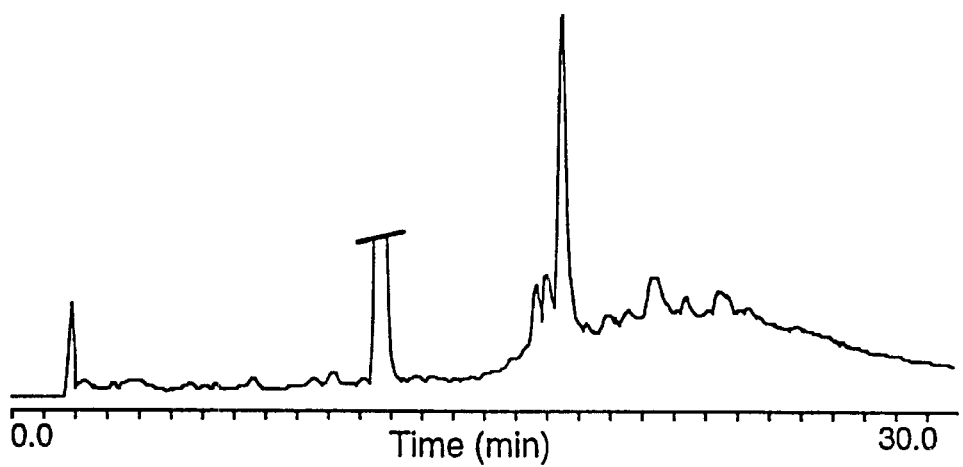
FIG. 28 illustrates a characterization of the purified synthetic murine cCrk 134–191, N-terminal SH3 domain. A. Analytical HPLC of the total crude peptide products from HF cleavage. B. Analytical HPLC of the purified product on a gradient of 20%–50%B over 40 minutes. C. Electrospray mass spectra of the purified product. Inset spectrum is reconstructed to a single charge state from the raw data below. Calculated mass for $C_{313}H_{470}N_{84}O_{95}S_1$ 6961.8 Da (average isotope distribution); Observed mass 6962±1 Da.
Figure 28B:
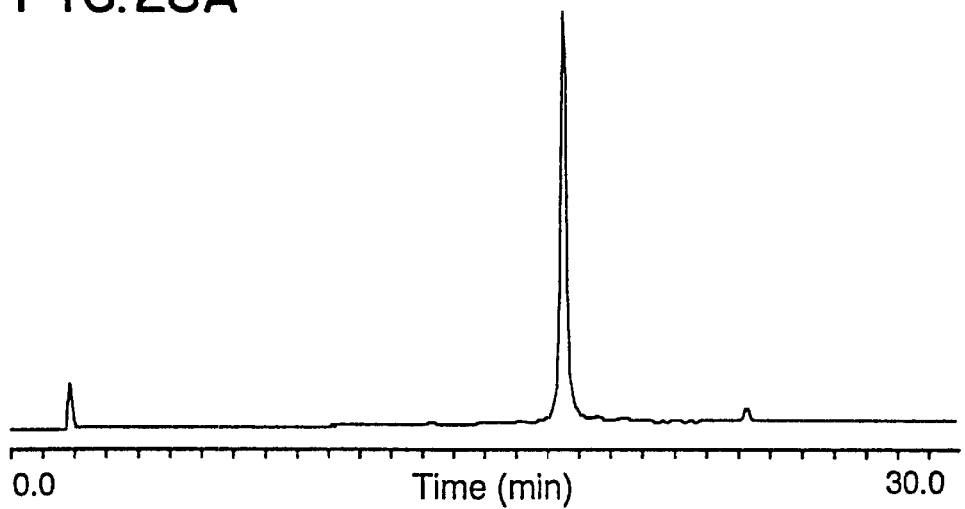
Figure 28C:
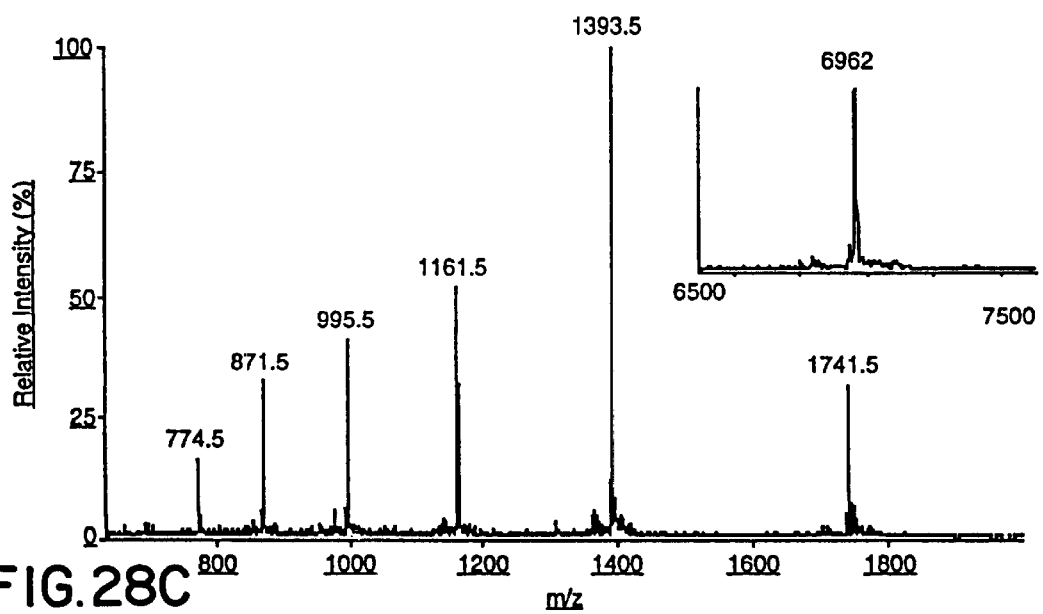

The polypeptide chain of the murine cCrk N-terminal SH3 domain, corresponding to residues 134–191 of the full cCrk signaling protein (Murine cCrk, N-terminal SH3 domain (residues 134–191); Genbank accession s72408), was assembled by highly optimized, stepwise solid phase peptide synthesis using machine-assisted in situ neutralization protocols for tert-butoxycarbonyl (Boc) chemistry (Schnölzer et al. *Int. J. Pept. Protein Res.* 1992, 40, 180–193). After deprotection and cleavage from the resin support, the crude polypeptide was purified by semipreparative reversed-phase HPLC and lyophilized using procedures as described by Clark-Lewis et al. *The Use of HPLC in Receptor Biochemistry*; Venter, J. C. and Harrison, L. C. Eds.; Alan R. Liss, Inc: New York, 1989; Chapter 3. The purified product was characterized by analytical HPLC and by electrospray mass spectrometry (Schnölzer et al. *Anal Biochem.* 1992. 204. 335–343). The results are shown in FIG. 28.

B. Functional Characterization of the Synthetic SH3 Domain

The N-terminal cCrk SH3 domain was formed by folding under these conditions: 0.2 mg of the purified 58 residue polypeptide in 600 $\mu$L of 20 mM HEPES 50 mM NaCl pH 7.3 at room temperature for 15 minutes. The folded protein was structurally characterized by NMR and crystallization (The folded protein was characterized by two dimensional NOESY 1H NMR spectroscopy. In addition, the synthetic protein solution used for NMR analysis spontaneously formed crystals upon storage at 4° C. These crystals diffracted to >2.3 Å allowing for the solution by molecular replacement. Refinement of the structure is in progress). The resulting synthetic protein domain was then assayed for its affinity for two different proline-rich peptides. Binding of this SH3 domain to its cognate peptide ligand buries a tryptophan sidechain of the protein found in the binding pocket. This change in solvent exposure leads to an increase in the fluorescence intensity of the tryptophan sidechain which can be monitored as a function of increasing ligand concentration (Feng et al. *Science* 1994.266, 1241–1245). The $K_d$'s for the peptides C3G (PPALPPKKR.amide) (SEQ ID NO 13) and a peptide designed for attachment to an affinity column, Acetyl-CWAcp-C3G, were found to be 1.8 $\mu$M and 2.4 $\mu$M respectively (Due to the polyproline nature of the ligands, fluorescence measurements were taken after 12 hours incubation of the protein with the peptide ligand to allow equilibration of the multiple cis and trans isomers). The C3G affinity of 1.8 $\mu$M for the C3G derived peptide is comparable to the affinity reported for a recombinantly derived SH3 domain (1.9 $\mu$M) (Wu et al. *Structure* 1995, 3, 215–226).

C. Affinity Chromatography of the Synthetic SH3 Domain

An affinity column carrying a synthetic C3G derived peptide was prepared by reaction of the cysteine side chain of Acetyl-CWAcp-PPALPPKKR.amide (SEQ NO ID NO 14) with an iodoacetylated agarose matrix. The linker Acetyl-CWAcp- was designed to combine a reactive sulfhydryl on the Cys sidechain with a spectroscopic tag in the Trp residue, and to introduce a flexible spacer region between the support and the peptide ligand in the form of $\epsilon$-aminocaproic acid. The amount of peptide on the column, was determined as 5 $\mu$mol/mL of the swollen agarose matrix from the absorbance at 280 nm of the peptide solution before and after reaction with the column. As a control for non-specific binding effects, a second column with comparable peptide loading was made by the same procedure using a non C3G sequence, Ac-CWAcpYGGFL.amide (SEQ ID NO 15).

Specific binding of the native sequence synthetic cCrk N-terminal SH3 domain was demonstrated to the C3G-peptide affinity support by loading crude synthetic cCrk (134–191) mixed with BSA. The proteins were allowed to equilibrate for 6 hours after which a series of increasing washes up to 1 M NaCl, and one wash with 1 M $NH_2OH$ was performed. The column effluent was monitored by absorbance at 280 nm and selected fractions subjected to mass spectrometry. The BSA was completely washed off the column after the 300 mM NaCl wash. The cCrk N-terminal SH3 domain, however, remained bound to the column throughout the NaCl and $NH_2OH$ washes. The cCrk domain was only eluted by a 6M Gn.HCl wash that disrupted the specific interactions between the protein and the synthetic C3G-derived peptide. It is interesting to note that the 58 amino acid cCrk SH3 domain was stable to 1 M $NH_2OH$ treatment despite the presence of the sequence Asn-Gly-Asn (144–146) which can be prone to $NH_2OH$ cleavage (Clarke et al. *Stability of Protein Pharmaceuticals, Part A:*, Ahern, T. J.; Manning, M. C. Ed. Plenum Press, New York, 1992).

Figures 23A, 23B, 23C:
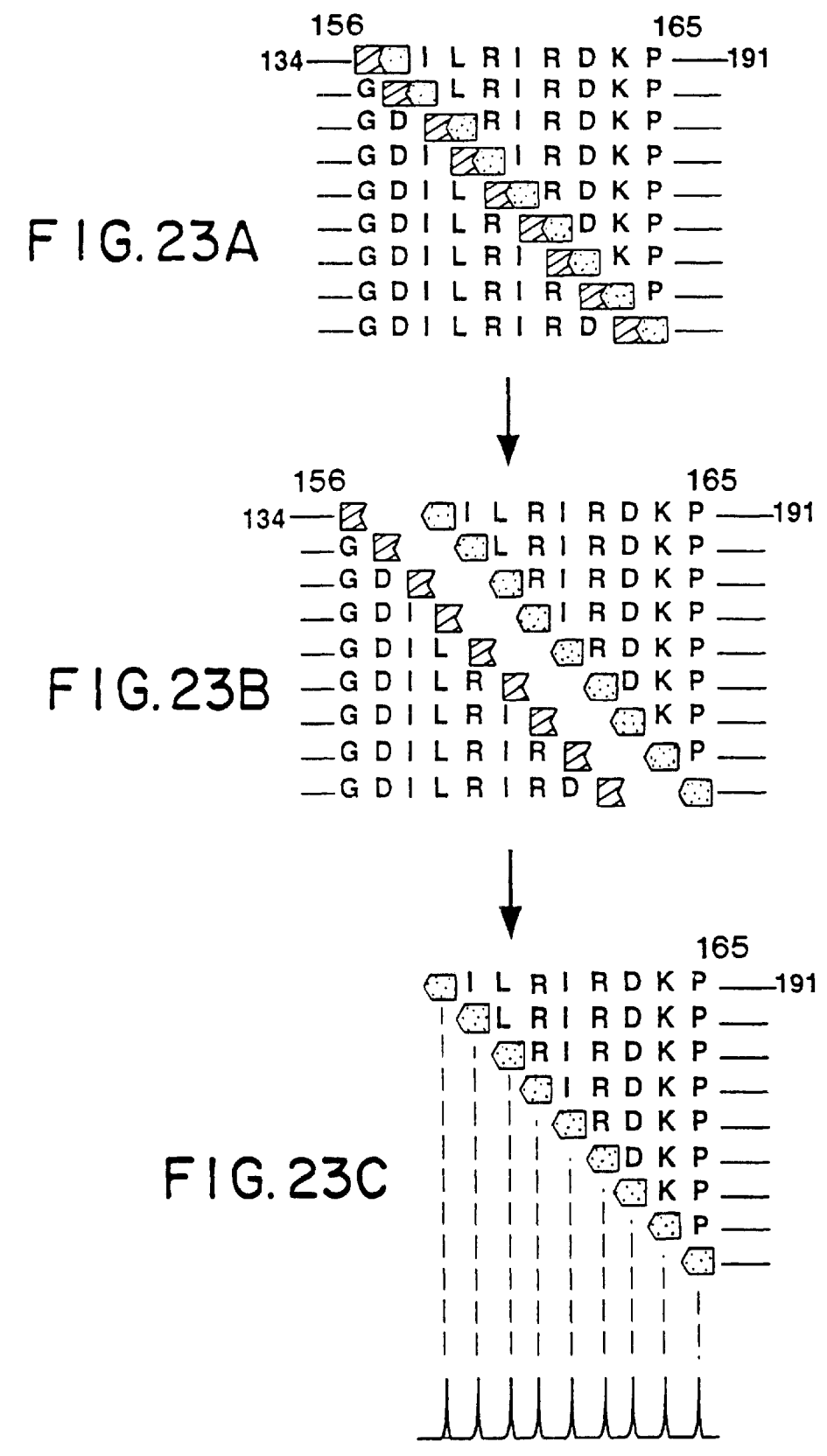

D. Chemical Synthesis of an Array of Analogues of the 58 Residue Polypeptide Chain The target array consisted of nine polypeptides, each containing a single —$NHCH_2CO$—$SCH_2CH_2CO$— (Gly-S$\beta$Ala) substitution at one of the nine possible dipeptide units within the ten amino acid sequence defined by residues 156–165 within the cCrk sequence 134–191 (FIG. 23). The Gly-S-$\beta$Ala analogue unit was designed to remove two consecutive amino acid sidechains and to insert an extra methylene into the polypeptide backbone of the SH3 protein. Inclusion of the thioester bond added a latent chemical cleavage site for the readout of the composition of the mixture of protein analogues and simultaneously deleted a backbone hydrogen bond donor. Backbone flexibility was also increased due to the loss of the planarity associated with the peptide bond. The analogue substitutions covered overlapping dipeptide sequences through the region -GDRILRIDKP- (SEQ ID NO 16), corresponding to residues 156–165 of the cCrk sequence as shown in FIG. 23A.

The polypeptide analogue array was synthesized using a combination of manual and machine-assisted protocols. The sequences corresponding to cCrk(166–191) and cCrk (134–155) were synthesized using a machine-assisted protocol for Boc-solid phase chemistry (Schnölzer et al. *Int. J. Pept. Protein Res.* 1992, 40, 180–193). Following synthesis of cCrk(166–191), the peptide-resins were removed from the peptide synthesizer and placed in a manual-synthesis reaction vessel. Synthesis of cCrk(156–165) with concomitant introduction of the analogue unit at each position was performed as previously described for a model peptide system (A similar readout system has been developed for use in DNA systems: Hayashibara et al. *J. Am. Chem. Soc.* 1991, 113, 5103–5106) using a modified split-resin procedure. Before addition of each residue (157–165), a sample of peptide-resin was removed from reaction vessel A, modified with a dipeptide analogue for two synthetic cycles and then transferred to a second reaction vessel B. Identical synthetic operations building up the native amino acid sequence were carried out in reaction vessels A and B. In this manner, an array of nine resin-bound polypeptides was created as a single mixture, containing consecutive overlapping Gly-S$\beta$Ala substitutions. Chain elongation of the nine component mixture was continued through the sequence cCrk (134–155) using machine assisted synthetic cycles. The mixture of full-length analogue-containing polypeptide-resins was subjected to HF cleavage and simultaneous sidechain deprotection to give a crude lyophilized mixture of nine analogues of the 58 amino acid polypeptide chain of the N-terminal cCrk SH3 domain.

The members of the polypeptide array were folded by dissolving 0.5 mg of crude peptide product in 200 $\mu$L of 20 mM HEPES 50 mM NaCl pH 7.3 at room temperature. After 1 hour, the protein mixture was analyzed by HPLC and MALDI mass spectrometry. By HPLC (FIG. 29A), the nine protein components were partially resolved against a background of synthetic byproducts. MALDI mass spectrometry (FIG. 29B) showed an unresolved mixture of full-length polypeptide chains centered around 6950 Da; minor amounts of terminated components formed as byproducts in the chain assembly were also present. The presence of full length protein analogues indicates that the thioester-containing polypeptide chains are stable under these assay conditions. However, neither HPLC nor MALDI-MS was able to define the composition of the array of protein analogues.

E. Readout of the Composition of the Parent Array of Protein Analogues

Figure 29A:
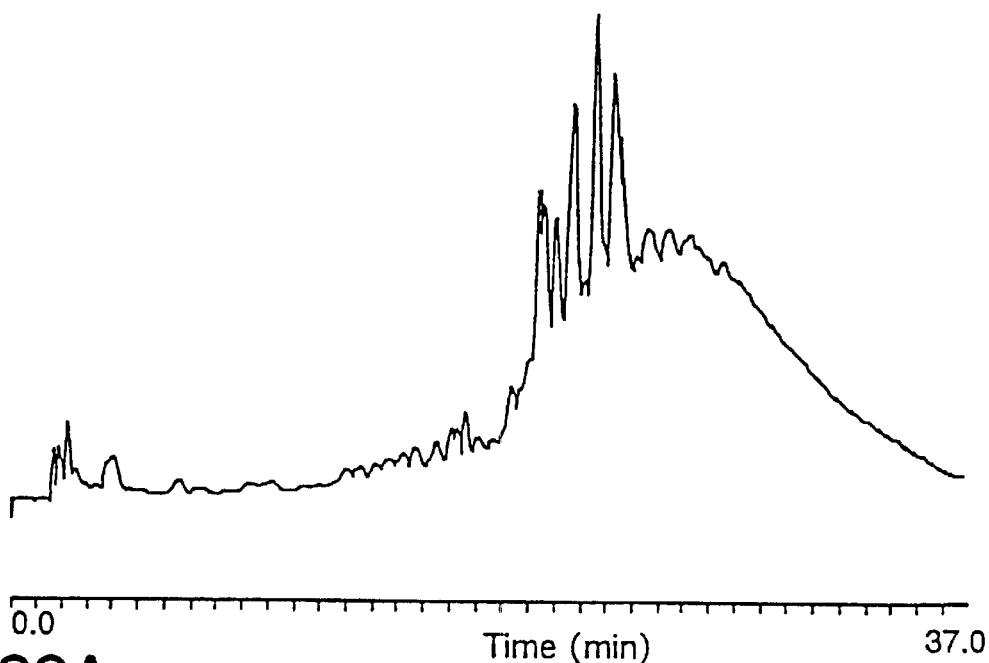
FIG. 29 illustrates a characterization of the parent array of synthetic analogues of the cCrk SH3 domain. A) Reverse phase HPLC analysis of the crude nine component protein array. B) MALDI mass spectrum of the same crude product mixture. The protein array contained predominantly full length polypeptide products. The presence of lower molecular weight species in the MALDI spectrum result from termination reactions during chemical synthesis. C) Treatment of the array with hydroxylamine produces the cleaved peptide products. Reverse phase HPLC of the mixture after chemical cleavage with $NH_2OH$ showed partial resolution of the 18 peptide fragments generated. D) MALDI mass spectrometry of the same cleaved mixture showed the characteristic patterns of cleavage fragments. The peaks marked (.)unambiguously identified the protein components present in the original mixture. The order of these peaks in the mass spectrum identifies the corresponding analogue in the parent array and defines the position of the analogue unit in the polypeptide sequence.
Figure 29C:
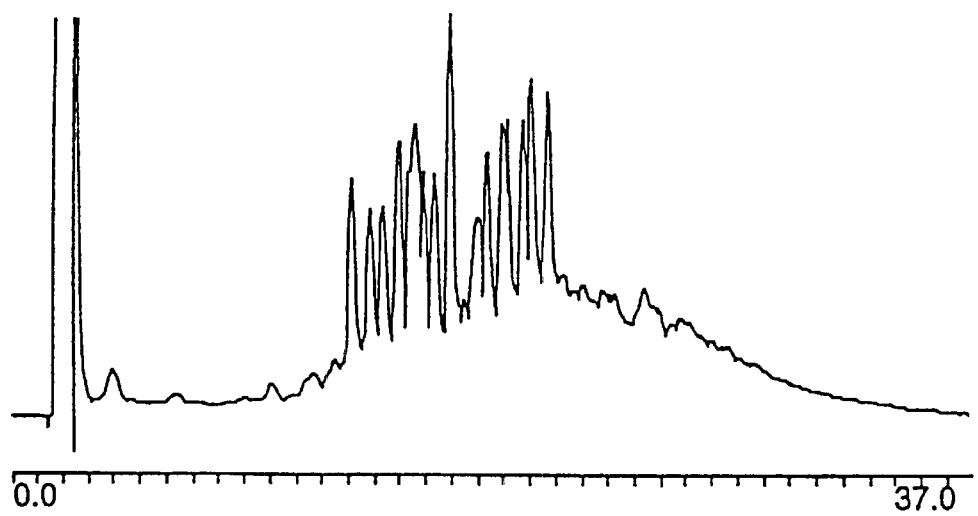
Figure 29B:
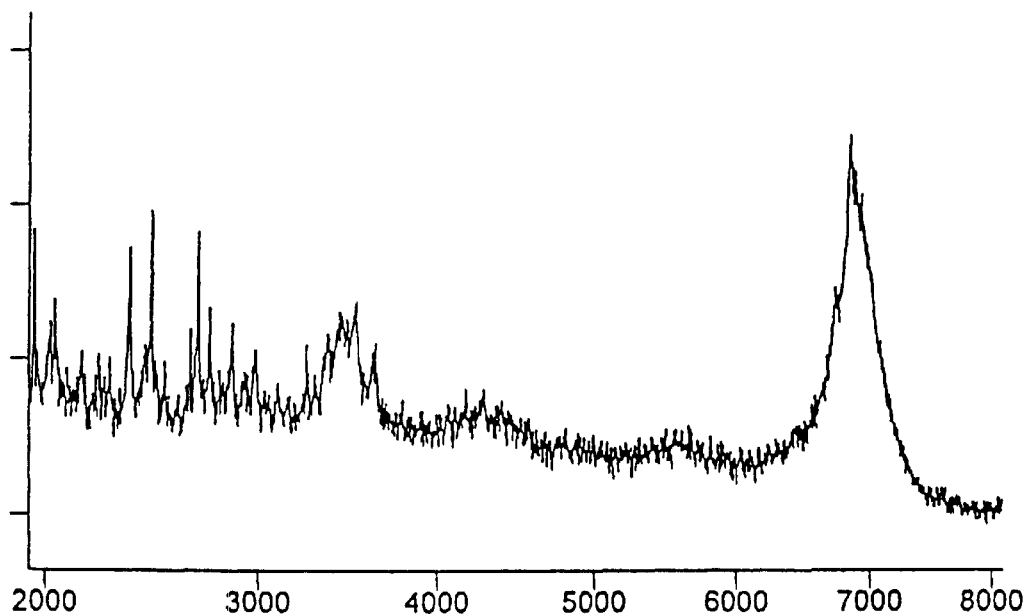
Figure 29D:
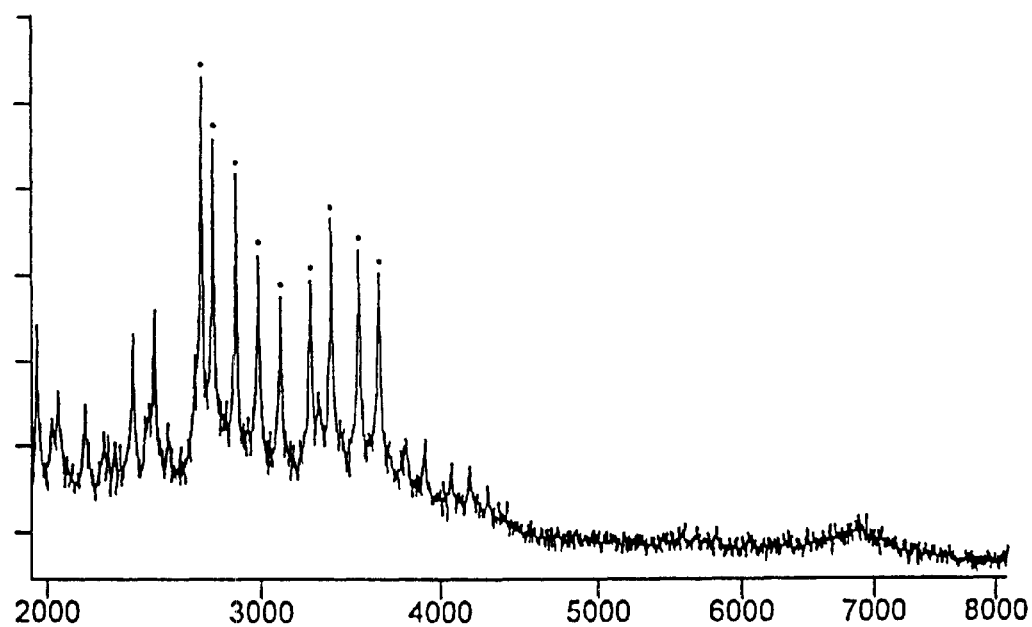

In order to characterize the protein array, the polypeptide chains were specifically cleaved with hydroxylamine through nucleophilic attack at the thioester bond. The resulting peptide fragments were analyzed by both HPLC and MALDI-TOF, FIGS. 29A' and 29B'. The treatment with hydroxylamine specifically cleaved each analogue-containing polypeptide chain at the site of modification, resulting in a mixture of peptide fragments. As shown in FIG. 23, the cleavage of the protein array produces a mixture of peptide fragments, each with a different number of amino acids in the peptide chain. As shown in FIG. 29A', reverse-phase HPLC analysis of the cleaved mixture yields complicated sets of partly unresolved peaks. In addition, the order of the peaks bears no direct relationship to the position of the analogue unit in the parent polypeptide chain. Analysis of the cleaved mixture by MALDI mass spectrometry, on the other hand, produces a series of well resolved peaks, the relative positions and masses of which are directly related to the position in which the analogue unit was placed in each full-length polypeptide chain. The peptide ladder shown in FIG. 29B' corresponded to all nine of the expected N-terminal peptide fragments resulting from cleavage of the nine protein analogues, and unambiguously characterized the protein array.

Since the cleavable bond was placed within the 58 residue SH3 polypeptide chain, the cleavage of each analogue must produce both N- and C-terminal peptide fragments. In the MALDI spectrum, however, only the N-terminal peptide fragments were observed with high intensity. The analysis of peptide mixtures by MALDI mass spectrometry can vary depending on the choice of matrix and solvent composition. This phenomena did not compromise our experimental results since the MALDI readout system relied on the comparison of mass spectra before and after selection. In addition, detection of only one of the two peptide fragments from each protein was required for identification of the parent protein analogue. In fact, interpretation can be simplified when only fragments corresponding to one end of the polypeptide chain are observed.

F. Affinity Chromatography of the Array of cCrk SH3 Protein Analogues

Figure 30:
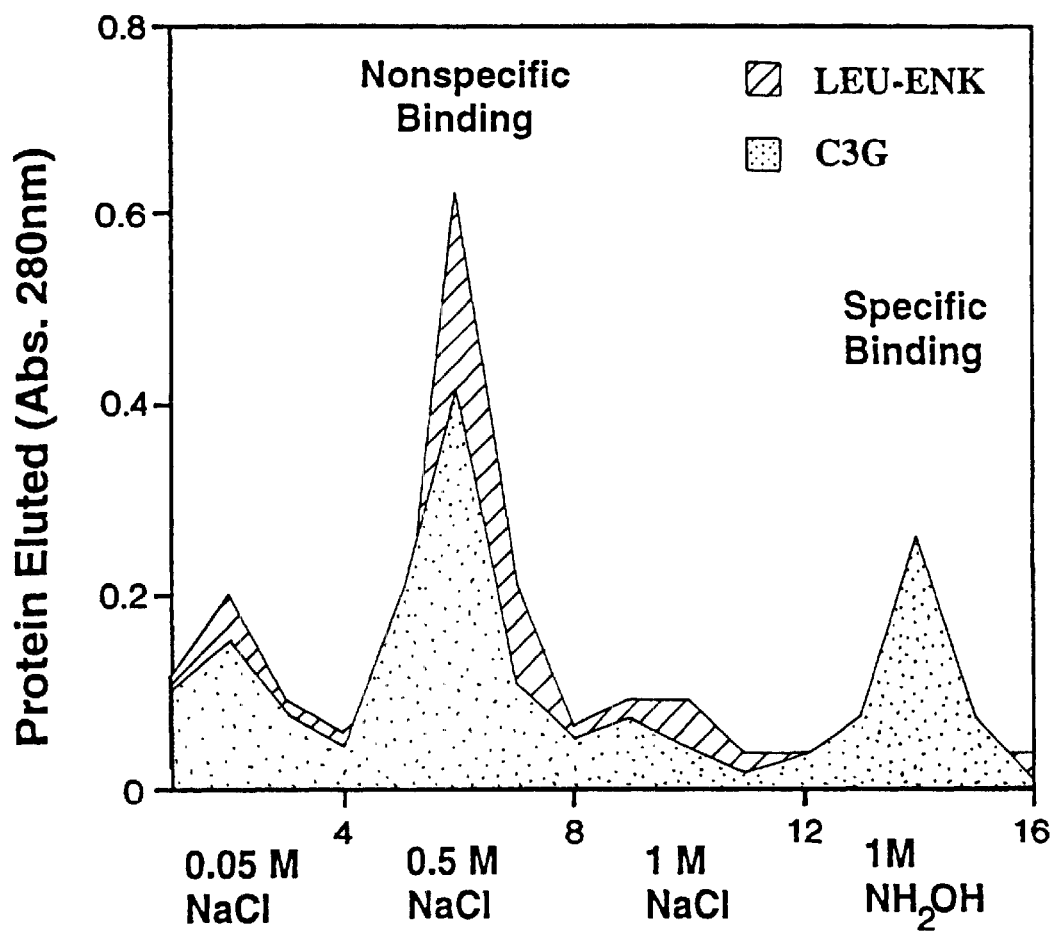
FIG. 30 illustrates affinity chromatography performed on the nine component cCrk SH3 domain protein analogue array as monitored by UV absorbance at 280 nm. The 0.5 M NaCl wash eluted all non-specific binding protein analogues as shown by absence of significant elution with 1 M NaCl. Protein analogues able to bind to the agarose-bound C3G derived synthetic peptide were then eluted by cleavage by hydroxylamine of the thioester bond in each polypeptide chain. This procedure resulted in a "functional selection" among the array of protein analogues, giving a binding pool and a non-binding pool. As a control, a column derivatized with a non-specific peptide, derived from [$Leu^5$] Enkephalin was substituted for the C3G column. As shown, in the hatched peaks, the entire SH3 protein array eluted with the 0.5 M NaCl wash and no specific binding was observed.

The lyophilized crude mixture of 58 residue polypeptide chain analogues was folded by dissolving 1.5 mg in 600 μL of 20 mM HEPES, 50 mM NaCl, pH 7.3.The dissolved protein array was then applied to the affinity column and left to bind for 6 hours. The column was then washed with 0.5 M NaCl buffer to remove nonspecific binding proteins from the column. Specifically bound protein analogues were then eluted with 1 M hydroxylamine bufffer. Amounts of eluted peptide were monitored by UV absorbance at 280 nm. This procedure was used for both the C3G peptide column and for the control column loaded with Ac-C-AcpYGGFL.amide. The hydroxylamine cleavage of the thioester bond results in the elution of peptide fragments corresponding to the proteins which were able to bind to the affinity column under these conditions. The results obtained are shown in FIG. 30. Specific binding was found only for the C3G peptide column.

G. Readout of the Composition of the Arrays of Protein Analogues

The composition of the parent array of SH3 protein analogues, as well as the binding and non-binding fractions obtained from affinity chromatography was determined by chemical cleavage and MALDI MS. First, the parent array of folded protein analogues and the 0.5 M NaCl wash from the affinity chromatography of the array were cleaved separately with hydroxylamine. After a desalting step, MALDI mass spectra were obtained for the peptide fragments generated from the (parent) protein array, the salt wash (non-binding) and for the peptide fragments generated by the hydroxylamine elution of the specifically bound analogues (binding). The results are shown in FIG. 26. Nine components were present in the array of protein analogues that was added to the C3G column as one mixture (FIG. 26A). Of these nine components, five did not bind significantly to the affinity column and were present only in the 0.5 M NaCl wash fractions (FIG. 26B). Three protein analogues, however, were able to bind to the C3G peptide on the column and were eluted only after cleavage with hydroxylamine (FIG. 26C). One of the protein analogues can be identified in both the wash and elution spectra, indicating intermediate folding and/or binding properties for this analogue.

The affinity assay used in this experiment did not allow binding effects to be distinguished from folding effects since lack of binding to the affinity column could arise either from failure to fold or from correctly folded material failing to bind. The observed pattern of functional and non-functional analogues covering the sequence 156–165 of cCrk indicated that in four of the nine positions even extensive modifications to the chemical structure of the polypeptide chain were not sufficient to prevent folding and specific ligand binding.

H. Discussion

The present invention is the first application of combinatorial synthetic chemistry techniques to a protein target. Straightforward synthetic access to protein arrays containing a dipeptide analogue Gly-SβAla has been demonstrated in the context of residues 156–165 of the cCrk N-terminal SH3 domain (residues 134–191) of cCrk. A latent readout functionality has been shown to be stable to conditions of protein folding and ligand binding, yet is cleavable by brief treatment with 1 M hydroxylamine. A selection for binding activity based on the use of a C3G-derived synthetic peptide for affinity chromatography has been developed and used to analyze the functional properties of the array of protein analogues. Finally, chemical cleavage of synthetically introduced latent cleavage sites followed by MALDI-TOF mass spectroscopy has been used to read out the composition of 'self-encoded' pools of protein analogues.

The analogue unit used in this study caused the simultaneous modification of several aspects of the covalent structure of the polypeptide chain. The Gly-SβAla dipeptide consisted of four alterations from the native dipeptide; two sidechain deletions, an extra methylene in the backbone and a thioester substituted for the amide bond. By redesigning the analogue unit in an iterative manner, further insight into the individual components of the modification can be elucidated. Although the thioester is needed for the self-encoding strategy used here, the other modifications can be deleted in the design of a new analogue unit. For example, using the dipeptide —NHCH$_2$CO—SCH$_2$CO— (Gly-SGly) as the analogue unit would investigate the role of the extra backbone methylene group. Alternatively, use of Aaa$_n$-SβAla as an analogue unit would reintroduce one sidechain of the two deleted. By designing new analogue units which differ from Gly-SβAla by a single modification, the contributions of individual modifications to the polypeptide structure may be investigated after repetition of the functional selection and decoding of the new functional and nonfunctional products.

To identify the individual components of the mixture of protein analogues after functional selection, a strategy has been developed in which the modified polypeptides are self-encoded. A cleavable bond was introduced into the polypeptide backbone at the site of modification. In the case of the analogue unit Gly-SβAla, the cleavable bond was a thioester which is stable to the conditions of normal handling, yet can be selectively cleaved by treatment with NH$_2$OH at neutral pH. Chemical cleavage of the thioester bond and subsequent analysis of the resulting peptide fragments by MALDI mass spectrometry, gave a series of peaks which unambiguously defined the protein components present in the array before cleavage. This encoding system is especially powerful since all the information is read out in a single step from a pool of molecules free in solution.

The qualitative nature of the MALDI mass spectrometric readout of signature analysis experiments may allow approximate measurements of binding affinities of individual protein analogues. One solution would be to vary the conditions of the functional selection to produce a series mass spectrometric signatures; for example, selecting the protein array against a series of affinity columns with increasing ligand concentrations. By monitoring the presence or absence of an individual mass spectrometric signal over a range of concentrations, an approximate Kd for the binding could be determined. Similar analyses could be performed by varying other parameters such as temperature and Gn.HCl concentration or through an affinity elution procedure.

The power of a chemical synthesis approach to the study of proteins is the straightforward access to a wide range of variations in molecular structure. In this invention, backbone interactions were studied by deletion of hydrogen bonding and by insertion of an extra methylene group. However, many other types of chemical modifications can be introduced using the methodology presented (supra). For example, further studies could investigate the ability of the protein to tolerate restrictions in backbone conformation; aminoisobutyric acid (α,α dimethyl glycine) residues are known to restrict Ramachandran space to alpha helical conformations (Marshall et al. Circ. Res., Suppl. II 30 and 31, 1972. 143–150) while insertion of beta turn mimics into the polypeptide chain can provide a test for such secondary structural features. The modifications possible using the tools of molecular biology are good for monitoring sidechain interactions but, with the exception of proline, do little to probe the conformational properties of the peptide backbone. The use of chemical synthesis allows for experiments which probe the tolerance of cis rather than trans peptide bond replacements and the ability of the peptide backbone to explore "D" Ramachandran space. Such experiments may give insight into the molecular characteristics of the peptide backbone. In this manner, the full range of modifications that have been used to elucidate the structure-function relationships of peptides can now be applied to proteins.

The signature analysis technique described in this example is generally applicable to proteins accessible by chemical synthesis (Muir et al. Curr. Opin. Biotech. 1993, 4, 420–427). With the introduction of modular chemical ligation techniques, individual domains, as well as series of these domains can be investigated in the context of larger protein molecules. Since these domains are the basic units of protein function, the systematic generation of arrays of analogues will allow the tools of organic chemistry to be used for the elucidation of the molecular basis of protein function.

EXAMPLE 3

(Illustrates a 20 Peptide Example of Chemical Synthesis, Functional Separation, and Readout (Protein Signature Analysis) of Self-encoded Arrays of an SH3 Domain with the Sequence)

In this example, the combinatorial protein signature analysis has been applied to the N-terminal SH3 domain from c-Crk. A total of 28 chemically defined protein analogues were analysed in only two protein signature analysis experiments. Using protein signature analysis, the effect on biological function of modifiying both amino acid sidechains and the polypeptide backbone of the protein was determined. The latter of these, i.e. systematic backbone engineering, is unprecedented in the study of proteins. Protein signature analysis provides a framework for the systematic application of chemistry to deciphering how proteins work, and thus complements the analogous chemical approaches already available for the study of nucleic acids (Min et al.(1996) J. Am. Chem. Soc. 118, 6116–6120). Consequently, fundamental biological processes such as protein folding, binding, and catalysis come under the scrutiny of synthetic organic chemistry.

Figure 20:
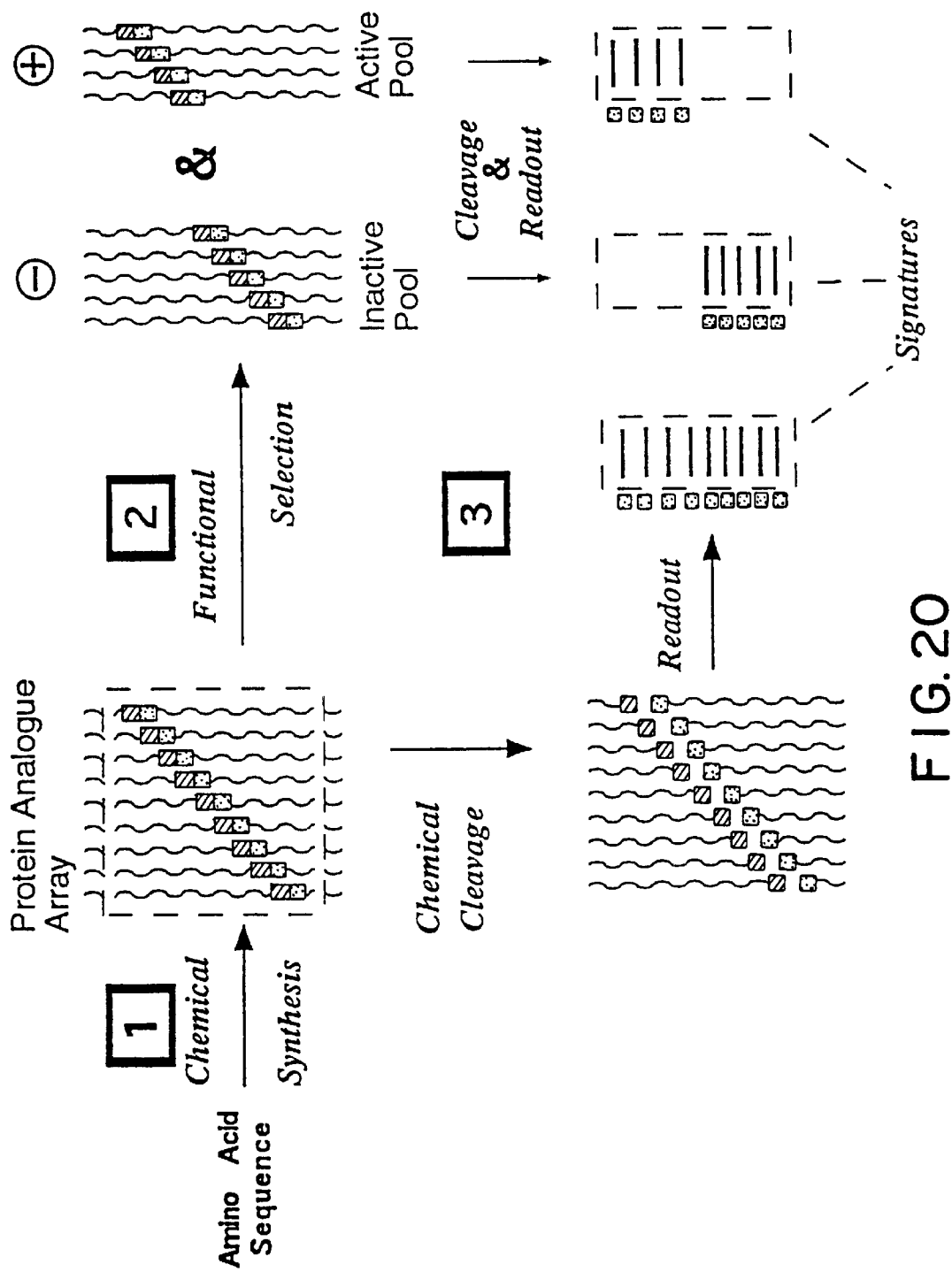
FIG. 20 illustrates the principle of protein signature analysis. [1] Total chemical synthesis is used to generate an array of protein molecules derived from a single amino acid sequence. An analogue chemical structure (represented by the the red-&-blue rectangles) is systematically incorporated at defined positions in the polypeptide chain. [2] The array of protein analogues is subjected to functional selection, resulting in separation into two populations: active and inactive. [3] The composition of each pool of analogues is then determined in a single step using a chemical readout system expressly built into the molecule for that purpose. This provides a signature relating the effects on function to substitution of the analogue structure throughout the region of interest in the protein molecule.

In the form shown in FIG. 20, protein signature analysis is a particularly useful way of looking at the chemical basis of ligand binding activity, from the viewpoint of the protein molecule.

As an example of this, we have applied protein signature analysis to one of the Src Homology 3 (SH3) binding domains commonly found in proteins involved in intracellular signal transduction.

SH3 domains are small protein modules: polypeptide chains of about 60 amino acid residues that fold to form a unique three dimensional structure, even outside the context of the longer polypeptide chain in the parent protein. It is now well established that SH3 domains mediate protein-protein interactions through the recognition of short proline-rich sequences.

Our goal was to investigate the chemical basis of the interaction between the N-terminal SH3 domain from the cellular adaptor protein, c-Crk (residues 134–191 of the murine sequence), and its target ligand, a proline-rich peptide from the guanine nucleotide exchange protein, C3G. We wanted to change the chemical structure of the SH3 polypeptide chain and observe how this affected the functional properties of the domain.

We decided to introduce a dramatic perturbation in the chemical structure of the protein molecule: deletion of the side chains of two adjacent amino acids in concert with the introduction of an extra backbone methylene. A thioester bond was also introduced to facilitate the identification of protein analogues (see below). The resulting Gly-[COS]-βAla dipeptide analogue unit can be compared with a native dipeptide sequence (see FIG. 22A).

A Synthesis of an Array of SH3 Analogues

Figure 1:
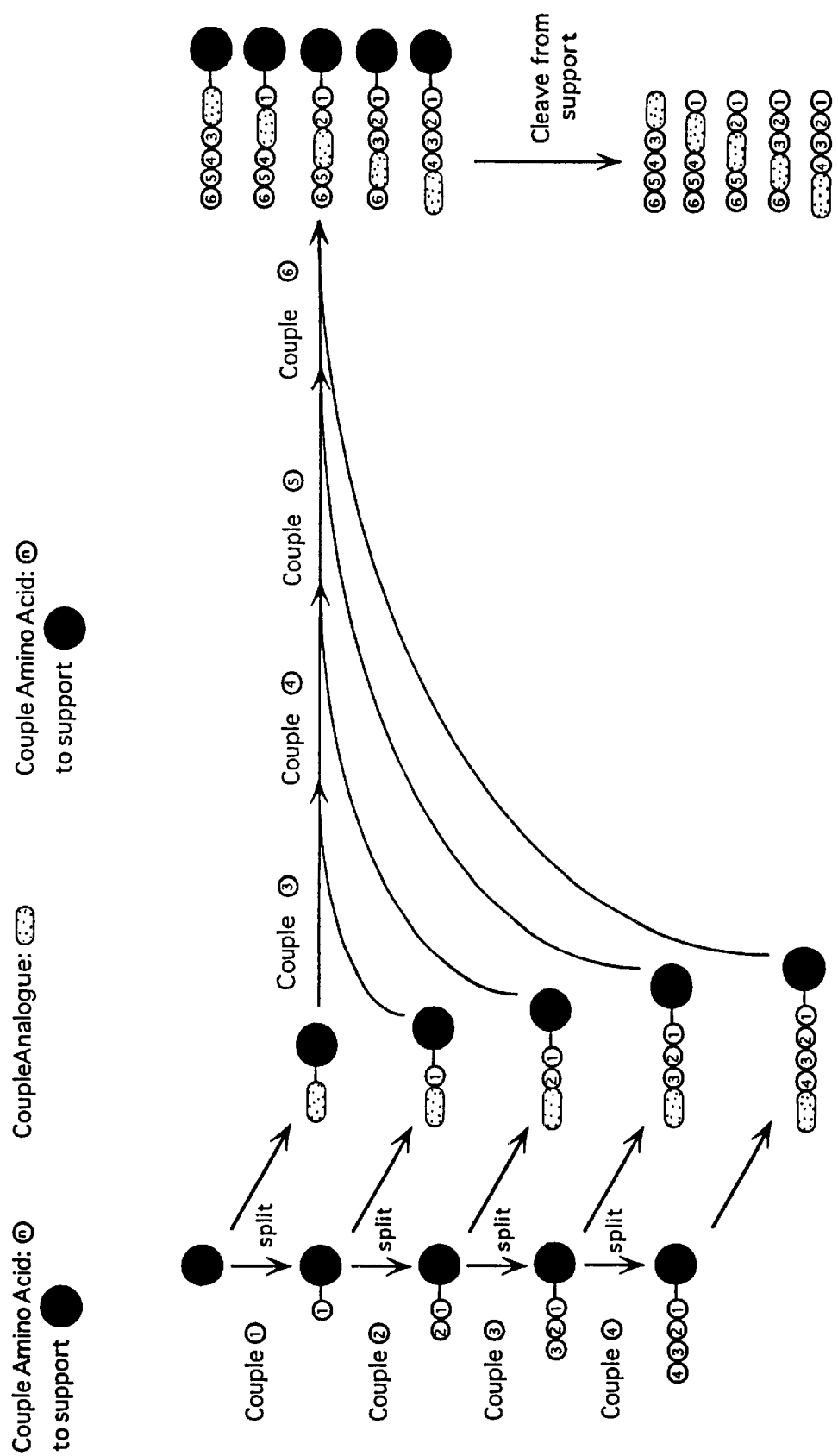
FIG. 1 represents the solid-phase peptide synthesis strategy used to scan a synthetic marker (dark oval) through sequential dipeptide units in a polypeptide sequence. Each member of the resulting peptide family contains a single copy of the marker at a unique dipeptide site. By splitting and subsequently recombining the peptide-resin, all the members of the polypeptide family can be generated in a single synthesis. A modified solid phase peptide synthesis methodology has been developed that makes it possible to prepare all members of the array of protein analogues concurrently in the course of a single synthesis. This simple procedure involves the use of two reaction vessels. At each stage of the synthesis a small aliquot of the peptide-resin is removed from the first vessel, and the analogue moiety attached to the growing peptide chain. The resin aliquot is then transferred to the second reaction vessel and the remainder of the amino acids in the sequence are coupled. Continual siphoning of resin aliquots from vessel #1 into vessel #2 (with analogue attachment in between), results in the generation of the complete protein array as a single product mixture. Use of this split-resin procedure ensures that each component of the array contains only a single copy of the analogue at a unique and defined position. The synthetic marker can be designed to probe the importance to structure and function of side-chain atoms, backbone atoms or both.
Figure 2:
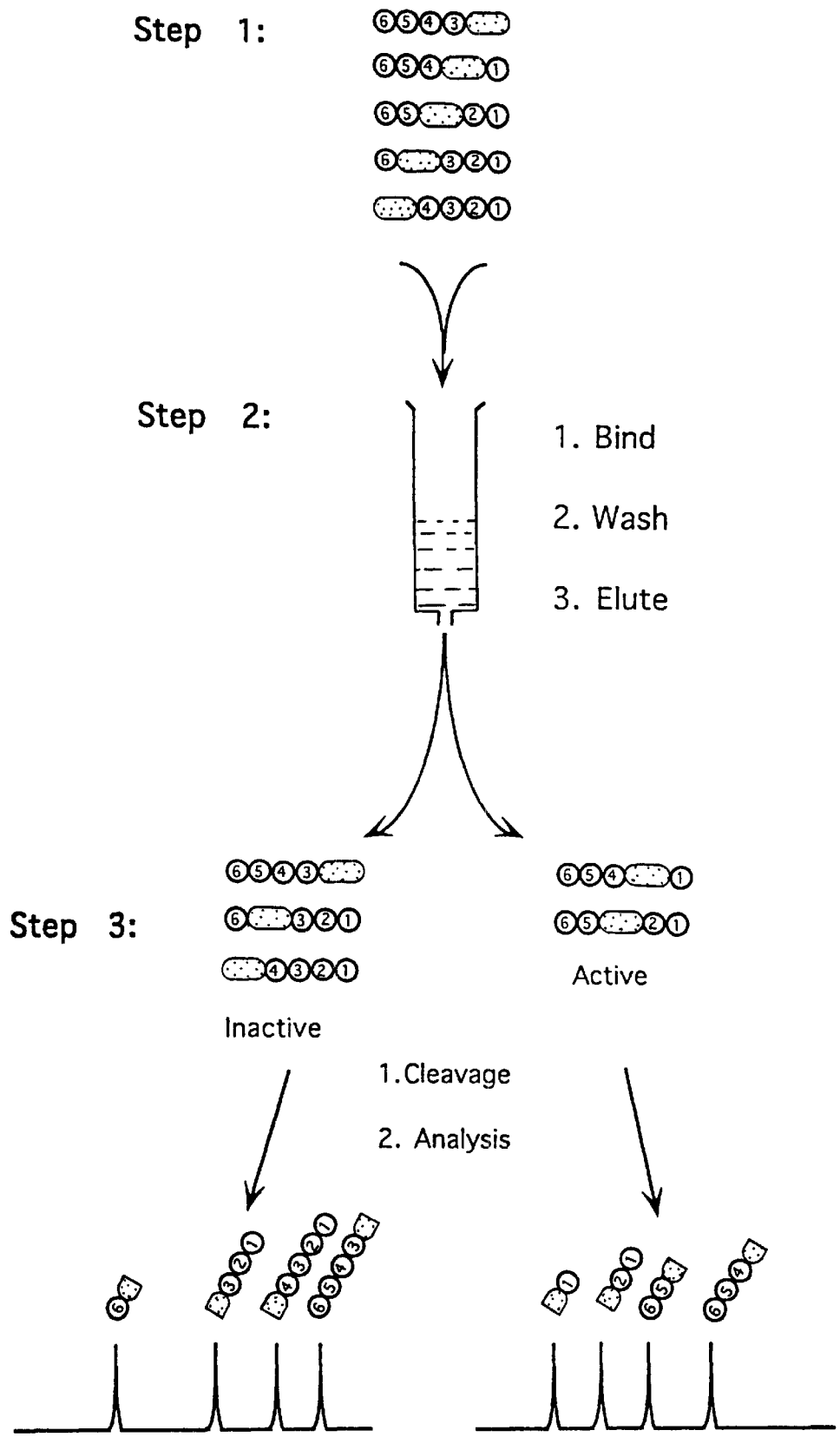
FIG. 2 represents a one experiment cycle of iterative signature analysis. Multiple rounds of this cycle can be performed with the information from previous cycles being incoroporated into each successive iteration.
Figure 3A:
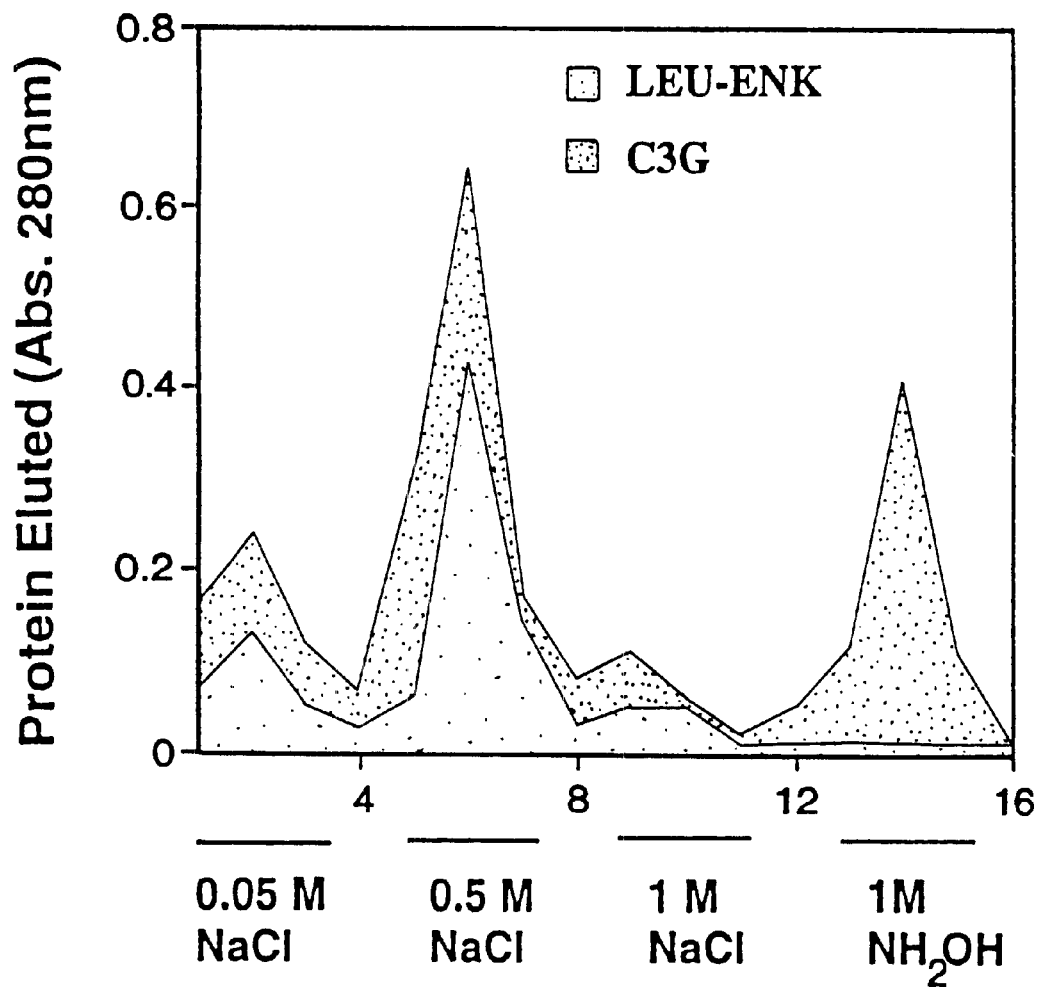
FIG. 3 illustrates preliminary iterative signature analysis data on residues 156–165 of the peptide Crk-N. a) Represents a comparison of the elution profiles obtained for the protein family using a C3G-peptide agarose column and a Leucine-Enkephalin agarose column (control). Note that purified synthetic Crk-N binds the C33G-peptide in solution with a $K_D$ of 2.3 $\mu$M (recombinant Crk-N=1.9 $\mu$M). b) Represents HPLC profiles (all 25–45% acetonitrile over 30 minutes) obtained from the high salt was (non specific) and ammonium acetate wash (specific) for the two columns. c) Represents the theoretical masses of peptide fragments produced upon ammonium acetate cleavage of a Crk-N family. Single letters refer to amino acid pairs substituted with the -Gly-SCH$_2$CH$_2$CO— marker. d) Comparison of the MALDI MS spectra of the ammonium acetate wash and the entire 9 component synthetic Crk-N family cleaved with ammonium acetate. In both cases the N-terminal peptide ladder is observed at a much higher intensity than the equimolar C-terminal peptide ladder.

We initially focused on a sequence of twenty amino acids near the middle of the SH3 polypeptide chain, the region c-Crk(146–165). As a first step an array of nineteen protein analogues was chemically synthesized by placing the Gly-[COS]-βAla dipeptide unit at each possible dipeptide position within the twenty amino acid stretch. In this synthesis, we used the modified stepwise solid phase peptide synthesis (SPPS) approach that is described in examples 1 and 2 (supra). This method made it possible to prepare all members of this array of analogues simultaneously in the course of a single synthesis (see FIG. 1). This modified split-resin procedure ensured that each individual polypeptide chain in the final product mixture contained only one analogue unit at a single defined position. Stepwise synthesis of the full-length 58 residue SH3 domain polypeptide, with the introduction of a chemical perturbation at nineteen defined positions of the polypeptide chain according to such a split-resin process, gave an array of analogues as a single product mixture containing the nineteen desired molecular species.

B. Functional Selection by Affinity Chromatography

The next task was to subject these synthetic products to functional selection. The N-terminal SH3 domain from c-Crk specifically recognizes a ten residue proline-rich sequence from the protein, C3G. A synthetic peptide containing the proline-rich C3G sequence was covalently immobilized on commercially available derivatized agarose beads. In preliminary experiments, a synthetic SH3 domain corresponding to the wild-type sequence was found to bind specifically to the C3G peptide affinity column; prolonged washing with high salt buffer did not elute the synthetic SH3 protein, whereas the use of stronger conditions that disrupt the specific interactions, in this case 6M guanidine.HCl, led to elution of the protein with ~85% recovery of the applied material. No specific binding of the synthetic c-Crk SH3 domain to a control affinity column containing leucine enkephalin was observed. These procedures have previously been described in example 2 (supra).

Having established the validity of the affinity column assay, the effects of the dipeptide analogue units on the binding properties of the SH3 domain were evaluated. The nineteen member array of synthetic analogues of the 58 residue domain was passed as one pool over the C3G peptide affinity column, giving rise to binding and non-binding populations.

C. Readout of Self-encoded Arrays of Protein Analogues

Figure 24:
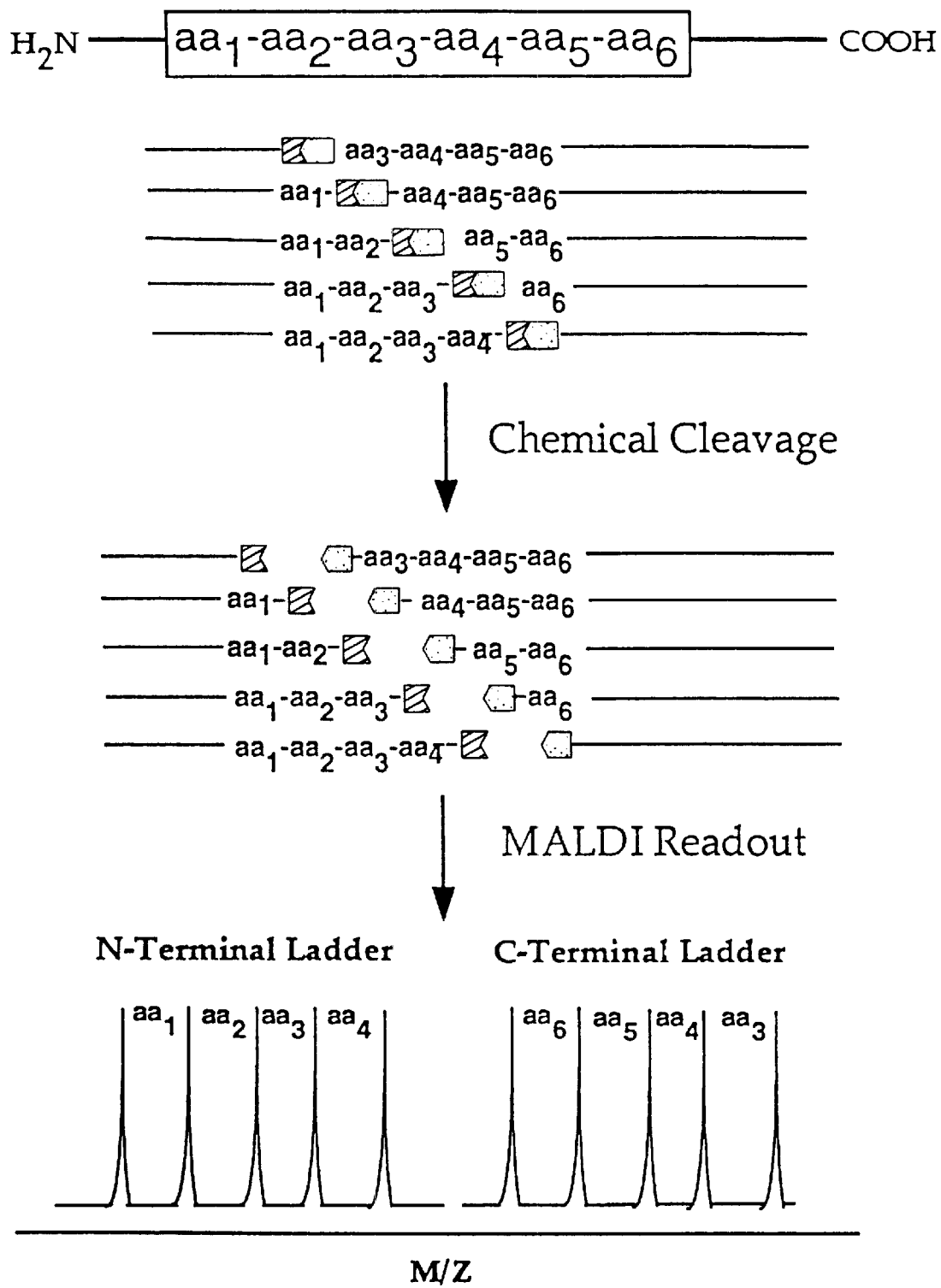
FIG. 24 illustrates a combinatorial Readout of Protein Analogue Arrays. Building a latent chemical cleavage site into the analogue unit (rectangle) means that each protein in the array will contain this chemical marker at a unique position in the polypeptide sequence. Chemical cleavage specifically at the analogue unit gives rise to characteristic peptide fragments, each with a unique mass indicative of the position of the anlogue unit within the sequence of the original protein analogue. Each protein analogue in an array is thus self-encoded. Readout of these decoded peptide fragments can then be performed, in one operation, using MALDI mass spectrometry.

The third and final step was then to determine which protein analogues were present in each of the two pools. The identification of individual molecular species in a pool of closely related protein analogues is a formidable analytical challenge. One way to determine the molecular composition of such a mixture of protein analogues is to combine mass spectrometry with the synthetic chemistry approach, as schematically illustrated in FIG. 24.

The readout of all members of each pool of protein analogues was accomplished in a single step using a chemical decoding approach, similar in concept to that already described for use with nucleic acid libraries (supra). A latent readout chemistry was built into each molecule in the course of the preparation of the protein array by total chemical synthesis.

The analogue unit contained a unique thioester chemical cleavage site which allowed us to chemoselectively 'unzip' (see FIG. 22B) the mixture of analogue polypeptide chains found in a particular pool, binding or non-binding. When examined by matrix assisted laser desorption ionization (MALDI) mass spectrometry (Chait, B. T. & Kent, S. B. H. (1992). Weighing naked proteins: Practical high accuracy mass measurement of peptides and proteins. *Science* 257, 1885–1894), the resulting sets of 'decoded' peptide fragments gave characteristic signatures that could be interpreted as follows. Each component of the mass spectrometric signature reflected the presence of the corresponding full-length polypeptide chain (containing the analogue unit) in that pool of intact protein analogues. Furthermore, the position of the analogue unit in the original 58 residue c-Crk SH3 protein analogue was defined by the position of the corresponding signal in the mass spectrometric signature, as schematically illustrated in FIG. 24 (Chait et al. (1993) *Science* 262, 89–92; Zhao et al. (1996) *Proc. Natl. Acad. Sci. USA* 93, 4020–402).

E. Role of SH3 Backbone

The three components of protein signature analysis-synthesis, selection, and readout—have previously been described in detail in a series of model studies (examples 1 and 2 supra). Here we have applied them to an SH3 domain in order to elucidate the chemical basis of ligand binding. The results obtained from applying functional selection/chemical readout to the 19-member array of protein analogues corresponding to the N-terminal SH3 domain from c-Crk are shown in FIG. 25. The mixture of synthetic protein analogues was passed over a C3G-peptide affinity column, to assay for binding activity. The signature of the parent array of protein analogues (FIG. 25B) is compared with the signature of the pool that showed binding activity (FIG. 25C).

Eight (out of nineteen) members of the array of protein analogues bound to the C3G peptide. Perhaps of most interest was the pattern of binding and non-binding observed for proteins modified within the c-Crk(146–152) region. This sequence of the SH3 protein corresponds to the so called 'RT loop', a region known to be involved in ligand binding throughout the SH3 domain family. The sequence of this part of the c-Crk SH3 polypeptide is: [-Asn$^{146}$-Asp-Glu-Glu-Asp-Leu-Pro$^{152}$- ] (SEQ ID NO 17). It is evident from the signature of the functional pool of SH3 analogues (FIG. 25C) that binding to the C3G-derived peptide ligand occurred even when the side chains of the Asp$^{147}$ or Glu$^{149}$ residues in the SH3 domain had been removed. Thus, interaction with the Asp$^{147}$ or Glu$^{149}$ side chain carboxyls was not essential for binding (note that the effect of the replacement of these two residues on binding specificity cannot be inferred from this experiment). In contrast, removal of the side chain of Asp$^{150}$ by substitution with either the Gly or βAla portion of the dipeptide analogue unit virtually eliminated binding; restoration of Asp$^{150}$ restored binding. It should be noted that Asp$^{147}$ and Asp$^{150}$ are both conserved in the viral form of the protein, v-Crk, whereas Glu$^{149}$ is replaced with a glycine residue (Mayer et al. (1993) *J. Virol.* 64, 3581–3589).

Figure 31:
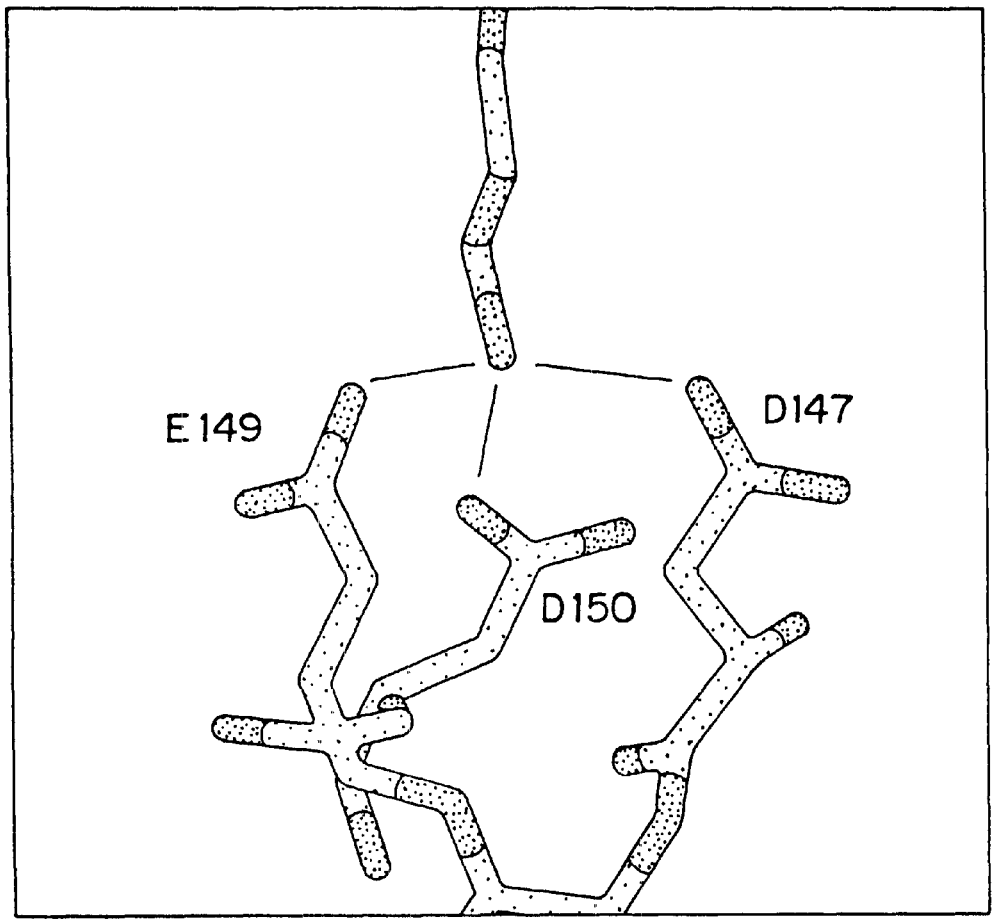
FIG. 31 illustrates a region of the three-dimensional structure of the c-Crk-C3G complex, showing the three acidic residues within the RT loop of the SH3 domain interacting with $Lys^8$ of the bound C3G peptide ligand. [Taken from a crystal structure]. These interactions are believed to make an important contribution to binding, and to play a critical role in orienting the interaction of c-Crk with C3G.

These data are intriguing and offer experimental support for a difference in the roles of the three acidic side chains in ligand binding, as previously suggested by the X-ray crystallographic data (Wu, X., et al. (1995) *Structure* 3, 215–226.). As shown in FIG. 31, all three of the side chain carboxylate functionalities in residues Asp$^{147}$, Glu$^{149}$, and Asp$^{150}$ of the c-Crk SH3 domain make specific interactions with the side chain —$^6$NH$_{3+}$, of Lys$^8$ in the ligand. From the protein signature analysis results presented here we can infer that the primary determinant of binding in this region of the SH3 molecule is the Asp$^{150}$ side chain carboxylate.

The interaction of Asp$^{147}$ and Glu$^{149}$ side chains with the ligand peptide may play a different role, perhaps affecting the specificity of binding by discriminating between Lys and Arg side chains at this position. The predominant role of Asp$^{150}$ and the different roles of Asp$^{147}$ and Glu$^{149}$ were both suggested by the crystallography data. In the crystal structure, the —εNH$_{3+}$— group of the lysine residue (in the Pro-rich peptide ligand) forms a hydrogen bond to an oxygen atom in the side-chain carboxylate of Asp$^{150}$, using the preferred syn orientation of the oxygen lone electron pair as shown (FIG. 31), whereas the hydrogen bonds to Asp$^{147}$ and Glu$^{149}$ are in the less favoured anti orientation.

The signature analysis data shown in FIG. 25C are consistent with this crystallographic observation, because replacement of Asp$^{150}$ resulted in gross loss of binding activity, whereas replacement of Asp$^{147}$ or Glu$^{149}$ did not.

Productive application of the signature analysis approach does not require knowledge of the three dimensional structure of a protein domain. However, the three dimensional structure can be used together with protein signature analysis to give additional insights into the chemical basis of protein function. In the example given here, the combination of signature analysis data with structural studies gave a more informative interpretation of the molecular basis of ligand binding than would have been possible with protein signature data alone. These results also show the potential of the protein signature analysis technique to illuminate the chemical reality of mechanisms suggested by the structural data.

F. Role of SH3 Backbone

As shown in FIG. 25, eight of the 19 protein analogues displayed binding activity, while eleven were inactive. We have discussed the implications of these observations for the roles of specific amino acid side chains (above). How can we relate this data to other aspects of the chemical basis of the binding function of the SH3 domain? The non-functional members of the array of protein analogues could owe their inactivity to any or all of the following factors: deletion of amino acid side chains; insertion of an extra methylene in the polypeptide backbone; or, deletion of the H-bonding ability of the central amide moiety in the analogue structure. Information bearing on these possibilities can be simply obtained by making another array containing alternative analogue structures covering the region of interest in the SH3 domain.

Figure 27A:
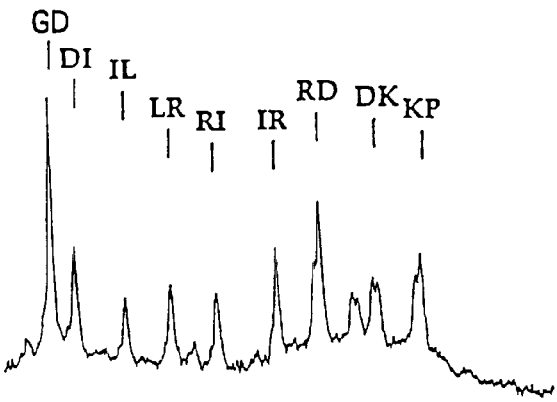
FIG. 27 illustrates an iterative protein signature analysis applied to the N-terminal SH3 domain of murine c-Crk. (Top) The amino acid sequence of the 58 residue polypeptide chain is shown. Protein signature analysis was used to study how chemical variation of the centrally-located ten residue region (highlighted residues 156–165) affected C3G peptide binding. Two rounds of signature analysis were performed, using different dipeptide analogue units. A. Round 1. Signature of the active (binding) pool obtained from the nine-membered array of Gly-[COS]-Gly-containing protein analogues. In contrast to the previous experiment, analysis of this signature reveals that all nine protein analogues were present in the binding pool. B. Round 2. Signature of the active (binding) pool resulting from passing the parent array of Gly-[COS]-βAla-containing protein analogues over a C3G-derived synthetic peptide affinity column. The signature data shown represents an expansion of the larger signature shown in FIG. 25C. Only four dipeptide sequences out of a total of nine ($I^{161}R^{162}$; $R^{162}D^{163}$; $D^{163}K^{164}$; and, $K^{164}P^{165}$) in this region, could be replaced by Gly-[COS]-βAla without significant loss of binding activity (SEQ ID NO 37).
Figure 27B:
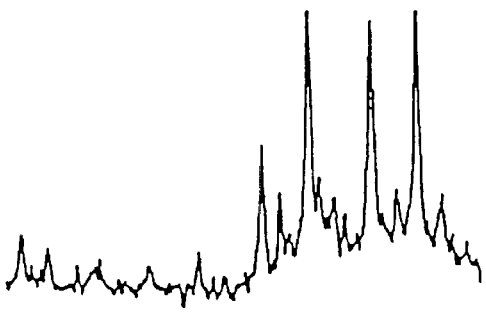

In this case, we made a second nine-membered array to the region cCrk(156–165) using —Gly—[COS]-Gly- as an analogue unit in which the additional methylene of the original analogue unit was not present (FIG. 22A):

The signature obtained after functional separation, based on binding to the Pro-rich C3G peptide affinity column, and readout of this new nine-membered array of protein analogues is shown in FIG. 27. The signature in FIG. 27B represents an expansion of the signature data shown in FIG. 25C, but focussing on the region corresponding to replacement of residues 156–165 of the SH3 domain by the Gly-[COS]-βAla analogue. Of the nine Gly-[COS]-βAla-containing SH3 analogues in this region, only four bound to the C3G peptide affinity column. The other five analogues did not bind under the conditions used. This pattern is identical to that observed for this region in a data set in which only these nine anlogues were analysed (example 2; supra).

Figure 32:
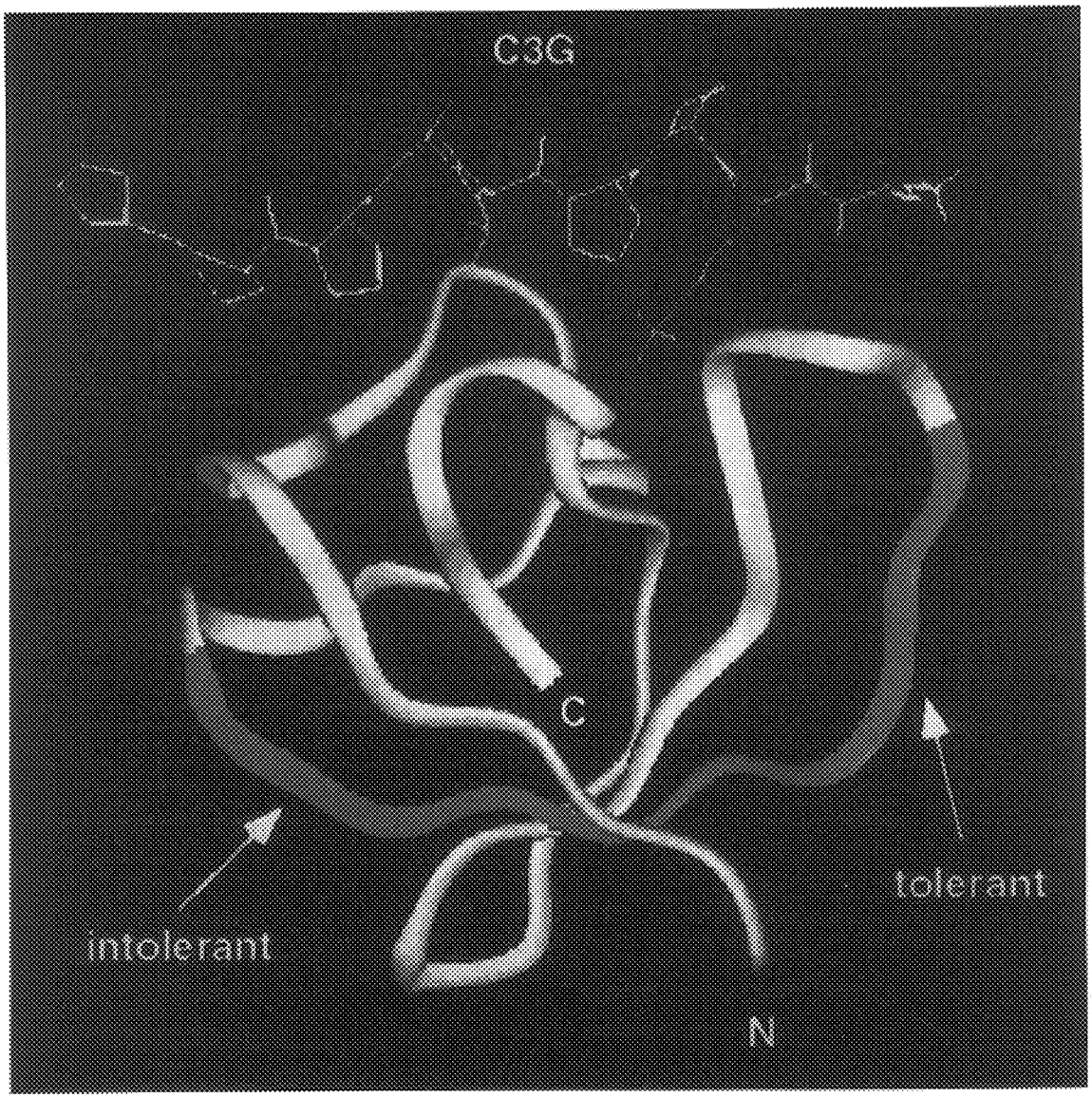
FIG. 32 illustrates results from two rounds of protein signature analysis of the sequence comprising residues 156–165 superimposed on the crystal structure of the N-terminal c-Crk SH3 domain complexed to the proline rich C3G peptide. Indicated are those regions of the polypeptide chain observed to be either tolerant (green) or intolerant (red) of an extra backbone methylene group
Figure 33:
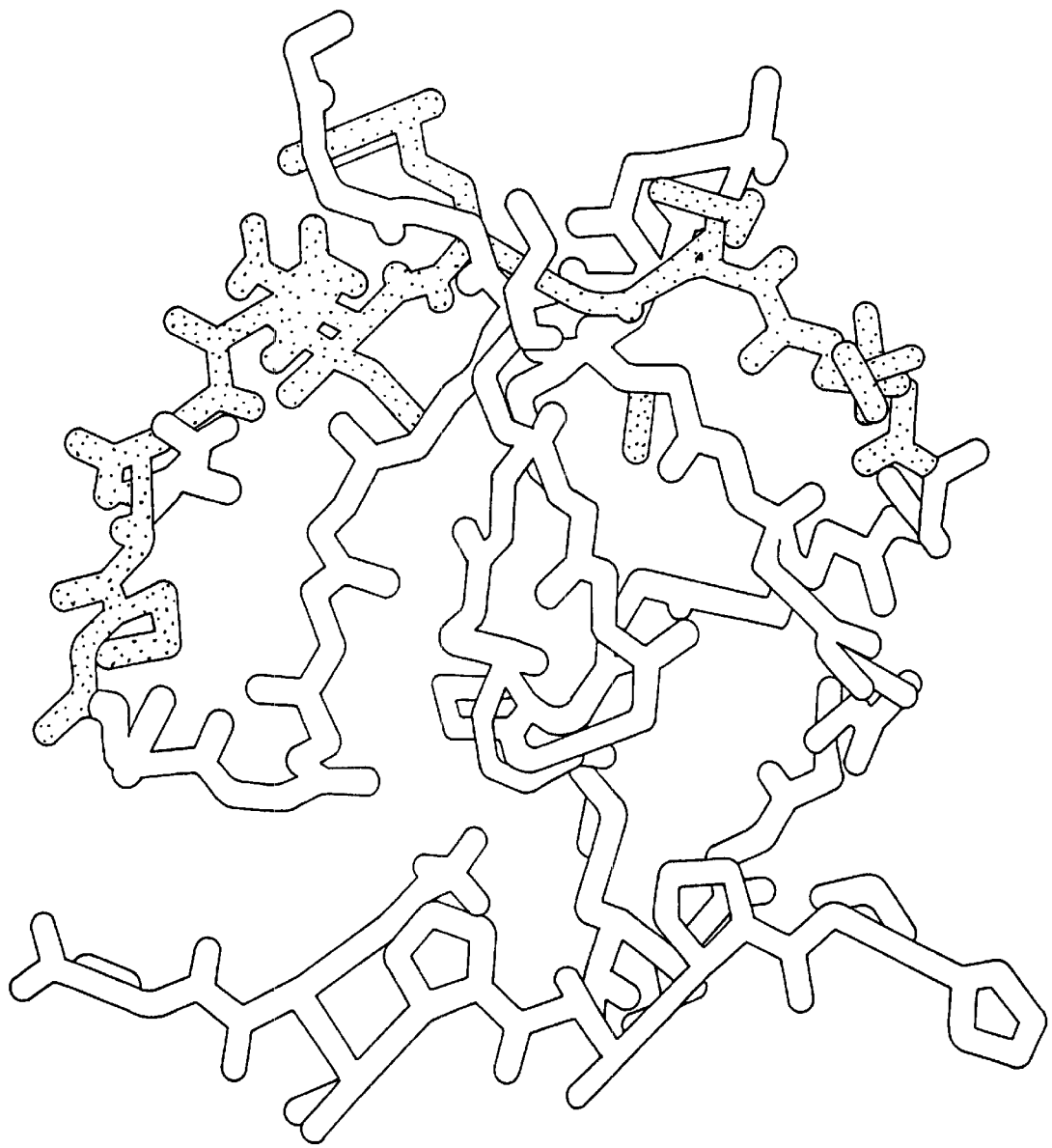
FIG. 33 represents a computer generated model of the SH3 domain. The green+red regions represent the perturbed sites of a peptide ladder fragment from a section of the SH-3 domain. The green molecular region represents that a perturbation in this region has no effect on the activity with the ligand which is depicted in yellow. The red molecular region represents that a perturbation of this region destroys activity with the ligand. The gray region represents the remaining unperturbed (unanalyzed) regions of the SH3 domain. The yellow molecular region represents a proline rich peptide ligand.

By contrast, all nine (-Gly-[COS]-Gly-) containing protein analogues exhibited appreciable binding activity in an identical assay (FIG. 27A). That so many of the protein analogues retained specific binding activity is a remarkable result, given the very substantial nature of the chemical changes made in the polypeptide chain. The data show that neither the pairwise deletion of side chains nor deletion of the H-bond in the central amide moiety of the analogue structure was responsible for the lack of binding exhibited by the five inactive members of the original -Gly-[COS]-βAla-containing array of protein analogues covering this region. Rather, it can be inferred from comparison of the two sets of data that the observed lack of binding activity was caused by insertion of the extra methylene in the polypeptide backbone by the original analogue unit. Thus, it appears that the region defined by residues c-Crk(156–161) is less tolerant to backbone engineering than the region defined by residues c-Crk (161–165) (FIG. 32). The affinity binding assay used does not discriminate between a gross structural pertubation and a purely functional effect, since both could result in a loss of activity. However, none of the amino acids in the region being studied (residues 156–165) interact directly with the ligand, suggesting that the observed effects may be structural in origin.

MATERIALS AND METHODS

General

Analytical HPLC was performed on a Hewlett-Packard 1050 system with 214 nm detection using a Vydac C18 column (5 μm, 4.6×150 mm) at a flow rate of 1 mL/min. All runs used a linear 0%–67%B gradient where buffer A was 0.1% TFA in $H_2O$ and buffer B was 90% acetonitrile, 10% $H_2O$, 0.09% TFA. Electrospray mass spectrometric analysis of all synthetic peptides was performed on a Sciex API-III triple quadrupole electrospray mass spectrometer. Calculated masses were obtained using the program MacProMass (Sunil Vemuri and Terry Lee, City of Hope, Duarte, Calif.); Buffer B was 90% acetonitrile, 10% $H_2O$, 0.09% TFA. Semipreparative HPLC was performed on a Rainin HPXL dual pump system using a Vydac C18 column (10 μm, 10×250 mm) at 3 mL/min with detection on a Dynamax UV detector.

Matrix-Assisted Laser Desorption Ionization Mass Spectrometry (MALDI) (Example 1)

Mass spectra were recorded using a Vestec Model VT 2000 laser desorption, linear time-of-flight mass spectrometer. Samples were desorbed/ionized using the focused output of a 355 nm frequency tripled Lumonics Model HY 400 Nd:YAG laser (Lumonics, Kanata, ON, Canada). Ions were accelerated through a dual-stage source to a total potential of 30 keV and detected by a 20-stage focused mesh All spectra were acquired in the positive ion mode and summed over 50 laser pulses. Time-to-mass conversion was accomplished by internal calibration using the $[M+H]^+$ and $[M+2H]^{+2}$ ion signals from a standard peptide (MW 2419.1 Da). Samples were prepared by dissolving the crude peptide array in 1:1 acetonitrile:$H_2O$, 0.1% TFA to a concentration of 1–10 μM per peptide component. 2 μL of this solution was mixed with 5 μL of a saturated solution of 2,5-dihydroxybenzoic acid (DHB) in the same solvent. Ultimately, 2 μL of this mixture containing ~1–10 pmoles of each peptide component was added to a stainless steel probe tip (3.14 $mm^2$.) and the solvent allowed to evaporate under ambient conditions.

Solid Phase Peptide Synthesis (Example 1)

Except where noted, all peptides were synthesized manually according to the in situ neutralization/HBTU activation protocol for Boc solid phase synthesis as previously described (Schnölzer et al. *Int. J. Pept. Protein Res.* 1992, 40, 180–193). The peptides were synthesized on (4-Me) benzhydrylamine-copoly(styrene-1% DVB)-resin (Peninsula Laboratories, 0.93 mmol/g) which after HF cleavage gives the C-terminal amide. The peptides were deprotected and cleaved from the resin by treatment with 10 mL HF, containing 5% anisole, for one hour at 0° C. After evaporation of the HF, the crude peptide product was precipitated and washed with diethyl ether, dissolved in 1:1 Acetonitrile/$H_2O$ containing 0.1% TFA, and lyophilized.

Synthesis of Boc-Gly-$SCH_2CH_2$COOH (Example 1)

Synthesis of Boc-Gly-$SCH_2CH_2$COOH was based on a previously published procedure (Hojo et al. *Bull. Chem. Soc. Jpn.* 1991, 64, 111–117). To a solution of Boc-Gly-OSuc (1.36 g, 5 mmol; Sigma) dissolved in 50 mL $CH_2Cl_2$, 3-mercaptopropionic acid (0.5 g, 5 mmol; Aldrich) and N,N-diisopropylethylamine (DIEA; Sigma) (1.0 g, 7.5 mmol) were added, and the resulting solution was stirred at room temperature for 15 hours. The solvent was reduced by evaporation under reduced pressure and the resulting oil was dissolved in ethyl acetate. After two washes with 0.1 M HCl and four washes with saturated aqueous NaCl, the ethyl acetate layer was dried over magnesium sulfate. Following concentration, the resulting oil was dissolved in 40 mL diethyl ether. Dicyclohexylamine(DCHA) (4.5 mmol, 1 g) was added dropwise, giving crystals which were recrystallized from hot ethyl acetate. The DCHA salt was suspended in ethyl acetate and extracted with 0.05 M citric acid. After three washes with saturated NaCl, the ethylacetate layer was dried over magnesium sulfate. After the solution was filtered and concentrated, trituration with hexane gave Boc-Gly-$SCH_2CH_2$COOH as a solid (750 mg, 62%) FAB MS for $C_{10}H_{16}O_5N_1S_1Na_1$, MW obsv: 286.0728 Da, calc: 286.0725; melting point 103°–105° C. (104°–106°).

Synthesis of the Nine Component Peptide Analogue Array of the Parent Sequence PFKK-[GDILRIRDKP]-EEAcpRLKLKAR (SEQ ID NO 7) (Example 1)

The sequence EEAcpRLKLKAR (SEQ ID NO 5) was synthesized in reaction vessel A, FIG. 4, on 0.1 mmol MBHA resin. Onto this sequence, an array of nine Gly-SβAla substituted peptide analogues was synthesized through the sequence GDILRIRDKP (SEQ ID NO 4) using the protocol described below. Boc-Gly-SCH$_2$CH$_2$COOH (0.25 mmol, 66 mg) was preactivated for one hour with DIC (0.25 mmol, 39 μL; Aldrich) and HOBt (0.25 mmol, 34 mg; Aldrich) in 600 μL DMF (~0.4 M; Aldrich), and used for five consecutive cycles (125 μL/cycle), after which a second 0.25 mmol of the dipeptide analogue was activated under the same conditions and used for the remaining four cycles.

Cycle 1

First, the N$^\alpha$-Boc deprotected peptide-resin (0.10 mmol) was suspended in 10 mL DMF. One milliliter (~0.01 mmol) of the suspension was removed and added to a small fritted funnel. This sample was then neutralized for 1 min with 10% DIEA in DMF, drained, placed in position 1 and reacted with the activated thioester dipeptide analogue (125 μL, 0.05 mmol). During neutralization of the sample, the first subsequent activated amino acid, Boc-proline, was coupled to the resin in vessel A using manual in situ neutralization synthetic cycles with HBTU as the activating agent. After 20 minutes coupling, the peptide-resin in vessel A was washed with DMF, treated with TFA and washed again with DMF. The first peptide-resin sample was then moved to position 1' where dipeptide coupling was allowed to continue.

Cycle 2

The deprotected peptide-resin in vessel A was suspended in 9 mL DMF and 1 mL (~0.01 mmol) was transferred to a second small fritted funnel and placed in position 1. After neutralization of this sample, 125 μL (0.05 mmol) of the activated dipeptide was added to the sample which was placed in the now open position 1. At the same time, activated Boc-Lys was added to Vessel A. After the lysine coupling in vessel A was complete, the first (dipeptide analogue) peptide-resin sample was transferred from position 1' to reaction vessel B. The peptide-resins in A and B were then deprotected with TFA, washed and finally the sample in position 1 was moved to position 1'.

This procedure was continued for a total of 10 cycles of chain elongation, with the final cycle skipping the removal of resin from vessel A. Finally, the sequence PFKK (SEQ ID NO 6, was added to the peptide-resin in vessel B, by stepwise SPPS. Following deprotection and cleavage from the resin, the lyophilized peptide analogue array was analyzed by analytical reverse phase HPLC, electrospray mass spectrometry, and MALDI mass spectrometry.

Synthesis of the Thioester-Containing Model Peptide: LYRA-Gly-SβAla-YGGFL.amide (SEQ ID NO 8) (Example 1)

YGGFL-4-MeBHA-resin (SEQ ID NO 9) was synthesized on an 0.04 mmol scale using standard manual Boc chemistry protocols. Boc-Gly-SβAla (0.2 mmol, 53 mg) and HOBt (0.2 mmol, 28 mg) were dissolved in 1 mL DMF to which DIC (0.2 mmol, 33 μL) was added. After 30 min, the activated dipeptide was added to the deprotected, neutralized (10% DIEA in DMF, 1 min) YGGFL-MBHA (SEQ ID NO 9) resin and allowed to couple for one hour. The sequence was completed following standard manual cycles to synthesize LYRA-Gly-SβAla-YGGFL-4-MeBHA (SEQ ID NO 18) resin. Following deprotection and cleavage from the resin, the lyophilized peptide was characterized by analytical HPLC and by electrospray mass spectrometry. Observed mass: 1203.5±0.4 Da, calculated mass (average isotope composition): 1203.4 Da.

Cleavage of Thioester-Containing Model Peptide (Example 1)

The peptide LYRA-Gly-SβAla-YGGFL.amide, (SEQ ID NO 18) was dissolved in 200 μL of 100 mM Tris pH 9.0, 1 M Gn.HCl, vortexed vigorously for 10 seconds and left at 23° C. for 30 minutes. No hydrolysis was observed under these conditions. However, addition of 20 μL of 1 M NaOH (to pH ~13) gave complete hydrolysis after just 10 minutes. Another sample of the thioester-containing peptide was dissolved in 1 M NH$_2$OH, 200 mM NH$_4$HCO$_3$, pH 6.0 for 30 minutes and completely cleaved into LYRAG-NHOH (observed mass: 593.5±0.5 Da, calculated mass (average isotope composition): 593.7 Da) and SHCH$_2$CH$_2$CO-YGGFL.amide (SEQ ID NO 19) (observed mass 642.5±0.5 Da, calculated mass (average isotope composition): 642.8 Da).

Synthesis of Ester-Containing Model Peptide: YKLFAla-[coo]-LeuYGGFL.amide (SEQ ID NO 20) (Example 1)

The ester-containing model peptide was synthesized by a previously established procedure (Bramson et al. *J. Biol. Chem.* 1985, 260, 15452–15457). 2-Hydroxyisocaproic acid ('Leuceic acid') (1.0 mmol, 131 mg) and HOBt (1.1 mmol, 150 mg) were cooled to 0° C. in 2 mL 1:1 DMF/CH$_2$Cl$_2$, activated with DIC (1.0 mmol) for 15 min and added to NH$_2$-YGGFL-4-MeBHA (SEQ ID NO 9) resin (0.1 mmol). N-ethylmorpholine (0.25 mmol) was added and coupling proceeded for 30 min. The ester bond was created by activating Boc-Ala (1.0 mmol, 190 mg) with 4-dimethylaminopyridine (0.05 mmol, ), DIC (1.0 mmol) and N-ethylmorpholine (0.25 mmol) and reacting with the (α-hydroxy)acyl peptide-resin for 2 hours. The peptide chain assembly was completed by manual stepwise SPPS using in situ neutralization protocols. The peptide was then deprotected and cleaved from the resin and analyzed by analytical HPLC and characterized by electrospray mass spectrometry; [observed mass: 1291.0±0.5 Da, calculated mass (average isotope composition): 1290.6 Da].

Cleavage of the Ester-Containing Model Peptide (Example 1)

The ester-containing peptide YKLFAla-[COO]-LeuYGGFL.amide (SEQ ID NO 20) was allowed to stand in 6M Guanidine HCl, 100 mM Na phosphate pH 10 for six hours. Complete hydrolysis was observed. The resulting peptides were separated by analytical HPLC and characterized by electrospray mass spectrometry. (YKLFA-OH, (SEQ ID NO 21) [observed mass: 640.5±0.5 Da, calculated mass (average isotope compositon): 640.8 Da]; HO-LYGGFL.amide, (SEQ ID NO 22) [observed mass: 669.0±0.5 Da, calculated mass (average isotope compositon): 668.8 Da]. By contrast, the ester-containing peptide was completely stable to treatment with 1 M NH$_2$OH, 200 mM NH$_4$HCO$_3$, pH 6.0 for up to 12 hours, as monitored by analytical HPLC.

Hydroxylamine Cleavage of the Nine Component Peptide Gly-SβAla Analogue Array of the Parent Sequence PFKK-[GDILRIRDKP]-EEAcpRLKLKAR (SEQ ID NO 7) (Example 1)

0.3 mg (0.1 μmol/component) of the peptide array was dissolved in 100 μL 1M NH$_2$OH.HCl, 200 mM NH$_4$HCO$_3$ pH 6.0. After 30 minutes, the array was analyzed by analytical reverse phase HPLC and MALDI mass spectrometry.

Solid Phase Peptide Synthesis (Example 2)

Except where noted all peptides were synthesized according to the machine-assisted in situ neutralization/HBTU activation protocol for Boc-solid phase chemistry as previously described (Schnölzer et al. Int. J. Pept. Protein Res. 1992, 40, 180–193) using a modified Applied Biosystems 430A peptide synthesizer. Following synthesis, the $N^\alpha$Boc group was removed, and the peptide cleaved from the resin with simultaneous removal of sidechain protecting groups by treatment for 1 hour at 0° C. with anhydrous HF containing 5% anisole or 5% p-cresol as a scavenger. After evaporation of the HF, the crude peptide was precipitated and washed with cold diethyl ether, dissolved in 1:1 acetonitrile:$H_2O$ containing 0.1% TFA, filtered to remove the resin, and lyophilized.

Synthesis of Native N-terminal cCrk SH3 Domain (cCrk Residues 134–191) (Example 2)

The 58 amino acid residue polypeptide was synthesized using 0.12 mmol Boc-Arg(Tos)-$OCH_2$-Pam resin, loading 0.59 mmol/g (Applied Biosystems, Foster City, Calif.). Standard sidechain protecting groups (Schnölzer et al. Int. J. Pept. Protein Res. 1992, 40, 180–193) were used except for the tryptophan indole moiety which was left unprotected because subsequent syntheses of base labile analogues would not permit the nucleophilic removal of the usual formyl protecting group. HF cleavage of 300 mg of peptide resin from the resin gave 195 mg of lyophilized crude peptide. A 5 mg sample of the crude peptide was purified by semipreparative HPLC on a 20%–40%B gradient over 45 minutes to give 1.4 mg purified product (23% yield, calculated from the original loading of the resin). The purified peptide product was a single peak by analytical HPLC and was pure by electrospray mass spectrometry: Observed mass 6962±1 Da: Calculated mass for $C_{313}H_{470}N_{84}O_{95}S_1$ 6961.8 Da (average isotope distribution).

Functional Characterization of the Synthetic 58-residue cCrk N-terminal SH3 Domain The affinity of the synthetic SH3 domain to two C3G derived peptides was determined by measuring the increase in the protein domain tryptophan fluorescence upon ligand binding, following the procedure described in Lim et al. Protein Science. 1994, 3, 1261–1266. The purified and lyophilized 58 residue polypeptide chain (0.2 mg) was folded by dissolving in 0.6 mL of 20 mM Hepes, 60 mM NaCl, pH 7.3 to produce a folded protein solution (~50 μM). Peptide stock solutions of both the C3G-derived peptide [PPPALPPKKR.amide] (SEQ ID NO 23) (71.9 μM) and the C3G-derived peptide designed for attachment to an affinity column [Ac-CWAcp-PPPALPPKKR.amide] (SEQ ID NO 24) (71.5 μM) were obtained by dissolving the lyophilized peptides in the same buffer. Peptide concentrations were determined by quantitative amino acid analysis.

Synthesis of the Nine Component Analogue Array of cCrk (134–191) (Example 2)

The target array of analogue polypeptide chains is shown in FIG. 23. The first part of the sequence, corresponding to cCrk (166–191), was synthesized on a 0.2 mmol Boc-Arg (Tos)-$OCH_2$-Pam resin, (0.59 mmol/g) using machine-assisted synthetic cycles. The array of polypeptide analogues was manually synthesized on ~0.05 mmol (250 mg) of this peptide resin by a modified split-resin procedure previously described in Hayashibara et al. J. Am. Chem. Soc. 1991, 113, 5103–5106 (similar readout system developed for use in DNA systems). Boc-Gly-SβAla-OH (0.25 mmol, 66 mg) was preactivated for one hour with DIC (0.25 mmol, 38 μL; Aldrich) and HOBt (0.25 mmol; Aldrich) in DMF: total volume 650 μL. The apparatus for manual synthesis consisted of two standard manual synthesis reaction vessels, labeled A and B and two small fritted funnels in a test tube rack in positions 1 and 1'.

Cycle 1

First, the $N^\alpha$-Boc-deprotected cCrk(166–191)peptide-resin (50 μmol) was suspended in 10 mL DMF. One milliliter (~5 μmol) of the suspension was removed and added to a small fritted funnel. This sample was then neutralized for 1 min with 10% DIEA in DMF, drained, placed in position 1 and reacted with the activated dipeptide analogue (65 μL, 25 μmol). During neutralization of the sample, the coupling of the first activated amino acid, Boc-Pro$^{165}$, to the peptide-resin in reaction vessel A was initiated using manual in situ neutralization synthetic cycles with HBTU as the activating agent. After 20 minutes, vessel A was washed with DMF, treated with TFA and washed again with DMF. The removed peptide-resin sample in position 1 was then moved to position 1' where coupling of the dipeptide analogue was continued.

Cycle 2

The peptide-resin in vessel A was suspended in 9 mL DMF and 1 mL (~5 μmol) was transferred to a second small fritted funnel and placed in position 1. After neutralization of this sample and addition of activated Lys$^{164}$ to A, the activated dipeptide (65 μL, 25 μmol) was added to the sample which was placed in the now open position 1. Following the Boc-Lys$^{164}$ coupling in vessel A, the first analogue-modified peptide resin sample in position 1' was washed with DMF and then transferred to reaction vessel B. The peptide-resins in reaction vessels A and B were then deprotected with TFA, washed and finally, the second peptide-resin sample in position 1 was moved to position 1', where coupling of the dipeptide analogue was continued.

The procedure described above was continued for 10 cycles, through the addition of residue 156. In the final cycle the removal of a peptide-resin sample from vessel A and dipeptide coupling steps were omitted. Finally, half of the mixture of peptide-resins in vessel B (25 μmol total) containing nine peptide analogues, was removed and transferred to an Applied Biosystems 430A peptide synthesizer for addition of the remaining amino acids, cCrk 134–155. This procedure gave a product mixture of 58 residue peptide-resins. Following deprotection and cleavage from the resin, the lyophilized peptide array was analyzed by analytical reverse phase HPLC and MALDI mass spectrometry.

Synthesis of C3G-derived Ligand and Control Peptides (Example 2)

The peptides corresponding to the C3G-derived ligand, Ac-CWAcp-PPPALPPKKR.amide (SEQ ID NO 24) and the control, Ac-CAcpYGGFL.amide, (SEQ ID NO 25) were synthesized on 4-methyl benzhydrylamine resin (0.93 mmol/g Peninsula Laboratories) and were cleaved from the resin support using p-cresol as a scavenger, and then purified by semipreparative HPLC using a 25%–50% acetonitrile gradient over 30 minutes. The products were characterized by ESMS. Ac-CWAcpPPPALPPKKR.amide; (SEQ ID NO 24) Observed mass: 1543±1 Da. Calculated mass for $C_{74}H_{118}N_{20}O_{14}S_1$ (average isotope composition): 1543.9 Da, Ac-CAcpYGGFL.amide; (SEQ ID NO 25) Observed mass: 813.5±0.5 Da, Calculated mass for $C_{39}H_{56}N_8O_9S_1$ (average isotope composition): 814.0 Da.

Preparation of Affinity Columns (Example 2)

The C3G-derived synthetic peptide affinity column was prepared by adding 10 mg of lyophilized Ac-CWAcpPPPALPPKKR.amide (SEQ ID NO 24) (Acp= ε-amino caproic acid) in 2 mL of 50 mM Tris, 5 mM EDTA, pH 8.0 buffer to Sulfolink™ resin (Pierce), equilibrated in the same buffer, for 1 hour while shaking. Unreacted iodoalkyl groups on the resin were then blocked by treatment with 50 mM cystamine, 50 mM Tris, 5 mM EDTA, pH 8.0 buffer for 1 hour. The loading of the column was determined by UV absorbance of the unreacted peptide solution and was approximately 5 μmol/mL. A similar procedure was used to attach the control peptide Ac-CAcpYGGFL.amide (SEQ ID NO 25) to the another batch of the Sulfolink™ support.

Affinity Selection of Synthetic cCrk SH3 Domain (Example 2)

Lyophilized crude synthetic polypeptide corresponding to the cCrk SH3 domain (1.5 mg) and BSA (8.5 mg) were dissolved in 20 mM HEPES, 50 mM NaCl, pH 7.3 buffer (400 μL) and loaded on to a 1 mL C3G-derived synthetic peptide affinity column pre-equilibrated with the same buffer. The column was washed with 4 mL each of 50 mM NaCl, 100 mM NaCl, 200 mM NaCl, 300 mM NaCl, 400 mM NaCl, 500 mM NaCl and 1000 mM NaCl, 0.1 M phosphate, pH 7.0 buffer. The column was then washed with 1 M $NH_2OH$ 200 mM $NH_4CO_3$ pH 6.0 (4 mL) and finally eluted in 6M Gn.HCl 100 mM phosphate pH 6.5 (4 mL). Samples from all column fractions were monitored by absorbance at 280 nm and by HPLC.

Affinity Chromatography the Nine-membered Arrays (Example 2)

Affinity chromatography of the arrays of protein analogues was carried out as follows. The crude protein array (1.5 mg) was dissolved in 20 mM HEPES, 50 mM NaCl, pH 7.3 buffer (600 μL) and loaded on to a 1 mL C3G-derived synthetic peptide affinity column pre-equilibrated with the same buffer. After incubation at room temperature for a period of 6–8 hours the column was washed with 0.5 M NaCl in 0.1 M sodium phosphate, pH 7.0 buffer (6×1 mL) to remove any non-specifically bound proteins. The first two 1 mL fractions were collected and immediately mixed with an equal volume of 1 M $NH_2OH$, 20 mM $NH_4HCO_3$, pH 5.5 buffer to cleave any thioester-containing protein analogues. Following a second 6×1 mL column wash with 1 M NaCl in 0.1 M sodium phosphate, pH 7.0 buffer, specifically-bound protein analogues were chemically cleaved and eluted from the affinity column by washing with 1 M $NH_2OH$, 20 mM $NH_4HCO_3$, pH 5.5 buffer (4×1 mL). Samples of the eluted fractions were monitored by UV absorbance at 280 nm. This procedure was used for both the C3G peptide column and for the control column loaded with Ac-C-Acp-YGGFL.amide. To accommodate MALDI analysis, both the 0.5M NaCl wash and 1 M $NH_2OH$ fractions were desalted on a low pressure, disposable C-18 column, washed with HPLC buffer A and peptide fragments eluted with 1.5 mL 60% acetonitrile in water, 0.1% TFA.

MALDI Mass Spectrometric Analysis of Peptide Fragments (Example 2)

After desalting, the affinity column fractions were analyzed by MALDI mass spectrometry. Samples were prepared by adding a 2 μL aliquot of the 1.5 mL desalted column fraction to 5 μL of a saturated solution of α-cyano-4-hydroxycinnamic acid in 50% acetonitrile in water, 0.1% TFA. From this mixture, 2 μL, containing ~1–10 pmole of each peptide component was added to a stainless steel probe tip (3.14 $mm^2$.) and the solvent allowed to evaporate slowly under ambient conditions. Mass spectra were recorded using a prototype laser desorption, linear time-of-flight mass spectrometer from Ciphergen Biosystems Inc. (Palo Alto, Calif.). Samples were ionized using 337 nm radiation output from a nitrogen laser (Laser Science, Inc., Newton Mass.). All spectra were acquired in the positive ion mode and summed over 20–50 laser pulses. Time-to mass conversion was accomplished by internal calibration using the $[M+H]^+$ signals from the largest and smallest peptide components in each array.

Synthesis of Peptides (Example 3)

With the exception of protein arrays all peptides were chemically synthesized according to optimized solid-phase methods (Schnölzer (1992) *Int. J. Pept. Protein Res.* 40, 180–193) and purified by preparative reverse-phase HPLC using a Vydac C-18 column. In all cases, peptide composition and purity were confirmed by electrospray mass spectrometry and analytical reverse-phase HPLC.

Synthesis of C-Crk SH3 Protein Arrays (Example 3)

A detailed description of the split-resin procedure used (examples 1 and 2; supra). Briefly, the technique involves the use of two reaction vessels with identical synthetic manipulations being carried out in each. Standard stepwise chain assembly was initiated on resin in the first vessel (0.2 mmole scale); peptide-resin samples were repeatedly removed from the first vessel at each stage of the synthesis, and analogue units were introduced into the polypeptide chain by coupling as preformed HOBt esters; after modification, the samples were transferred to the second vessel for completion of the chain assembly by standard stepwise chain assembly. The size of the samples was adjusted to yield approximately equal molar amounts of each protein analogue in the array (dependent on the number af protein analogues in a given array). The dipeptide analogues Gly-[COS]-βAla and Gly-[COS]-Gly were prepared as previously described (Hojo et al. (1991) *Bull. Chem. Soc. Jpn.* 64, 111–117). Upon completion of the synthesis, each parent protein array was characterized as follows: crude protein array (~1 mg) was dissolved in a cleavage buffer consisting of 1 M $NH_2OH$, 20 mM $NH_4HCO_3$, pH 6.5 buffer (1 ml) and stirred for 15 minutes. The cleaved arrays were then exchanged into a 70% $CH_3CN$:30% $H_2O$, 0.1% TFA solvent system (using a 1 ml C-18 desalting column) and immediately analysed by MALDI mass spectrometry.

Synthesis of Peptide Affinity Columns (Example 3)

The C3G peptide affinity column was prepared as follows. The peptide Ac-CWBPPPALPPKKR.amide (SEQ ID NO 24) (B=ε-aminocaproic acid) was dissolved in 50 mM Tris, 5 mM EDTA, pH 8.0 (10 mg in 2 ml) and shaken with Sulfolink™ resin (Pierce) for 1 hour. Unreacted iodoalkyl groups on the resin were then blocked by treatment with 50 mM cystamine, 50 mM Tris, 5 mM EDTA, pH 8.0 buffer. The loading of the column was determined by UV to be approximately 5 μmole/ml. A similar procedure was used to attach the control peptide Ac-CBYGGFL.amide (SEQ ID NO 25) (YGGFL=leucine enkephalin) to the Sulfolink™ support.

Affinity Selection of Synthetic c-Crk SH3 (Example 3)

HPLC purified synthetic c-Crk SH3 (1.5 mg) was dissolved in 20 mM Hepes, 50 mM NaCl, pH 7.3 buffer (400 μl) and applied to a 1 mL C3G peptide affinity column pre-equilibrated with the same buffer. After 6–8 hours (required for optimal binding) the column was washed with, in turn: 0.5 M NaCl, 0.1 M sodium phosphate, pH 7.0 buffer (6×1 ml), 1 M NaCl, 0.1 M sodium phosphate, pH 7.0 buffer (6×1 ml) and 1 M $NH_2OH$, 20 mM $NH_4HCO_3$, pH 5.5 buffer (6×1 ml). The applied material did not elute from the column under any of these conditions, but was readily recovered (with ~85% yield) by washing the column with a 6 M GuHCl, 0.1 M sodium phosphate, pH 7.0 buffer (2×1 ml). In contrast, the synthetic SH3 domain did not specifically bind to the leucine enkaphalin control column under identical conditions to the above.

Affinity Selection of Protein Arrays (Example 3)

The crude protein array (1.5 mg) was dissolved in 20 mM Hepes, 50 mM NaCl. pH 7.3 buffer (600 µl) and loaded on to a 1 ml C3G peptide affinity column pre-equilibrated with the same buffer. After 6–8 hours the non-specifically bound material was eluted from the column by washing with 0.5 M NaCl, 0.1 M sodium phosphate, pH 7.0 buffer (6×1 ml). Eluted material (typically in the first and second wash) was immediately cleaved by dilution into 1 M $NH_2OH$, 20 mM $NH_4HCO_3$, pH 5.5 buffer. Following further column washing with 1 M NaCl, 0.1 M sodium phosphate, pH 7.0 buffer, the specifically bound material (active pool) was chemically cleaved and simultaneously eluted from the affinity column by washing with 1 M $NH_2OH$, 20 mM $NH_4HCO_3$, pH 6.5 buffer (4×1 ml). Eluted fractions were exchanged into a 70% $CH_3CN$:30% $H_2O$, 0.1% TFA solvent system and immediately analysed by MALDI mass spectrometry.

MAIDI Analysis of Peptide Arrays (Example 3)

All samples were prepared by adding 2 µL of the desalted column fraction to 5 µL of a saturated solution of α-cyano cinnaminic acid in 50% acetonitrile in water, 0.1% TFA. From this mixture, 2 µL, containing ~1–10 pmole of each pepide component was added to a stainless steel probe tip and the solvent allowed to evaporate under ambient conditions. Mass spectra were recorded using a prototype laser desorption, linear time-of-flight mass spectrometer from Ciphergen Biosystems (Palo Alto, Calif.). Samples were desorbed/ionized using 337 nm radiation output from a nitrogen laser (Laser Science, Inc., Newton Mass.). All spectra were acquired in the positive ion mode and summed over 20–50 laser pulses. Time-to mass conversion was accomplished by internal calibration using the the $[M+H]^+$ signals from the largest and smallest peptide components in each array.

What is claimed is:

1. A process for obtaining a molecular signature of a protein or protein domain, the protein or protein domain having an amino acid sequence with length m, each amino acid position within the sequence being represented by $(aa)_n$ where $1 \leq n \leq m$, the protein or protein domain having optimal binding conditions for binding to a target molecule and forming a binding conjugate therewith, the process comprising the following steps:

Step A: providing a peptide ladder library comprising a collection of m peptides, each peptide being represented by $(peptide)_n$, each peptide having the same amino acid sequence as the protein or protein domain except that the amino acid position $(aa)_n$ of $(peptide)_n$ is replaced by a substitute amino acid, the position of the substitute amino acid differing for each peptide within the peptide ladder library, the substitute amino acid at position $(aa)_n$ being linked to the amino acid at position $(aa)_{n+1}$ by means of a selectively cleavable bond; then Step B: contacting the peptide ladder library of said Step A with the target molecule under binding conditions for forming bound peptides and unbound peptides, the bound peptides being bound to the target molecule; then Step C: separating and isolating the bound peptides from the unbound peptides of said Step B; then Step D: cleaving the selectively cleavable bond of each of the bound peptides isolated in said Step C for producing peptide cleavage products; then Step E: detecting and identifying each of the peptide cleavage products of said Step D for identifying amino acids within the amino acid sequence of the protein associated with binding to the target molecule; and then Step F: constructing a subsequence which defines the molecular signature of the protein or protein domain with respect to the target molecule using the identity of the peptide cleavage products of said Step E, the molecular signature being defined by the subsequence of the amino acid sequence selected from amongst positions $(aa)_n$ which, if individually replaced by a substitute amino acid, lead to a loss of binding affinity by the protein or protein domain with respect to the target molecule.

2. A method for obtaining a molecular signature of a protein or protein domain as described in claim 1 wherein the selectively cleavable bond within the peptide of said Step A is selected from the group consisting of thioester bonds and ester bonds.

3. A method for obtaining a molecular signature of a protein or protein domain as described in claim 1 wherein the substitute amino acid in said Step A is selected from the group consisting of L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine, D-alanine, D-arginine, D-aspartic acid, D-asparagine, D-cysteine, D-cystine, D-glutamic acid, D-glutamine, D-glycine, D-histidine, D-isoleucine, D-leucine, D-lysine, D-methionine, D-phenylalanine, D-proline, D-serine, D-threonine, D-tryptophan, D-tyrosine, D-valine, L-α-aminobutyric acid, D-α-aminobutyric acid, L-γ-aminobutyric acid, D-γ-aminobutyric acid, L-ϵ-aminocaproic acid, D-ϵ-aminocaproic acid, L-homophenylalanine, D-homophenylalanine, L-alloisoleucine, D-alloisoleucine, L-β-2-napthylalanine, D-β-2-napthylalanine, L-norvaline, D-norvaline, L-ornithine, D-omithine, L-pyridyl alanine, D-pyridyl alanine L-2-thienylalanine, D-2-thienylalanine, L-methyltyrosine, D-methyltyrosine, L-citrulline D-citrulline, L-homocitrulline, and D-homocitrulline.

4. A process for obtaining a molecular signature of a protein or protein domain, the protein or protein domain having an amino acid sequence with length m, each amino acid position within the sequence being represented by $(aa)_n$ where $1 \leqq n \leqq m$, the protein or protein domain having optimal binding conditions for binding to a target molecule and for forming a binding conjugate therewith, the process comprising the following steps:

Step A: providing a peptide ladder library comprising a collection of m peptides, each peptide being represented by $(\text{peptide})_n$, each peptide having the same amino acid sequence as the protein or protein domain except that the amino acid position $(aa)_n$ of $(\text{peptide})_n$ is replaced by a substitute amino acid, the position of the substitute amino acid differing for each peptide within the peptide ladder library, the substitute amino acid position $(aa)_n$ being linked to the amino acid at position $(aa)_{n+1}$ by means of a selectively cleavable bond; then Step B: contacting the peptide ladder library of said Step A with the target molecule under binding conditions for forming bound peptides and unbound peptides, the bound peptides being bound to the target molecule; then Step C: separating and isolating the unbound peptides from the bound peptides of said Step B; then Step D: cleaving the selectively cleavable bond of each of the unbound peptides isolated in said Step C for producing peptide cleavage products; then Step E: detecting and identifying each of the peptide cleavage products of said Step D for identifying amino acids within the amino acid sequence of the protein or protein domain which are potentially un-associated with binding to the target molecule; and then Step F: constructing a subsequence which defines the molecular signature of the protein or protein domain with respect to the target molecule using the identity of the peptide cleavage products of said Step E, the molecular signature being defined by the subsequence of the amino acid sequence selected from amongst positions $(aa)_n$ which, if individually replaced by a substitute amino acid, do not lead to a loss of binding affinity by the protein or protein domain with respect to the target molecule.

5. A method for obtaining a molecular signature of a protein or protein domain as described in claim 4 wherein the selectively cleavable bond within the peptide of said Step A is selected from the group consisting of thioester bonds and ester bonds.

6. A method for obtaining a molecular signature of a protein or protein domain as described in claim 4 wherein the substitute amino acid in said Step A is selected from the group consisting of L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine, D-alanine, D-arginine, D-aspartic acid, D-asparagine, D-cysteine, D-cystine, D-glutamic acid, D-glutamine, D-glycine, D-histidine, D-isoleucine, D-leucine, D-lysine, D-methionine, D-phenylalanine, D-proline, D-serine, D-threonine, D-tryptophan, D-tyrosine, D-valine, L-α-aminobutyric acid, D-α-aminobutyric acid, L-γ-aminobutyric acid, D-γ-aminobutyric acid, L-ϵ-aminocaproic acid, D-ϵ-aminocaproic acid, L-homophenylalanine, D-homophenylalanine, L-alloisoleucine, D-alloisoleucine, L-β-2-napthylalanine, D-β-2-napthylalanine, L-norvaline, D-norvaline, L-omithine, D-omithine, L-pyridyl alanine, D-pyridyl alanine, L-2-thienylalanine, D-2-thienylalanine, L-methyltyrosine, D-methyltyrosine, L-citruline, D-citrulline, L-homocitrulline, and D-homocitrulline.

* * * * *

SEQUENCE LISTING

```
<160> NUMBER OF SEQ ID NOS: 37

<210> SEQ ID NO 1
<211> LENGTH: 11
<212> TYPE: PRT
<213> ORGANISM: Mus musculus

<400> SEQUENCE: 1

Lys Gly Asp Ile Leu Arg Ile Arg Asp Lys Pro
 1               5                   10

<210> SEQ ID NO 2
<211> LENGTH: 16
<212> TYPE: PRT
<213> ORGANISM: Mus musculus

<400> SEQUENCE: 2

Pro Phe Lys Lys Gly Asp Ile Leu Arg Ile Arg Asp Lys Pro Glu Glu
 1               5                   10                  15

<210> SEQ ID NO 3
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: modified with e-amino caproic acid residue; Acp
<223> OTHER INFORMATION: Description of Artificial Sequence: synthesized

<400> SEQUENCE: 3

Arg Leu Lys Leu Lys Ala Arg
 1               5

<210> SEQ ID NO 4
<211> LENGTH: 10
<212> TYPE: PRT
<213> ORGANISM: Mus musculus

<400> SEQUENCE: 4

Gly Asp Ile Leu Arg Ile Arg Asp Lys Pro
 1               5                   10

<210> SEQ ID NO 5
<211> LENGTH: 9
<212> TYPE: PRT
```

```
<213> ORGANISM: Artificial Sequence
<220> FEATURE:
<221> NAME/KEY: MOD_RES
<222> LOCATION: (3)
<223> OTHER INFORMATION: modified with e-amino caproic acid
<223> OTHER INFORMATION: Description of Artificial Sequence: synthesized

<400> SEQUENCE: 5

Glu Glu Arg Leu Lys Leu Lys Ala Arg
  1               5

<210> SEQ ID NO 6
<211> LENGTH: 4
<212> TYPE: PRT
<213> ORGANISM: Mus musculus

<400> SEQUENCE: 6

Pro Phe Lys Lys
  1

<210> SEQ ID NO 7
<211> LENGTH: 23
<212> TYPE: PRT
<213> ORGANISM: Artificial Sequence
<220> FEATURE:
<221> NAME/KEY: MOD_RES
<222> LOCATION: (17)
<223> OTHER INFORMATION: modified with e-amino caproic acid
<223> OTHER INFORMATION: Description of Artificial Sequence: synthesized

<400> SEQUENCE: 7

Pro Phe Lys Lys Gly Asp Ile Leu Arg Ile Arg Asp Lys Pro Glu Glu
  1               5                   10                  15

Arg Leu Lys Leu Lys Ala Arg
            20

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: synthesized
<221> NAME/KEY: MOD_RES
<222> LOCATION: (5)
<223> OTHER INFORMATION: modified with a beta-thiopropionic acid residue
      forming a thioester bond

<400> SEQUENCE: 8

Leu Tyr Arg Ala Gly Tyr Gly Gly Phe Leu
  1               5                   10

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: synthesized
<221> NAME/KEY: MOD_RES
<222> LOCATION: (5)
<223> OTHER INFORMATION: leucine is connected to 4-methylbenzhydramine
      resin

<400> SEQUENCE: 9

Tyr Gly Gly Phe Leu
  1               5

<210> SEQ ID NO 10
<211> LENGTH: 5
```

```
<212> TYPE: PRT
<213> ORGANISM: Artificial Sequence
<220> FEATURE:
<223> OTHER INFORMATION: Description of Artificial Sequence: synthesized
<221> NAME/KEY: MOD_RES
<222> LOCATION: (5)
<223> OTHER INFORMATION: modified by the -NHOH function at the
      C-terminus

<400> SEQUENCE: 10

Leu Tyr Arg Ala Gly
  1               5

<210> SEQ ID NO 11
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: modified by the beta-thiopropionic acid at the
      N-terminus
<223> OTHER INFORMATION: Description of Artificial Sequence: synthesized

<400> SEQUENCE: 11

Tyr Gly Gly Phe Leu
  1               5

<210> SEQ ID NO 12
<211> LENGTH: 9
<212> TYPE: PRT
<213> ORGANISM: Artificial Sequence
<220> FEATURE:
<221> NAME/KEY: MOD_RES
<222> LOCATION: (6)
<223> OTHER INFORMATION: modified by an alpha-hydroxy acid
<223> OTHER INFORMATION: Description of Artificial Sequence: synthesized

<400> SEQUENCE: 12

Tyr Lys Leu Phe Ala Gly Gly Phe Leu
  1               5

<210> SEQ ID NO 13
<211> LENGTH: 9
<212> TYPE: PRT
<213> ORGANISM: human C3G

<400> SEQUENCE: 13

Pro Pro Ala Leu Pro Pro Lys Lys Arg
  1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: synthesized
<221> NAME/KEY: MOD_RES
<222> LOCATION: (3)
<223> OTHER INFORMATION: modified with e-amino caproic acid residue

<400> SEQUENCE: 14

Cys Trp Pro Pro Ala Leu Pro Pro Lys Lys Arg
  1               5                  10

<210> SEQ ID NO 15
<211> LENGTH: 7
<212> TYPE: PRT
<213> ORGANISM: Artificial Sequence
```

```
<220> FEATURE:
<223> OTHER INFORMATION: Description of Artificial Sequence: synthesized
<221> NAME/KEY: MOD_RES
<222> LOCATION: (3)
<223> OTHER INFORMATION: modified with e-amino caproic acid residue

<400> SEQUENCE: 15

Cys Trp Tyr Gly Gly Phe Leu
  1               5

<210> SEQ ID NO 16
<211> LENGTH: 10
<212> TYPE: PRT
<213> ORGANISM: Mus musculus

<400> SEQUENCE: 16

Gly Asp Arg Ile Leu Arg Ile Asp Lys Pro
  1               5                  10

<210> SEQ ID NO 17
<211> LENGTH: 7
<212> TYPE: PRT
<213> ORGANISM: Mus musculus

<400> SEQUENCE: 17

Asn Asp Glu Glu Asp Leu Pro
  1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: synthesized
<221> NAME/KEY: MOD_RES
<222> LOCATION: (6)
<223> OTHER INFORMATION: modified by the presence of beta-thiopropionic
      acid residue

<400> SEQUENCE: 18

Leu Tyr Arg Ala Gly Tyr Gly Gly Phe Leu
  1               5                  10

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: synthesized
<221> NAME/KEY: MOD_RES
<222> LOCATION: (1)
<223> OTHER INFORMATION: modified by the beta-thiopropionic acid residue

<400> SEQUENCE: 19

Tyr Gly Gly Phe Leu
  1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: synthesized
<221> NAME/KEY: MOD_RES
<222> LOCATION: (6)
<223> OTHER INFORMATION: modified by the presence of an ester bond in
      the backbone; leu is the alpha-hydroxy isocaproic acid residue

<400> SEQUENCE: 20
```

Tyr Lys Leu Phe Ala Leu Tyr Gly Gly Phe Leu
 1               5                   10

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: synthesized

<400> SEQUENCE: 21

Tyr Lys Leu Phe Ala
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: synthesized

<400> SEQUENCE: 22

Leu Tyr Gly Gly Phe Leu
 1               5

<210> SEQ ID NO 23
<211> LENGTH: 10
<212> TYPE: PRT
<213> ORGANISM: human C3G

<400> SEQUENCE: 23

Pro Pro Pro Ala Leu Pro Pro Lys Lys Arg
 1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: synthesized
<221> NAME/KEY: MOD_RES
<222> LOCATION: (3)
<223> OTHER INFORMATION: modified with e-amino caproic acid residue

<400> SEQUENCE: 24

Cys Trp Pro Pro Pro Ala Leu Pro Pro Lys Lys Arg
 1               5                   10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: synthesized
<221> NAME/KEY: MOD_RES
<222> LOCATION: (2)
<223> OTHER INFORMATION: modified with the unnatural e-amino caproic
      acid residue

<400> SEQUENCE: 25

Cys Tyr Gly Gly Phe Leu
 1               5

<210> SEQ ID NO 26
<211> LENGTH: 8
<212> TYPE: PRT
<213> ORGANISM: Mus musculus

```
<400> SEQUENCE: 26

Ile Leu Arg Ile Arg Asp Lys Pro
 1               5

<210> SEQ ID NO 27
<211> LENGTH: 7
<212> TYPE: PRT
<213> ORGANISM: Mus musculus

<400> SEQUENCE: 27

Leu Arg Ile Arg Asp Lys Pro
 1               5

<210> SEQ ID NO 28
<211> LENGTH: 6
<212> TYPE: PRT
<213> ORGANISM: Mus musculus

<400> SEQUENCE: 28

Arg Ile Arg Asp Lys Pro
 1               5

<210> SEQ ID NO 29
<211> LENGTH: 4
<212> TYPE: PRT
<213> ORGANISM: Mus musculus

<400> SEQUENCE: 29

Lys Gly Asp Ile
 1

<210> SEQ ID NO 30
<211> LENGTH: 5
<212> TYPE: PRT
<213> ORGANISM: Mus musculus

<400> SEQUENCE: 30

Ile Arg Asp Lys Pro
 1               5

<210> SEQ ID NO 31
<211> LENGTH: 5
<212> TYPE: PRT
<213> ORGANISM: Mus musculus

<400> SEQUENCE: 31

Lys Gly Asp Ile Leu
 1               5

<210> SEQ ID NO 32
<211> LENGTH: 4
<212> TYPE: PRT
<213> ORGANISM: Mus musculus

<400> SEQUENCE: 32

Arg Asp Lys Pro
 1

<210> SEQ ID NO 33
<211> LENGTH: 6
<212> TYPE: PRT
<213> ORGANISM: Mus musculus

<400> SEQUENCE: 33
```

```
<210> SEQ ID NO 34
<211> LENGTH: 7
<212> TYPE: PRT
<213> ORGANISM: Mus musculus

<400> SEQUENCE: 34

Lys Gly Asp Ile Leu Arg Ile
  1               5

<210> SEQ ID NO 35
<211> LENGTH: 8
<212> TYPE: PRT
<213> ORGANISM: Mus musculus

<400> SEQUENCE: 35

Lys Gly Asp Ile Leu Arg Ile Arg
  1               5

<210> SEQ ID NO 36
<211> LENGTH: 9
<212> TYPE: PRT
<213> ORGANISM: Mus musculus

<400> SEQUENCE: 36

Lys Gly Asp Ile Leu Arg Ile Arg Asp
  1               5

<210> SEQ ID NO 37
<211> LENGTH: 58
<212> TYPE: PRT
<213> ORGANISM: Mus musculus

<400> SEQUENCE: 37

Ala Glu Tyr Val Arg Ala Leu Phe Asp Phe Asn Gly Asn Asp Glu Glu
  1               5                  10                  15

Asp Leu Pro Phe Lys Lys Gly Asp Ile Leu Arg Ile Arg Asp Lys Pro
                 20                  25                  30

Glu Glu Gln Trp Trp Asn Ala Glu Asp Ser Glu Gly Lys Arg Gly Met
             35                  40                  45

Ile Pro Val Pro Tyr Val Glu Lys Tyr Arg
     50                  55
```

Lys Gly Asp Ile Leu Arg
 1               5